United States Patent
Takeuchi et al.

(10) Patent No.: US 6,677,110 B2
(45) Date of Patent: Jan. 13, 2004

(54) DYE-FORMING COUPLER, SILVER HALIDE PHOTOGRAPHIC LIGHT-SENSITIVE MATERIAL, AND AZOMETHINE DYE COMPOUND

(75) Inventors: Kiyoshi Takeuchi, Minami-ashigara (JP); Shigeki Uehira, Minami-ashigara (JP); Mario Aoki, Minami-ashigara (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 10/106,192

(22) Filed: Mar. 27, 2002

(65) Prior Publication Data

US 2003/0064332 A1 Apr. 3, 2003

(30) Foreign Application Priority Data

Mar. 30, 2001 (JP) .................................. 2001-102538
Mar. 30, 2001 (JP) .................................. 2001-102698

(51) Int. Cl.$^7$ .................. G03C 1/08; G03C 7/26; G03C 7/32
(52) U.S. Cl. ................... 430/558; 430/557; 430/543
(58) Field of Search .................. 430/543, 558, 430/557

(56) References Cited

U.S. PATENT DOCUMENTS

| | | | |
|---|---|---|---|
| 3,841,880 A | | 10/1974 | Kertel |
| 5,021,330 A | * | 6/1991 | Bergthaller et al. .......... 430/558 |
| 5,024,930 A | * | 6/1991 | Kita et al. .................. 430/558 |
| 5,213,958 A | | 5/1993 | Motoki et al. |
| 5,427,902 A | | 6/1995 | Shimura et al. |
| 5,455,149 A | | 10/1995 | Bergthaller |
| 6,043,017 A | * | 3/2000 | Bergthaller ................. 430/558 |

FOREIGN PATENT DOCUMENTS

| | | |
|---|---|---|
| EP | 0 336 411 A2 | 10/1989 |
| EP | 0 953 870 | 11/1999 |
| JP | 52-082423 A | 7/1977 |
| JP | 58-111943 A | 7/1983 |
| JP | 4-78582 A | 3/1992 |

\* cited by examiner

*Primary Examiner*—Geraldine Letscher
(74) *Attorney, Agent, or Firm*—Birch, Stewart, Kolasch & Birch, LLP

(57) ABSTRACT

A dye-forming coupler of formula (I):

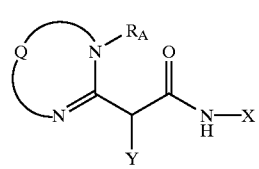

formula (I)

wherein Q represents a residue that forms, together with —N—C=N—, a nitrogen-containing 6-membered ring; $R_A$ represents an aryl, heterocyclic, or —$(R_1)_r$—$(R_4)_m$ group; X represents an aryl group; Y represents a hydrogen atom, or a group capable of being split-off upon a coupling reaction with an oxidized product of a developing agent:

wherein, when $R_A$ represents an —$(R_1)_r$—$(R_4)_m$ group, $R_1$ represents a methylene group, a methine group, or a carbon atom; r is 1 to 30; $R_4$ represents a substituent except for a hydrogen atom; m is 1 to 30; and the —$(R_1)_r$—$(R_4)_m$ group does not represent a straight-chain alkyl group. A silver halide photographic light-sensitive material which contains at least one of the coupler. An azomethine dye compound derived from the coupler.

7 Claims, No Drawings

DYE-FORMING COUPLER, SILVER HALIDE PHOTOGRAPHIC LIGHT-SENSITIVE MATERIAL, AND AZOMETHINE DYE COMPOUND

FIELD OF THE INVENTION

The present invention relates to a dye-forming coupler to form an azomethine dye, upon a coupling-reaction with an oxidized product of a developing agent. The present invention also relates to a silver halide photographic light-sensitive material containing the coupler. Further, the present invention relates to an azomethine dye compound, which can be produced by using the above-mentioned coupling reaction.

BACKGROUND OF THE INVENTION

In a silver halide photographic light-sensitive material (hereinafter sometimes referred to simply as "light-sensitive material") for subtractive color photography, a color image is formed by dyes of three primary colors of yellow, magenta and cyan. In the color photography that uses the current p-phenylenediamine-series color-developing agent, an acylacetoanilide-series compound is used as a yellow coupler. However, the hue of the yellow dye obtained from the yellow coupler is tinted with red, due to inferior sharpness at the foot portion of a peak in interest of the absorption curve at the longer wavelength side (that is, on the absorption curve, the peak in interest has subsidiary absorption at its foot portion at the longer wavelength side), which renders it difficult to obtain a yellow hue of high-purity. Further, there is the problem that, due to the low molecular extinction coefficient of the yellow dyes, large amounts of both the coupler and silver halide are needed to obtain a desired colored density. Therefore, sometimes it results in increasing film thickness of the light-sensitive material, and this consequently reduces the sharpness of the obtained color image. Further, the above-mentioned yellow dyes, which are easily decomposed under the conditions of high temperature and high humidity, or the conditions of light irradiation, have insufficient image stability after development processing. Consequently, improvement of these problems is desired.

In order to solve such problems, the acyl group and the anilido group were improved. Recently, as improved couplers of the conventional acylacetanilide-series, there are proposed, for example, 1-alkylcyclopropanecarbonylacetanilide-series compounds, as described in JP-A-4-218,042 ("JP-A" means unexamined published Japanese patent application); cyclomalonic acid diamide-type couplers, as described in JP-A-5-11416; pyrrole-2 or 3-yl- or indole-2 or 3-yl-carbonylacetanilide-series couplers, as described, for example, in European Patent Nos. 953870A1, 953871A1, 953872A1, 953873A1, 953874A1 and 953875A1. The dyes formed from these couplers were improved in terms of both hue and a molecular extinction coefficient, compared with the conventional ones. However, they are still deficient in image stability. Further, owing to their complicated chemical structure, the synthesis route became longer, and consequently cost of the couplers became higher, causing a practical problem.

Further, U.S. Pat. No. 5,455,149 proposes acetoanilide-series couplers to which N-alkyl-4-pyrimidone is bonded. However, dyes obtained from these couplers are still inferior in hue, especially sharpness at the foot portion of a peak of the absorption curve at the longer wavelength side. Further, they are insufficient in fastness to light. Therefore, there is a need to improve these problems.

SUMMARY OF THE INVENTION

The present invention is a dye-forming coupler represented by the following formula (I):

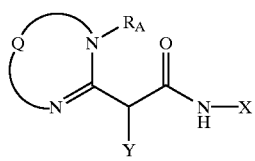

formula (I)

wherein Q represents a residue that forms, together with the —N—C=N— moiety, a nitrogen-containing 6-membered ring; $R_A$ represents an aryl group, a heterocyclic group, or an —$(R_1)_r$—$(R_4)_m$ group; X represents an aryl group; Y represents a hydrogen atom, or a group that is capable of being split-off upon a coupling reaction with an oxidized product of a developing agent:

wherein, when $R_A$ represents an —$(R_1)_r$—$(R_4)_m$ group, $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combined together to form a multiple bond, or alternatively $R_4$s may bond with each other to form a ring, when m is 2 or more; and the —$(R_1)_r$—$(R_4)_m$ group does not represent a straight-chain alkyl group.

Further, the present invention is a silver halide photographic light-sensitive material, which comprises at least one dye-forming coupler represented by the above formula (I).

Still further, the present invention is an azomethine dye compound represented by the following formula (II):

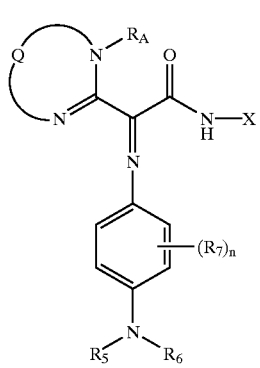

formula (II)

wherein Q represents a residue that forms, together with the —N—C=N— moiety, a nitrogen-containing 6-membered ring; $R_A$ represents an aryl group, a heterocyclic group, or an —$(R_1)_r$—$(R_4)_m$ group; X represents an aryl group:

wherein, when $R_A$ represents an —$(R_1)_r$—$(R_4)_m$ group, $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combine together to form a multiple bond, or alternatively $R_4$s may bond with each other to form a ring, when m is 2 or more; and the —$(R_1)_r$—$(R_4)_m$ group does not represent a straight-chain alkyl group;

$R_5$ and $R_6$ each represent a hydrogen atom or a substituent, or $R_5$ and $R_6$ may bond with each other to form a ring; $R_7$ represents a hydrogen atom or a substituent; n represents 0 (zero) or an integer of 1 to 4, with the proviso that $R_7$s may be the same or different independently, or $R_7$s may bond with each other to form a condensed ring, when n is 2 or more; or $R_7$ may bond with $R_5$ or $R_6$ to form a condensed ring, when n is 1 or more.

Other and further features and advantages of the invention will appear more fully from the following description.

DETAILED DESCRIPTION OF THE INVENTION

According to the present invention, there is provided the following means:

(1) A dye-forming coupler represented by formula (I):

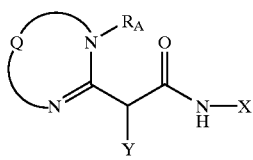

formula (I)

wherein Q represents a residue that forms, together with the —N—C=N— moiety, a nitrogen-containing 6-membered ring; $R_A$ represents an aryl group, a heterocyclic group, or an —$(R_1)_r$—$(R_4)_m$ group; X represents an aryl group; Y represents a hydrogen atom, or a group that is capable of being split-off upon a coupling reaction with an oxidized product of a developing agent:

wherein, when $R_A$ represents an —$(R_1)_r$—$(R_4)_m$ group, $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combined together to form a multiple bond, or alternatively $R_4$s may bond with each other to form a ring, when m is 2 or more; and the —$(R_1)_r$—$(R_4)_m$ group does not represent a straight-chain alkyl group.

(2) The dye-forming coupler according to the above item (1), wherein the dye-forming coupler represented by formula (I) is represented by formula (IA):

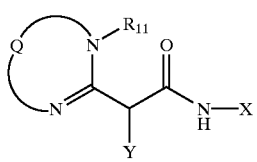

formula (IA)

wherein Q represents a residue that forms, together with the —N—C=N— moiety, a nitrogen-containing 6-membered ring; $R_{11}$ represents an aryl group or a heterocyclic group; X represents an aryl group; Y represents a hydrogen atom, or a group that is capable of being split-off upon a coupling reaction with an oxidized product of a developing agent.

(3) The dye-forming coupler according to the above item (2), wherein in the dye-forming coupler represented by formula (IA), Q is a residue that forms, together with the —N—C=N— moiety, a 4-pyrimidone ring.

(4) The dye-forming coupler according to the above item (2), wherein, in the dye-forming coupler represented by formula (IA), Q is represented by —C(—$R_2$)=C(—$R_3$)—CO—, in which $R_2$ and $R_3$ bond with each other, to form, together with the —C=C— moiety, a 5- to 7-membered ring; or $R_2$ and $R_3$ each independently represent a hydrogen atom or a substituent.

(5) The dye-forming coupler according to the above item (2), wherein, in the dye-forming coupler represented by formula (IA), Q is represented by —C(—$R_2$)=C(—$R_3$)—CO—, in which $R_2$ and $R_3$ bond with each other to form, together with the —C=C— moiety, a benzene ring.

(6) The dye-forming coupler according to the above item (1), wherein the dye-forming coupler represented by formula (I) is represented by the following formula (IB):

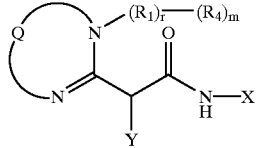

formula (IB)

wherein Q represents a residue that forms, together with the —N—C=N— moiety, a nitrogen-containing 6-membered ring; $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combined together to form a multiple bond, or alternatively $R_4$s may bond with each other to form a ring, when m is 2 or more; X represents an aryl group; Y represents a hydrogen atom, or a group that is capable of being split-off upon a coupling reaction with an oxidized product of a developing agent; and the —$(R_1)_r$—$(R_4)_m$ group does not represent a straight-chain alkyl group.

(7) The dye-forming coupler according to the above item (6), wherein, in the dye-forming coupler represented by formula (IB), Q is a residue that forms, together with the —N—C=N— moiety, a 4-pyrimidone ring.

(8) The dye-forming coupler according to the above item (6), wherein, in the dye-forming coupler represented by formula (IB), Q is represented by —C(—$R_2$)=C(—$R_3$)—CO—, in which $R_2$ and $R_3$ bond with each other, to form, together with the —C=C— moiety, a 5- to 7-membered ring; or $R_2$ and $R_3$ each independently represent a hydrogen atom or a substituent.

(9) The dye-forming coupler according to the above item (6), wherein, in the dye-forming coupler represented by formula (IB), Q is represented by —C(—$R_2$)=C(—$R_3$)—CO—, in which $R_2$ and $R_3$ bond with each other, to form, together with the —C=C— moiety, a benzene ring.

(10) The dye-forming coupler according to any one of the above items (6) to (9), wherein, in the dye-forming coupler represented by formula (IB), $R_4$ is a group selected from the group consisting of an alkyl group, an alkenyl group, an aryl group, a heterocyclic group, a halogen atom, an amino group, a hydroxyl group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, a cyano group, an alkoxy group and an aryloxy group.

(11) The dye-forming coupler according to any one of the above items (6) to (9), wherein, in the dye-forming coupler represented by formula (IB), $R_4$ is a group selected from the group consisting of an aryl group, an alkoxy group and an aryloxy group.

(12) The dye-forming coupler according to any one of the above items (6) to (11), wherein, in the dye-forming coupler represented by formula (IB), r is an integer of 1 to 6.

(13) The dye-forming coupler according to any one of the above items (6) to (12), wherein, in the dye-forming coupler represented by formula (IB), at least one $R_4$ bonds with a carbon atom at at least one α- to δ-positions in the $(R_1)_r$.

(14) A silver halide photographic light-sensitive material, comprising at least one dye-forming coupler represented by formula (I):

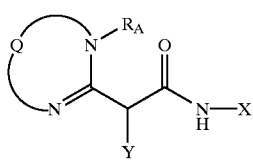

formula (I)

wherein Q represents a residue that forms, together with the —N═C═N— moiety, a nitrogen-containing 6-membered ring; $R_A$ represents an aryl group, a heterocyclic group, or an —$(R_1)_r$—$(R_4)_m$ group; X represents an aryl group; Y represents a hydrogen atom, or a group that is capable of being split-off upon a coupling reaction with an oxidized product of a developing agent:

wherein, when $R_A$ represents an —$(R_1)_r$—$(R_4)_m$ group, $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combined together to form a multiple bond, or alternatively $R_4$s may bond with each other to form a ring, when m is 2 or more; and the —$(R_1)_r$—$(R_4)_m$ group does not represent a straight-chain alkyl group.

(15) The silver halide photographic light-sensitive material according to the above item (14), wherein the dye-forming coupler represented by formula (I) is represented by formula (IA):

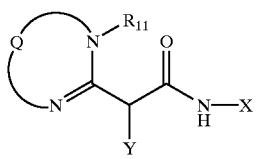

formula (IA)

wherein Q represents a residue that forms, together with the —N═C═N— moiety, a nitrogen-containing 6-membered ring; $R_{11}$ represents an aryl group or a heterocyclic group; X represents an aryl group; Y represents a hydrogen atom, or a group that is capable of being split-off upon a coupling reaction with an oxidized product of a developing agent.

(16) The silver halide photographic light-sensitive material according to the above item (15), wherein, in the dye-forming coupler represented by formula (IA), Q is a residue that forms, together with the —N═C═N— moiety, a 4-pyrimidone ring.

(17) The silver halide photographic light-sensitive material according to the above item (15), wherein, in the dye-forming coupler represented by formula (IA), Q is represented by —C(—$R_2$)═C(—$R_3$)—CO—, in which $R_2$ and $R_3$ bond with each other, to form, together with the —C═C— moiety, a 5- to 7-membered ring; or $R_2$ and $R_3$ each independently represent a hydrogen atom or a substituent.

(18) The silver halide photographic light-sensitive material according to the above item (15), wherein, in the dye-forming coupler represented by formula (IA), Q is represented by —C(—$R_2$)═C(—$R_3$)—CO—, in which $R_2$ and $R_3$ bond with each other, to form, together with the —C═C— moiety, a benzene ring.

(19) The silver halide photographic light-sensitive material according to the above item (14), wherein the dye-forming coupler represented by formula (I) is represented by the following formula (IB):

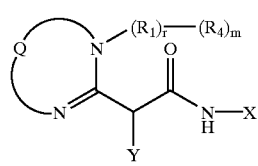

formula (IB)

wherein Q represents a residue that forms, together with the —N═C═N— moiety, a nitrogen-containing 6-membered ring; $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combined together to form a multiple bond, or alternatively $R_4$s may bond with each other to form a ring, when m is 2 or more; X represents an aryl group; Y represents a hydrogen atom, or a group that is capable of being split-off upon a coupling reaction with an oxidized product of a developing agent; and the —$(R_1)_r$—$(R_4)_m$ group does not represent a straight-chain alkyl group.

(20) The silver halide photographic light-sensitive material according to the above item (19), wherein, in the dye-forming coupler represented by formula (IB), Q is a residue that forms, together with the —N═C═N— moiety, a 4-pyrimidone ring.

(21) The silver halide photographic light-sensitive material according to the above item (19), wherein, in the dye-forming coupler represented by formula (IB), Q is represented by —C(—$R_2$)═C(—$R_3$)—CO—, in which $R_2$ and $R_3$ bond with each other, to form, together with the —C═C— moiety, a 5- to 7-membered ring; or $R_2$ and $R_3$ each independently represent a hydrogen atom or a substituent.

(22) The silver halide photographic light-sensitive material according to the above item (19), wherein, in the dye-forming coupler represented by formula (IB), Q is represented by —C(—$R_2$)═C(—$R_3$)—CO—, in which $R_2$ and $R_3$ bond with each other, to form, together with the —C═C— moiety, a benzene ring.

(23) The silver halide photographic light-sensitive material according to any one of the above items (19) to (22), wherein, in the dye-forming coupler represented by formula (IB), $R_4$ is a group selected from the group consisting of an alkyl group, an alkenyl group, an aryl group, a heterocyclic group, a halogen atom, an amino group, a hydroxyl group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, a cyano group, an alkoxy group and an aryloxy group.

(24) The silver halide photographic light-sensitive material according to any one of the above items (19) to (22), wherein, in the dye-forming coupler represented by formula (IB), $R_4$ is a group selected from the group consisting of an aryl group, an alkoxy group and an aryloxy group.

(25) The silver halide photographic light-sensitive material according to any one of the above items (19) to (24), wherein, in the dye-forming coupler represented by formula (IB), r is an integer of 1 to 6.

(26) The silver halide photographic light-sensitive material according to any one of the above items (19) to (25), wherein, in the dye-forming coupler represented by formula (IB), at least one $R_4$ bonds with a carbon atom at at least one α- to δ-positions in the $(R_1)_r$.

(27) An azomethine dye compound represented by formula (II):

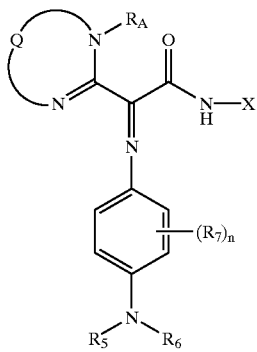

formula (II)

wherein Q represents a residue that forms, together with the —N—C=N— moiety, a nitrogen-containing 6-membered ring; $R_A$ represents an aryl group, a heterocyclic group, or an —$(R_1)_r$—$(R_4)_m$ group; X represents an aryl group:

wherein, when $R_A$ represents an —$(R_1)_r$—$(R_4)_m$ group, $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combine together to form a multiple bond, or alternatively $R_4$s may bond with each other to form a ring, when m is 2 or more; and the —$(R_1)_r$—$(R_4)_m$ group does not represent a straight-chain alkyl group;

$R_5$ and $R_6$ each represent a hydrogen atom or a substituent, or $R_5$ and $R_6$ may bond with each other to form a ring; $R_7$ represents a hydrogen atom or a substituent; n represents 0 (zero) or an integer of 1 to 4, with the proviso that $R_7$s may be the same or different independently, or $R_7$s may bond with each other to form a condensed ring, when n is 2 or more; or $R_7$ may bond with $R_5$ or $R_6$ to form a condensed ring, when n is 1 or more.

(28) The azomethine dye compound according to the above item (27), wherein the azomethine dye compound represented by formula (II) is represented by the following formula (IIA):

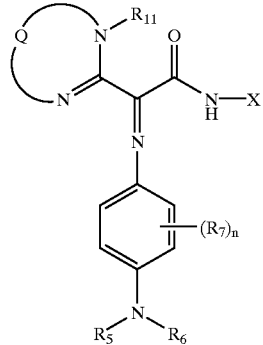

formula (IIA)

wherein Q represents a residue that forms, together with the —N—C=N— moiety, a nitrogen-containing 6-membered ring; $R_{11}$ represents an aryl group or a heterocyclic group; X represents an aryl group; $R_5$ and $R_6$ each represent a hydrogen atom or a substituent, or $R_5$ and $R_6$ may bond with each other to form a ring; $R_7$ represents a hydrogen atom or a substituent; n represents 0 (zero) or an integer of 1 to 4, with the proviso that $R_7$s may be the same or different independently, or $R_7$s may bond with each other to form a condensed ring, when n is 2 or more; or $R_7$ may bond with $R_5$ or $R_6$ to form a condensed ring, when n is 1 or more.

(29) The azomethine dye compound according to the above item (28), wherein, in the azomethine dye compound represented by formula (IIA), Q is a residue that forms, together with the —N—C=N— moiety, a 4-pyrimidone ring.

(30) The azomethine dye compound according to the above item (28), wherein, in the azomethine dye compound represented by formula (IIA), Q is represented by —C(—$R_2$)=C(—$R_3$)—CO—, in which $R_2$ and $R_3$ bond with each other, to form, together with the —C=C— moiety, a 5- to 7-membered ring; or $R_2$ and $R_3$ each independently represent a hydrogen atom or a substituent.

(31) The azomethine dye compound according to the above item (28), wherein, in the azomethine dye compound represented by formula (IIA), Q is represented by —C(—$R_2$)=C(—$R_3$)—CO—, in which $R_2$ and $R_3$ bond with each other to form, together with the —C=C— moiety, a benzene ring.

(32) The azomethine dye compound according to the above item (27), wherein the azomethine dye compound represented by formula (II) is represented by the following formula (IIB):

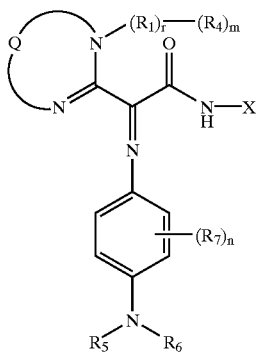

formula (IIB)

wherein Q represents a residue that forms, together with the —N—C=N— moiety, a nitrogen-containing 6-membered ring; $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combine together to form a multiple bond, or alternatively $R_4$s may bond with each other to form a ring, when m is 2 or more; X represents an aryl group; and the —$(R_1)_r$—$(R_4)_m$ group does not represent a straight-chain alkyl group; $R_5$ and $R_6$ each represent a hydrogen atom or a substituent, or $R_5$ and $R_6$ may bond with each other to form a ring; $R_7$ represents a hydrogen atom or a substituent; n represents 0 (zero) or an integer of 1 to 4, with the proviso that, $R_7$s may be the same or different independently, or $R_7$s may bond with each other to form a condensed ring, when n is 2 or more; or $R_7$s may bond with $R_5$ or $R_6$ to form a condensed ring, when n is 1 or more.

(33) The azomethine dye compound according to the above item (32), wherein, in the azomethine dye compound represented by formula (IIB), Q is a residue that forms, together with the —N—C=N— moiety, a 4-pyrimidone ring.

(34) The azomethine dye compound according to the above item (32), wherein, in the azomethine dye compound represented by formula (IIB), Q is represented by —C(—$R_2$)=C(—$R_3$)—CO—, in which $R_2$ and $R_3$ bond with each other, to form, together with the —C=C— moiety, a 5- to 7-membered ring; or $R_2$ and $R_3$ each independently represent a hydrogen atom or a substituent.

(35) The azomethine dye compound according to the above item (32), wherein, in the azomethine dye compound represented by formula (IIB), Q is represented by —C(—$R_2$)=C(—$R_3$)—CO—, in which $R_2$ and $R_3$ bond with each other to form, together with the —C=C— moiety, a benzene ring.

(36) The azomethine dye compound according to any one of the above items (32) to (35), wherein, in the azomethine dye compound represented by formula (IIB), $R_4$ is a group selected from the group consisting of an alkyl group, an alkenyl group, an aryl group, a heterocyclic group, a halogen atom, an amino group, a hydroxyl group, a carboxyl group, a sulfo group, an acylamino group, an alkyl- or an aryl-sulfonylamino group, a carbamoyl group, a sulfamoyl group, an acyl group, a sulfonyl group, an alkoxycarbonyl group, an aryloxycarbonyl group, an alkylthio group, an arylthio group, a cyano group, an alkoxy group and an aryloxy group.

(37) The azomethine dye compound according to any one of the above items (32) to (35), wherein, in the azomethine dye compound represented by formula (IIB), $R_4$ is a group selected from the group consisting of an aryl group, an alkoxy group and an aryloxy group.

(38) The azomethine dye compound according to any one of the above items (32) to (37), wherein, in the azomethine dye compound represented by formula (IIB), r is an integer of 1 to 6.

(39) The azomethine dye compound according to any one of the above items (32) to (38), wherein, in the azomethine dye compound represented by formula (IIB), at least one $R_4$ bonds with a carbon atom at at least one α- to δ-positions in the $(R_1)_r$.

The above-mentioned items (4), (5), (7) to (12), (17), (18), (20) to (25), (30), (31), and (33) to (38) are preferable embodiments of the present invention.

Herein, the dye-forming coupler represented by formula (IA) (e.g. those described in the above items (2) to (5)), and the light-sensitive material, which utilizes the compound of formula (IA), (e.g. those described in the above items (15) to (18)), and the azomethine dye compound represented by formula (IIA), which is produced from the dye-forming coupler of formula (IA), (e.g. those described in the above items (28) to (31)), are collectively referred to as a first embodiment of the present invention.

Further, herein, the dye-forming coupler represented by formula (IB) (e.g. those described in the above items (6) to (13)), and the light-sensitive material, which utilizes the compound of formula (IB), (e.g. those described in the above items (19) to (26)), and the azomethine dye compound represented by formula (IIB), which is produced from the dye-forming coupler of formula (IB), (e.g. those described in the above items (32) to (39)), are collectively referred to as a second embodiment of the present invention.

Herein, the present invention means to include both the first embodiment and the second embodiment, unless otherwise specified.

The present invention is explained in detail below.

Dye-forming Coupler

First, the compound represented by formula (IA) of the present invention, among the compound represented by the aforementioned formula (I) (herein they are also referred to as a dye-forming coupler) of the present invention are explained in detail.

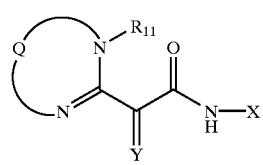

formula (IA)

In formula (IA), $R_{11}$ represents an aryl group or a heterocyclic group.

The aryl group is preferably a substituted or unsubstituted, and monocyclic or condensed aryl group having 6 to 30 carbon atoms, e.g., phenyl, p-tolyl, naphthyl, m-chlorophenyl, and o-hexadecanoylaminophenyl groups. The heterocyclic group is preferably a 5- to 7-membered substituted or unsubstituted, saturated or unsaturated, aromatic or non-aromatic, and monocyclic or condensed heterocyclic group having 3 to 30 carbon atoms; more preferably a heterocyclic group having ring-constituting atoms selected from carbon, nitrogen and sulfur atoms, the heterocyclic group containing at least one hetero atom selected from the group consisting of a nitrogen atom, an oxygen atom and a sulfur atom; and furthermore preferably a 5- to 6-membered aromatic heterocyclic group; e.g., 2-furyl, 2-thienyl, 2-pyridyl, 4-pyridyl, 2-pyrimidinyl, and 2-benzothiazolyl groups.

$R_{11}$ is preferably a phenyl group.

Examples of the substituent of the substituted aryl and the substituted heterocyclic groups (i.e., the substituent that $R_{11}$ may have) include a halogen atom, an alkyl group (including a cycloalkyl group and a bicycloalkyl group), an alkenyl group (including a cycloalkenyl group and a bicycloalkenyl group), an alkynyl group, an aryl group, a herocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an alkylamino group and an anilino group), an acylamino group, an aminocarbonylamino group, an alkoxycarbonylamino group, an aryloxycarbonylamino group, a sulfamoylamino group, an alkyl- or an aryl-sulfonylamino group, a mercapto group, an alkylthio group, an arylthio group, a heterocyclic thio group, a sulfamoyl group, a sulfo group, an alkyl- or aryl-sulfinyl group, an alkyl- or aryl-sulfonyl group, an acyl group, an aryloxycarbonyl group, an alkoxycarbonyl group, a carbamoyl group, an aryl- or heterocyclic-azo group, an imido group, a phosphino group, a phosphinyl group, a phosphinyloxy group, a phosphinylamino group and a silyl group.

In case where $R_{11}$ is substituted with two or more substituents, these substituents may be the same or different independently, or the substituents adjacent to each other may combine together to form a ring, preferably a 5- to 6-membered, saturated or unsaturated ring.

The above-said substituent may be further substituted with a substituent. Examples of the substituent are those as enumerated above.

Examples of the substituent which $R_{11}$ may have are further explained below.

Examples of these substituents include a halogen atom (e.g., chlorine, bromine, iodine); an alkyl group (preferably a straight-chain or branched-chain and substituted or unsubstituted alkyl group, more preferably the alkyl group having 1 to 30 carbon atoms, e.g., methyl, ethyl, n-propyl, isopropyl, t-butyl, n-octyl, eicosyl, 2-chloroethyl, 2-cyanoethyl, 2-ethylhexyl); a cycloalkyl group (preferably a substituted or unsubstituted monocyclic cycloalkyl group having 3 to 30 carbon atoms, e.g., cyclohexyl, cyclopentyl, and 4-n-dodecyl cyclohexyl, and a polycycloalkyl group including groups composed of a polycyclic structure such as a bicycloalkyl group (preferably a substituted or unsubstituted bicycloalkyl group having 5 to 30 carbon atoms, e.g., bicyclo[1,2,2]heptane-2-yl and bicyclo[2,2,2]octane-3-yl), and a tricycloalkyl group; more preferably a monocycloalkyl group or bicycloalkyl group and particularly preferably a monocyclic cycloalkyl group); an alkenyl group (preferably a straight-chain or branched-chain, and substituted or unsubstituted alkenyl group, more preferably the alkenyl group having 2 to 30 carbon atoms, e.g., vinyl, allyl, prenyl, geranyl, oleyl); a cycloalkenyl group (preferably a substituted or unsubstituted cycloalkenyl group having 3 to 30 carbon atoms, e.g., 2-cyclopentene-1-yl, and 2-cyclohexene-1-yl; and a polycycloalkenyl group such as a bicycloalkenyl group (preferably a substituted or unsubstituted bicycloalkenyl group having 5 to 30 carbon atoms, e.g., bicyclo[2,2,1]hepto-2-ene-1-yl and bicyclo[2,2,2]octo-2-ene-4-yl) and a tricycloalkenyl group, with a monocyclic cycloalkenyl group being particularly preferred); an alkynyl group (preferably a substituted or unsubstituted alkynyl group having 2 to 30 carbon atoms, e.g., ethynyl, propargyl, trimethylsilylethynyl); an aryl group (preferably a substituted or unsubstituted aryl group having 6 to 30 carbon atoms, e.g., phenyl, p-tolyl, naphthyl, m-chlorophenyl, o-hexadecanoylaminophenyl); a heterocyclic group (preferably a 5- to 7-membered substituted or unsubstituted, saturated or unsaturated, aromatic or non-aromatic, and monocyclic or condensed heterocyclic group, more preferably a heterocyclic group having ring-constituting atoms selected from carbon, nitrogen and sulfur atoms, the heterocyclic group containing at least one hetero atom selected from the group consisting of nitrogen, oxygen and sulfur atoms; furthermore preferably a 5- to 6-membered aromatic heterocyclic group having 3 to 30 carbon atoms, e.g., 2-furyl, 2-thienyl, 2-pyridyl, 4-pyridyl, 2-pyrimidinyl, 2-benzothiazolyl); a cyano group; a hydroxyl group; a nitro group; a carboxyl group; an alkoxy group (preferably a substituted or unsubstituted alkoxyl group having 1 to 30 carbon atoms, e.g., methoxy, ethoxy, isopropoxy, t-butoxy, n-octyloxy, 2-methoxyethoxy); an aryloxy group (preferably a substituted or unsubstituted aryloxy group having 6 to 30 carbon atoms, e.g., phenoxy, 2-methylphenoxy, 4-t-buthylphenoxy, 3-nitrophenoxy, 2-tetradecanoylaminophenoxy); a silyloxy group (preferably a silyloxy group having 3 to 20 carbon atoms, e.g., trimethylsilyloxy, t-butyldimethylsilyloxy); a herocyclic oxy group (preferably a substituted or unsubstituted heterocyclic oxy group having 2 to 30 carbon atoms, more preferably those having the heterocyclic moiety as described to explain the above-mentioned heterocyclic group, e.g., 1-phenyltetrazole-5-oxy, 2-tetrahydropyranyloxy); an acyloxy group (preferably formyloxy, a substituted or unsubstituted alkylcarbonyloxy group having 2 to 30 carbon atoms or a substituted or unsubstituted arylcarbonyloxy group having 6 to 30 carbon atoms, e.g., formyloxy, acetyloxy, pivaloyloxy, stealoyloxy, benzoyloxy, p-methoxyphenylcarbonyloxy); a carbamoyloxy group (preferably a substituted or unsubstituted carbamoyloxy group having 1 to 30 carbon atoms, e.g., N,N-dimethylcarbamoyloxy, N,N-diethylcarbamoyloxy, morpholinocarbonyloxy, N,N-di-n-octylaminocarbonyloxy, N-n-octylcarbamoyl oxy); an alkoxycarbonyloxy group (preferably a substituted or unsubstituted alkoxycarbonyloxy group having 2 to 30 carbon atoms, e.g., methoxycarbonyloxy, ethoxycarbonyloxy, t-butoxy carbonyloxy, n-octylcarbonyloxy); an aryloxycarbonyloxy group (preferably a substituted or unsubstituted aryloxycarbonyloxy group having 7 to 30 carbon atoms, e.g., phenoxycarbonyloxy, p-methoxyphenoxycarbonyloxy, p-n-hexadecyloxyphenoxycarbonyloxy); an amino group (preferably an unsubstituted amino group, a substituted or unsubstituted alkylamino group having 1 to 30 carbon atoms, a substituted or unsubstituted arylamino group having 6 to 30 carbon atoms, and a heterocyclic amino group having 0 (zero) to 30 carbon atoms, e.g., amino, methylamino, dimethylamino, anilino, N-methyl-anilino, diphenylamino, N-1,3,5-triazine-2-il amino); an acylamino group (preferably a formylamino group, a substituted or unsubstituted alkylcarbonylamino group having 1 to 30 carbon atoms, and a substituted or unsubstituted arylcarbonylamino group having 6 to 30 carbon atoms, e.g., formylamino, acetylamino, pivaloylamino, lauroylamino, benzoylamino, and 3,4,5-tri-n-octyloxyphenylcarbonylamino); an aminocarbonylamino group (preferably a substituted or unsubstituted aminocarbonylamino group having 1 to 30 carbon atoms, e.g., carbamoylamino, N,N-dimethylaminocarbonylamino, N,N-diethylamino carbonylamino, morpholinocarbonylamino); an alkoxycarbonylamino group (preferably a substituted or unsubstituted alkoxycarbonylamino group having 2 to 30 carbon atoms, e.g., methoxycarbonylamino, ethoxycarbonylamino, t-butoxycarbonylamino, n-octadecyloxycarbonylamino, N-methyl-methoxycarbonylamino); an aryloxycarbonylamino group (preferably a substituted or unsubstituted aryloxycarbonylamino group having 7 to 30 carbon atoms, e.g., phenoxycarbonylamino, p-chlorophenoxycarbonylamino, m-n-octyloxyphenoxycarbonyl amino); a sulfamoyl amino group (preferably a substituted or unsubstituted sulfamoylamino group having 0 (zero) to 30 carbon atoms, e.g., sulfamoylamino, N,N-dimethylaminosulfonylamino, N-n-octyl aminosulfonylamino); an alkyl- or aryl-sulfonylamino group (preferably a substituted or unsubstituted alkyl sulfonylamino group having 1 to 30 carbon atoms and a substituted or unsubstituted aryl sulfonylamino group having 6 to 30 carbon atoms, e.g., methyl sulfonylamino, butylsulfonylamino, phenylsulfonylamino, 2,3,5-trichlorophenylsulfonylamino, p-methylphenylsulfonylamino); a mercapto group; an alkylthio group (preferably a substituted or unsubstituted alkylthio group having 1 to 30 carbon atoms, e.g., methylthio, ethylthio, n-hexadecylthio); an arylthio group (preferably a substituted or unsubstituted arylthio group having 6 to 30 carbon atoms, e.g., phenylthio, p-chlorophenylthio, m-methoxyphenylthio); a heterocyclic thio group (preferably a substituted or unsubstituted heterocyclic thio group having 2 to 30 carbon atoms in which the heterocyclic moiety is preferably the same as that of the above-described heterocyclic group, e.g., 2-benzothiazolylthio, 1-phenyltetrazol-5-ylthio); a sulfamoyl group (preferably a substituted or unsubstituted sulfamoyl group having 0 (zero) to 30 carbon atoms, e.g., N-ethylsulfamoyl, N-(3-dodecyloxypropyl)sulfamoyl, N,N-dimethylsulfamoyl, N-acetylsulfamoyl, N-benzoylsulfamoyl, N-(N'-phenylcarbamoyl)sulfamoyl); a sulfo group; an alkyl- or aryl-sulfinyl group (preferably a substituted or unsubstituted alkylsulfinyl group having 1 to 30 carbon atoms and a substituted or unsubstituted arylsulfinyl group having 6 to 30 carbon atoms, e.g., methylsulfinyl, ethylsulfinyl, phenylsulfinyl, p-methylphenylsulfinyl); an alkyl- or aryl-sulfonyl group (preferably a substituted or unsubstituted alkylsulfonyl group having 1 to 30 carbon atoms and a substituted or unsubstituted arylsulfonyl group having 6 to 30 carbon atoms, e.g., methylsulfonyl, ethylsulfonyl, phenylsulfonyl, p-methylphenylsulfonyl); an acyl group (preferably a formyl group, a substituted or unsubstituted alkylcarbonyl group having 2 to 30 carbon atoms and a substituted or unsubstituted arylcarbonyl group having 7 to 30 carbon atoms, e.g., acetyl, pivaloyl, 2-chloroacetyl, stearoyl, benzoyl, p-n-octyloxyphenylcarbonyl); an aryloxycarbonyl group (preferably a substituted or unsubstituted aryloxycarbonyl group having 7 to 30 carbon atoms, e.g., phenoxycarbonyl, o-chlorophenoxycarbonyl, m-nitrophenoxycarbonyl, p-t-butylphenoxycarbonyl); an alkoxycarbonyl group (preferably a substituted or unsubstituted alkoxycarbonyl group having 2 to 30 carbon atoms, e.g., methoxycarbonyl, ethoxycarbonyl, t-butoxycarbonyl, n-octadecyloxycarbonyl); a carbamoyl group (preferably a substituted or unsubstituted carbamoyl group having 1 to 30 carbon atoms, e.g., carbamoyl, N-methylcarbamoyl, N,N-dimethylcarbamoyl, N,N-di-n-octylcarbamoyl, N-(methylsulfonyl)carbamoyl); an aryl- or heterocyclic-azo group (preferably a substituted or unsubstituted aryl azo group having 6 to 30 carbon atoms, and a substituted or unsubstituted heterocyclic azo group having 3 to 30 carbon atoms in which the heterocyclic part is preferably the same as that of the above-described heterocyclic group, e.g., phenylazo, p-chlorophenylazo, 5-ethylthio-1,3,4-thiadiazole-2-yl azo); an imido group (preferably a substituted or unsubstituted imido group having 2 to 30 carbon atoms, e.g., N-succinimido, N-phthalimido); a phosphino group (preferably a substituted or unsubstituted phosphino group having 2 to 30 carbon atoms, e.g., dimethylphosphino, diphenylphosphino, methylphenoxyphosphino); a phosphinyl group (preferably a substituted or unsubstituted phosphinyl group having 2 to 30 carbon atoms, e.g., phosphinyl, dioctyloxyphosphinyl, diethoxyphosphinyl); a phosphinyloxy group (preferably a substituted or unsubstituted phosphinyloxy group having 2 to 30 carbon atoms, e.g., diphenoxyphosphinyloxy, dioctyloxyphosphinyloxy); a phosphinylamino group (preferably a substituted or unsubstituted phosphinylamino group having 2 to 30 carbon atoms, e.g., dimethoxyphosphinylamino, dimethylaminophosphinylamino); and a silyl group (preferably a substituted or unsubstituted silyl group having 3 to 30 carbon atoms, e.g., trimethylsilyl, t-butyldimethylsilyl, phenyldimethylsilyl).

Among the substituents that $R_{11}$ may additionally have, a hydrogen atom(s) in the substituents may be replaced with the above-described group. Examples of these groups that $R_{11}$ may additionally have include an alkylcarbonylaminosulfonyl group, an arylcarbonylaminosulfonyl group, an alkylsulfonylaminocarbonyl group, and an arylsulfonyl aminocarbonyl group. As the specific examples, methylsulfonylaminocarbonyl, p-methylphenylsulfonylaminocarbonyl, acetylaminosulfonyl, benzoylaminosulfonyl, ethylcarbonylaminosulfonyl, isopropylcarbonylaminosulfonyl, p-methanesulfonylphenylcarbonylaminosulfonyl, dodecylsulfonylaminocarbonyl, and p-chlorophenylsulfonylaminocarbonyl group are enumerated.

Further, the substituents adjacent to each other may combine together to form a ring, preferably a 5- to 7-membered saturated or unsaturated ring, and the ring may be alicyclic, aromatic or heterocyclic ring. As a example of the ring, benzene, furan, thiophene, cyclopentane, and cyclohexane rings are enumerated.

Each of these substituents and the rings that are formed by bonding of these substituents with each other, may further have a substituent thereon, such as those enumerated as the substituent that the above-mentioned $R_{11}$ may have.

The total carbon atom of the substituent that the aryl group or the heterocyclic group of $R_{11}$ may have, is preferably 2 to 50, more preferably 8 to 45, and furthermore preferably 15 to 40.

Preferred example of these substituents is an alkyl group, an alkenyl group, an aryl group, a heterocyclic group, a halogen atom, an alkoxy group, an aryloxy group, an alkylthio group, an arylthio group, a cyano group, an acylamino group, an alkyl- or aryl-sulfonylamino group, an alkoxycarboxyl group, a carbamoyl group, a sulfamoyl group, an alkylamino group or an arylamino group.

In formula (IA), Q represents a residue that forms, together with the —N—C=N— moiety, a nitrogen-containing 6-membered heterocyclic ring. The nitrogen-containing heterocyclic ring is a substituted or unsubstituted heterocyclic ring, more preferably a heterocyclic ring composed of a carbon atom and a nitrogen atom, as ring-forming atoms, and having 2 to 4 nitrogen atoms; furthermore preferably a nitrogen-containing 6-membered heterocyclic ring having 2 to 30 carbon atoms and 2 nitrogen atoms. Examples of the nitrogen-containing 6-membered ring that is formed by Q together with the —N—C=N— moiety, include 4-pyrimidone, 1,3-diazine-4,6-dione, 1,3,5-triazine-2-one and 1,2,4-triazine-5-one. The nitrogen-containing 6-membered ring that is formed by Q together with the —N—C=N— moiety, may have a substituent. Examples of the substituent are the same as those of the substituent, which the above-mentioned $R_{11}$ may have.

Further, the substituents adjacent to each other may combine together to form a ring, and a 5- to 7-membered saturated or unsaturated ring is preferable. The ring may be alicyclic, aromatic or heterocyclic ring. As example of the ring, benzene, furan, thiophene, cyclopentane, and cyclohexane rings are enumerated.

Each of the above-mentioned substituents and the rings that are formed by combination of some of these substituents, also may have a substituent. Examples of the substituent are the same as those of the substituent, which the above-mentioned $R_{11}$ may have.

The total carbon atoms of the above-mentioned substituent is preferably 2 to 50, more preferably 8 to 45, furthermore preferably 15 to 40.

Preferred of these substituents are an alkyl group, an alkenyl group, an aryl group, a heterocyclic group, a halogen atom, an alkoxy group, an aryloxy group, an alkylthio group, an arylthio group, a cyano group, an acylamino group, an alkyl- and aryl-sulfonylamino group, an alkoxycarboxyl group, a carbamoyl group, a sulfamoyl group, an alkylamino group and an arylamino group.

Q is preferably a residue that forms, together with the —N—C=N— moiety, a 4-pyrimidone ring. More preferably Q is represented by —C(—$R_2$)=C(—$R_3$)—CO—. $R_2$ and $R_3$, when combined with each other, forms, together with the —C=C— moiety, a 5- to 7-membered ring, or $R_2$ and $R_3$ each independently represent a hydrogen atom or a substituent. The ring that is formed by combination of $R_2$ and $R_3$ together with the —C=C— moiety, is preferably a 5- to 7-membered alicyclic, aromatic or heterocyclic ring. As example of the ring, benzene, pyrazole, furan, thiophene, cyclopentene and cyclohexene rings are enumerated. More preferably the ring is 6-membered aromatic ring. A benzene ring is most preferred.

When $R_2$ and $R_3$ each represent a substituent, $R_2$ and $R_3$ may be the same or different independently. Examples of the substituent are the same as those of the substituent, which the above-mentioned $R_{11}$ may have.

In formula (IA), X represents an aryl group. The aryl group is preferably a substituted or unsubstituted aryl group having 6 to 30 carbon atoms, such as a phenyl group and a naphthyl group. X may have a substituent. Examples of the substituent are the same as those of the substituent, which the above-mentioned $R_{11}$ may have. Preferable examples of the substituent that X may have, include an alkyl group, an alkenyl group, an aryl group, a heterocyclic group, a halogen atom, an alkoxy group, an aryloxy group, an alkylthio group, an arylthio group, a cyano group, an acylamino group, an alkyl- and aryl-sulfonylamino group, an alkoxy carboxyl group, a carbamoyl group, a sulfamoyl group, an alkylamino group and an arylamino group.

Preferably the carbon atom adjacent to the position of the amido group on the aryl group, bonds with a halogen atom (e.g., fluorine, chlorine), an alkyl group (e.g., methyl), an alkoxy group (e.g., methoxy, isopropyloxy, dodecyloxy), or an aryloxy group (e.g., phenyloxy). Among these groups, a halogen atom and an alkoxy group are more preferred. An alkoxy group is furthermore preferred.

In the coupler of the present invention, X is preferably a phenyl group. Assuming that the position where the phenyl group bonds with the amido group is the 1-position, the phenyl group preferably has the above-mentioned substituent at least at the 2-position, more preferably has the substituents at the 2- and 5-positions.

In formula (IA), Y represents a hydrogen atom, or a group that is capable of being split-off upon a coupling reaction with an oxidized product of a developing agent. Examples of Y include a group that splits off with a nitrogen, oxygen, or sulfur atom (a splitting-off atom) and a halogen atom (e.g., chlorine, bromine).

Examples of the group that splits off with a nitrogen atom, include a heterocyclic group (preferably a 5- to 7-membered substituted or unsubstituted, saturated or unsaturated, aromatic (herein the term "aromatic" is used to embrace a substance that has (4n+2) cyclic conjugated electrons) or non-aromatic, monocyclic or condensed heterocyclic groups, more preferably a 5- to 6-membered heterocyclic group, in which the ring-forming atom is selected from carbon, nitrogen and sulfur atoms and in addition at least one of hetero atoms selected from nitrogen, oxygen and sulfur atoms is incorporated, with specific examples of the heterocyclic ring including succinimide, maleinimide, phthalimide, diglycolimide, pyrrole, pyrazole, imidazole, 1,2,4-triazole, tetrazole, indole, benzopyrazole, benzimidazole, benzotriazole, imidazoline-2,4-dione, oxazolidine-2,4-dione, thiazolidine-2-one, benzimidazoline-2-one, benzoxazoline-2-one, benzothiazoline-2-one, 2-pyrroline-5-one, 2-imidazoline-5-one, indoline-2,3-dione, 2,6-dioxypurine parabanic acid, 1,2,4-triazolidine-3,5-dione, 2-pyridone, 4-pyridone, 2-pyrimidone, 6-pyridazone, 2-pyrazone, 2-amino-1,3,4-thiazolidine-4-one), a carbonamido group (e.g., acetamido, trifluoroacetamido), a sulfonamido group (e.g., methanesulfonamido, benzenesulfonamido), an arylazo group (e.g., phenylazo, naphthylazo), and a carbamoylamino group (e.g., N-methyl carbamoylamino).

Preferred of the group that splits off with a nitrogen atom are heterocyclic groups, more preferably aromatic heterocyclic groups having 1, 2, or 4 ring-forming nitrogen atom(s), or heterocyclic groups represented by the following formula (LA). The heterocyclic groups represented by the following formula (LA) are furthermore preferred.

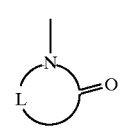

formula (LA)

In the formula (LA), L represents a residue that forms, together with —NC(=O)—, a 5- to 6-membered nitrogen-containing heterocyclic ring.

Examples of the residues are enumerated in the explanation of the above-mentioned heterocyclic group, and such residues as enumerated above are more preferred.

Particularly preferably L is a residue that forms a 5-membered nitrogen-containing heterocyclic ring.

Examples of the group that splits off with an oxygen atom include an aryloxy group (e.g., phenoxy, 1-naphthoxy), a heterocyclic oxy group (e.g., pyridyloxy, pyrazolyloxy), an acyloxy group (e.g., acetoxy, benzoyloxy), an alkoxy group (e.g., methoxy, dodecyloxy), a carbamoyloxy group (e.g., N,N-diethylcarbamoyloxy, morpholinocarbamoyloxy), an aryloxycarbonyloxy group (e.g., phenoxycarbonyloxy), an alkoxycarbonyloxy group (e.g., methoxycarbonyloxy, ethoxycarbonyloxy), an alkylsulfonyloxy group (e.g., methanesulfonyloxy), and an arylsulfonyloxy group (e.g., benzenesulfonyloxy, toluenesulfonyloxy).

Preferred of these groups are an aryloxy group, an acyloxy group and a heterocyclic oxy group.

Examples of the group that splits off with a sulfur atom include an arylthio group (e.g., phenylthio, naphthylthio), a heterocyclic thio group (e.g., tetrazolylthio, 1,3,4-thiadiazolylthio, 1,3,4-oxazolylthio, benzimidazolylthio), an alkylthio group (e.g., methylthio, octylthio, hexadecylthio), an alkylsulfinyl group (e.g., methane sulfinyl), an arylsulfinyl group (e.g., benzenesulfinyl), an arylsulfonyl group (e.g., benzenesulfonyl), and an alkylsulfonyl group (e.g., methanesulfonyl).

Preferred of the group that splits off with a sulfur atom are an arylthio group and a heterocyclic thio group. A heterocyclic thio group is more preferred.

Y may be substituted with a substituent. Examples of the substituent include those enumerated as the substituent, which the above-mentioned $R_{11}$ may have.

Y is preferably the group that splits off with a nitrogen, oxygen, or sulfur atom, more preferably the group that splits off with a nitrogen atom. Further, those as enumerated as the preferable examples of the group that splits off with a nitrogen atom are preferred in the same order as mentioned above. Preferable examples of Y are further explained below. Y is preferably an aromatic heterocyclic group having 1, 2, or 4 ring-forming nitrogen atom(s), or a heterocyclic ring group represented by the above-mentioned formula (LA) (the latter is particularly preferred), a group that splits off with an oxygen atom (particularly preferably aryloxy, acyloxy, heterocyclic oxy) and a group that splits off with a sulfur atom (preferably arylthio, heterocyclic thio, and particularly preferably heterocyclic thio).

Y may be a photographically useful group. As the photographically useful group, a development inhibitor, a desilvering accelerator, a redox compound, a dye, a coupler and the like, or their precursors are enumerated. Y is more preferably a development inhibitor or a precursor thereof. Examples of the development inhibitor or the precursor thereof include those as enumerated in JP-A-2000-17195. Preferable examples are the same as described therein.

In order to render the coupler inmobile in a light-sensitive material, at least one of Q, $R_{11}$, X and Y has preferably 8 to 50 carbon atoms, more preferably 10 to 40 carbon atoms in total respectively, including carbon atoms of substituent(s) that they may have.

Preferable specific examples of the coupler represented by formula (IA) according to the present invention are shown below. However, the present invention should not be construed as being limited to these compounds. The present invention includes tautomers having a hydrogen atom moved on a carbonyl group or a nitrogen-containing 6-membered ring.

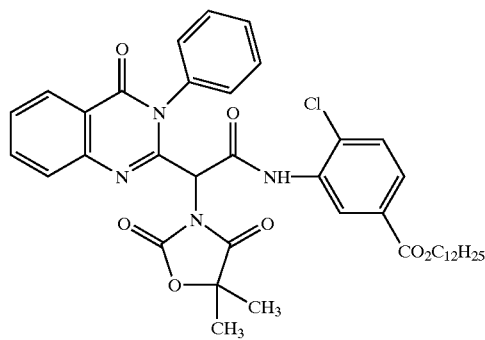

(1)

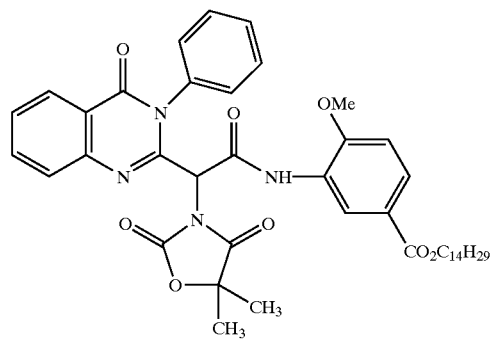

(2)

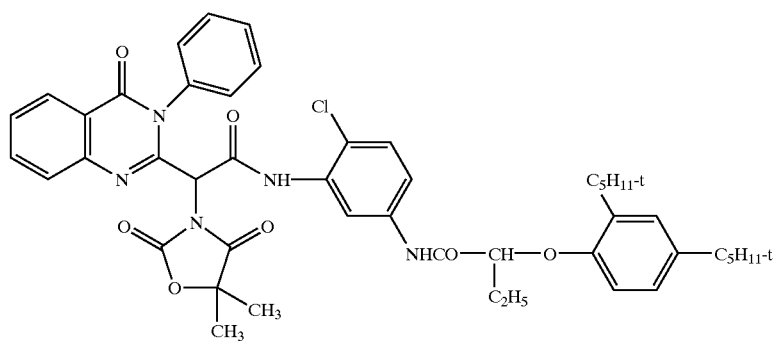

(3)

(4)
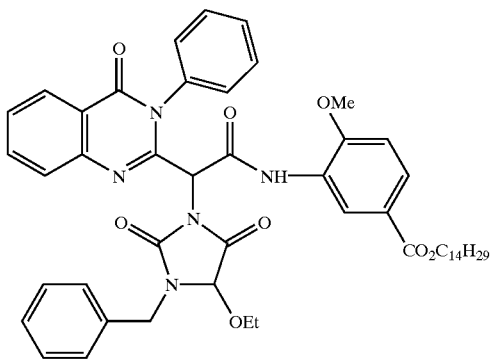
(5)
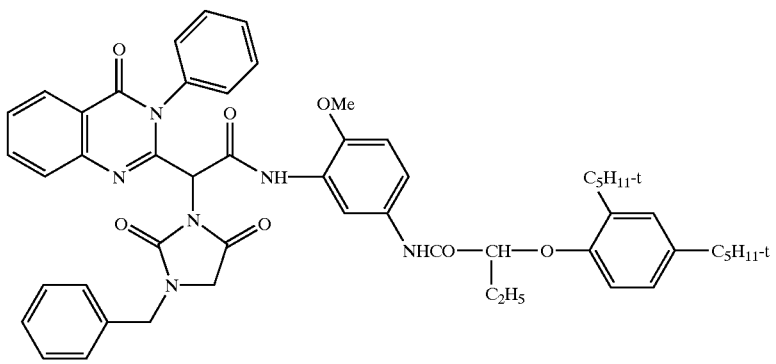
(6)
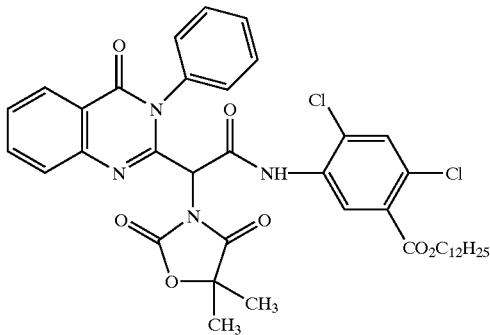
(7)
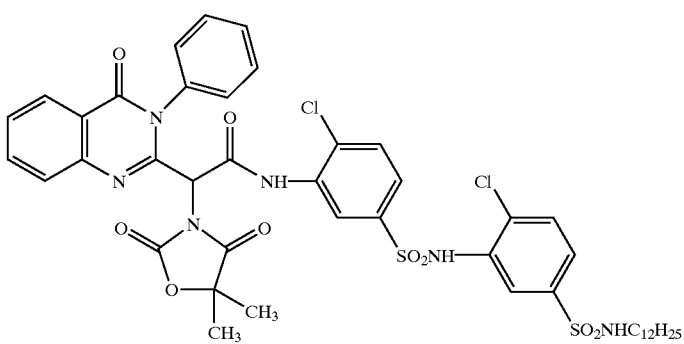

(8)
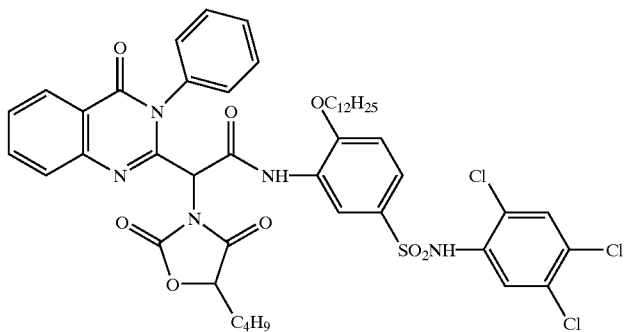
(9)
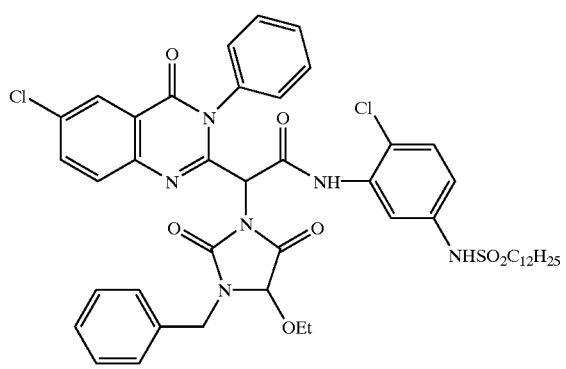
(10)
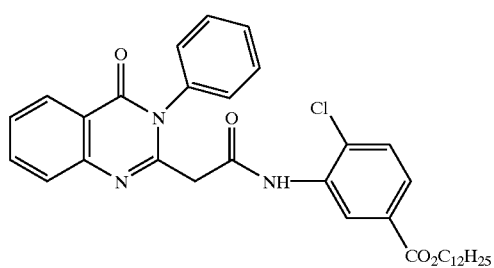
(11)
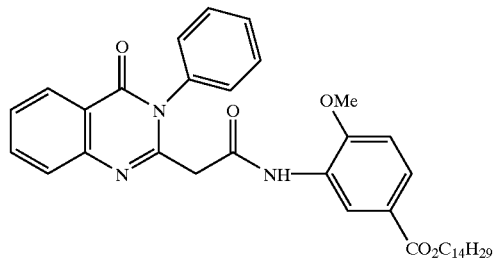
(12)
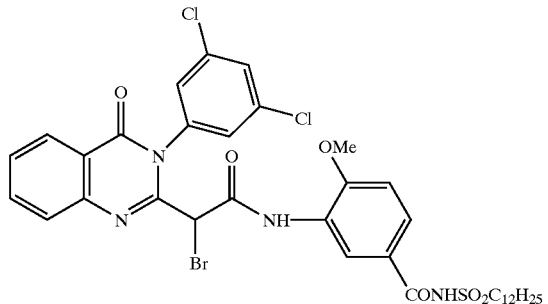
(13)
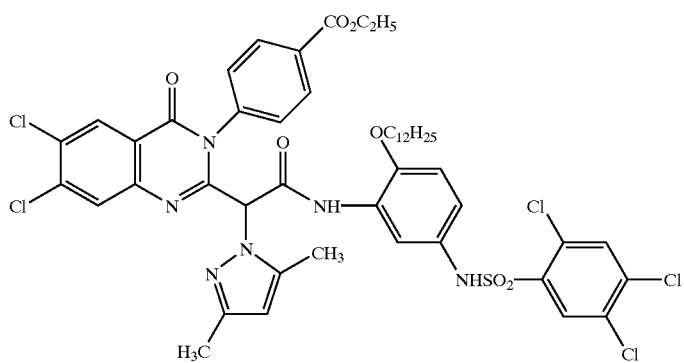

(14)
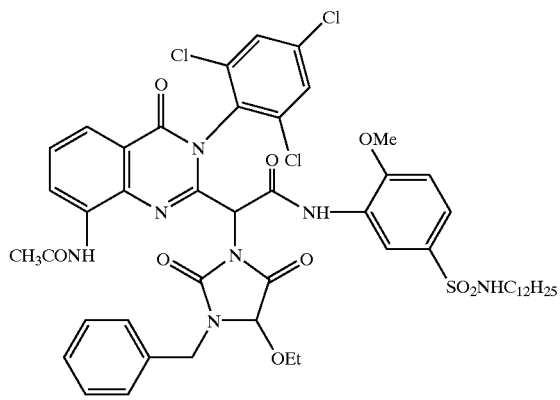
(15)
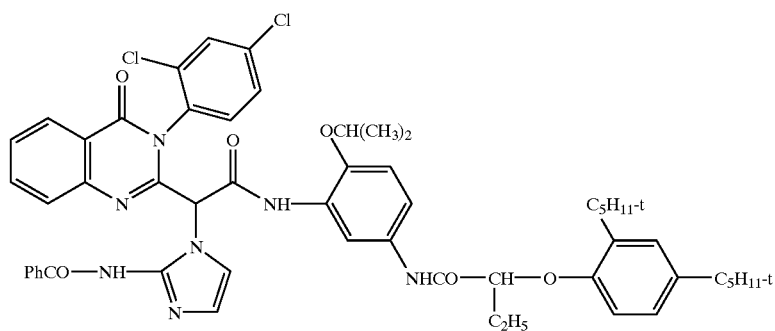
(16)
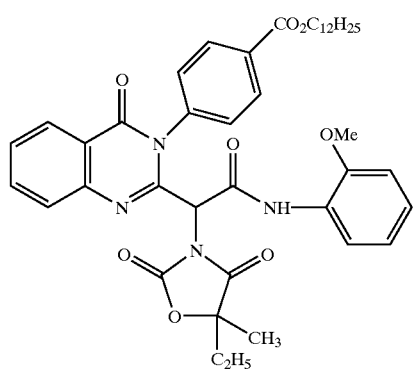
(17)
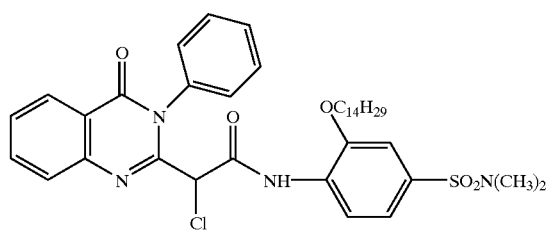

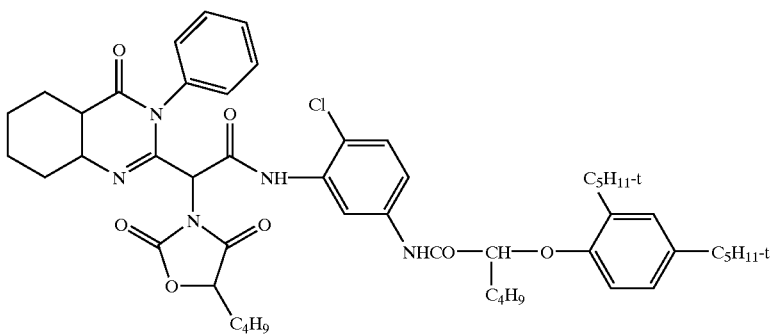
(18)
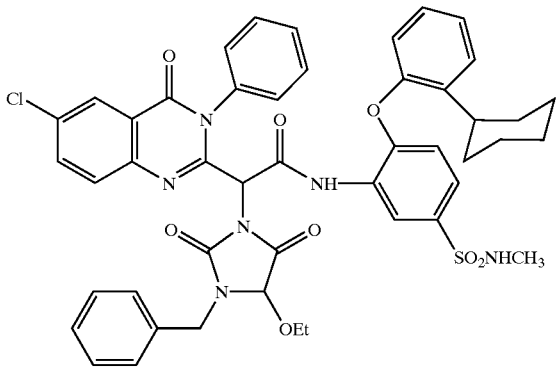
(19)
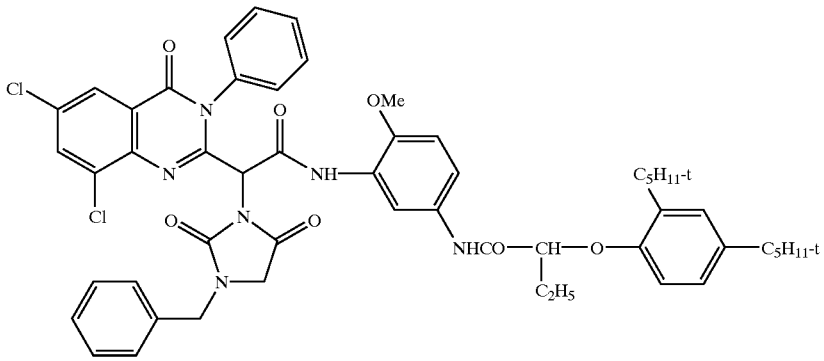
(20)
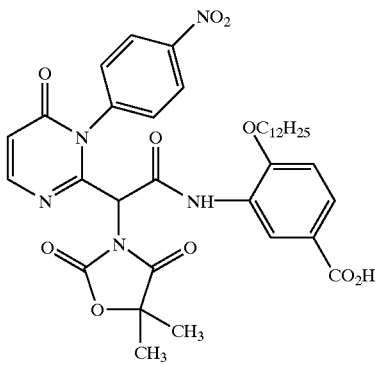
(21)

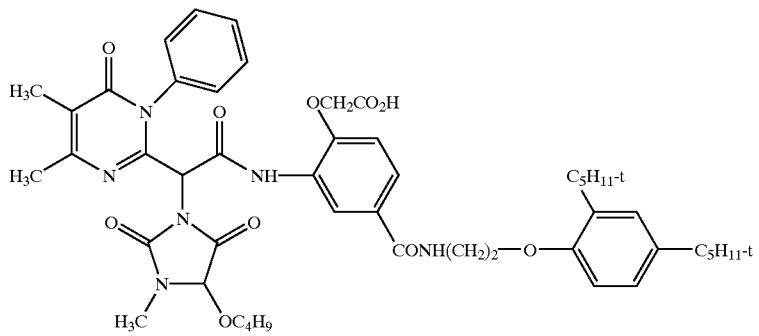
(22)
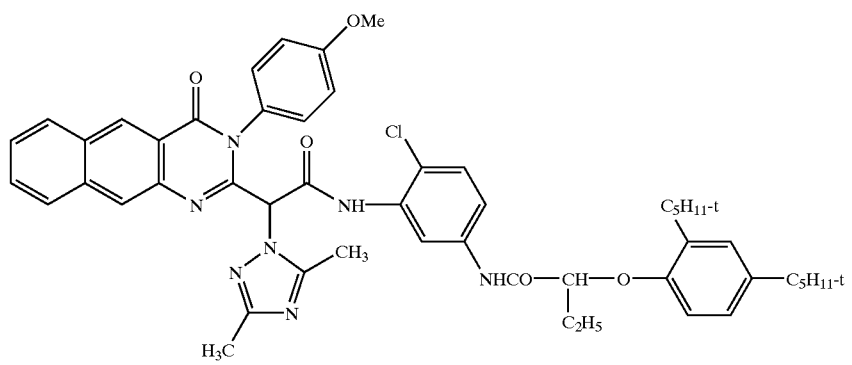
(23)
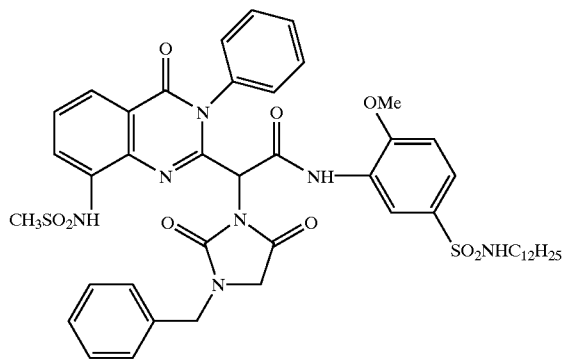
(24)
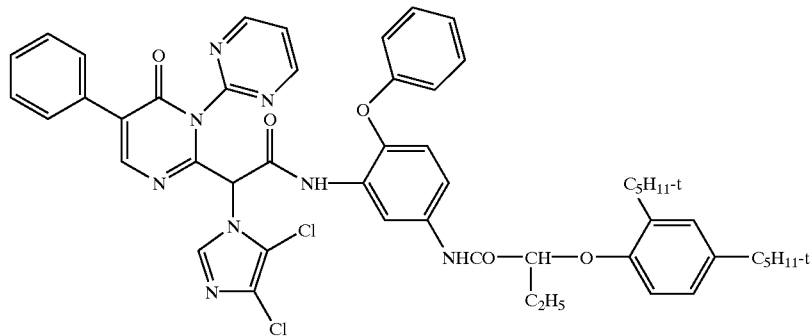
(25)

-continued
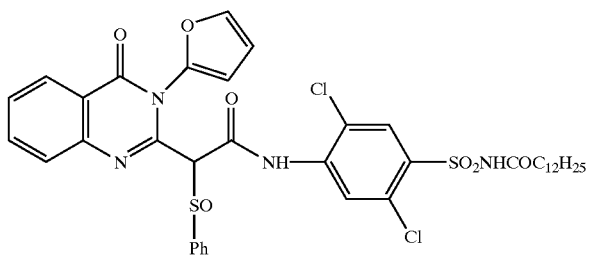
(26)
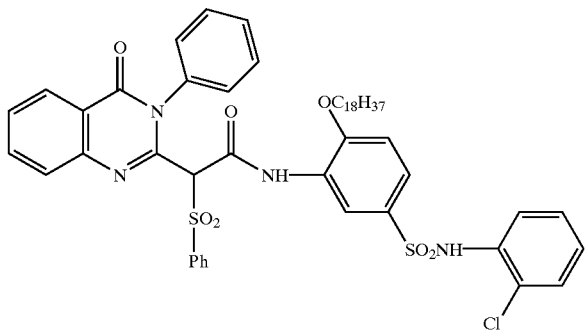
(27)
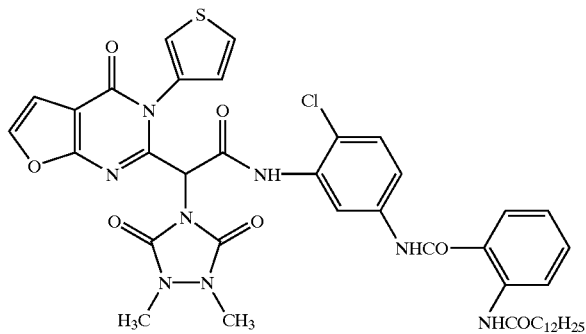
(28)
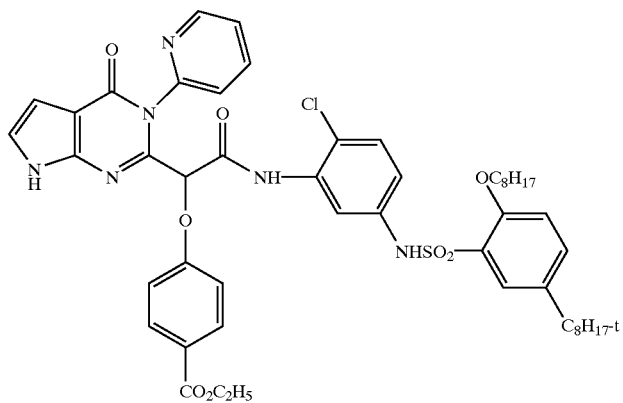
(29)

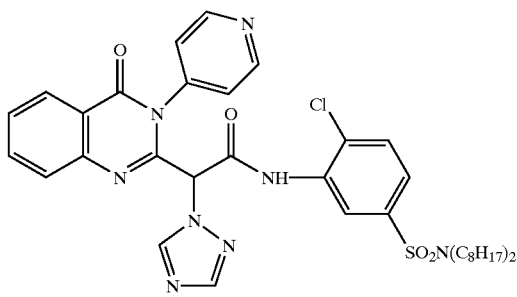
(30)
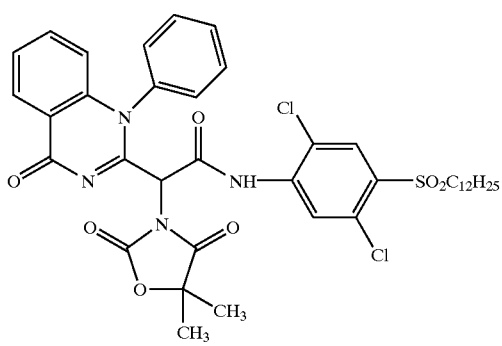
(31)
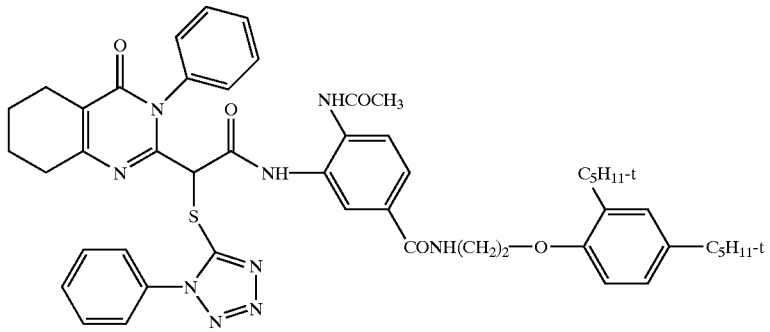
(32)
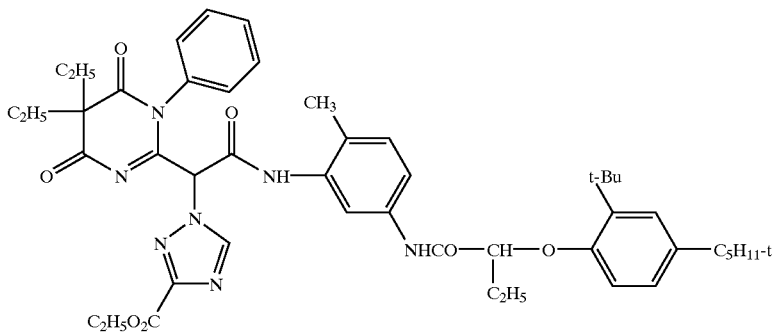
(33)

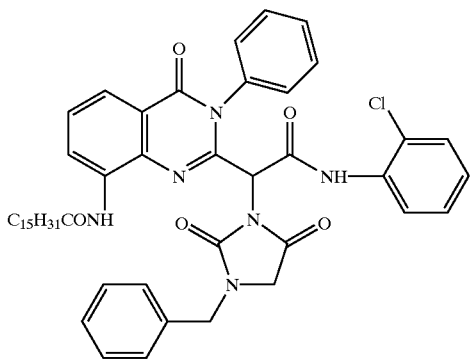
(34)
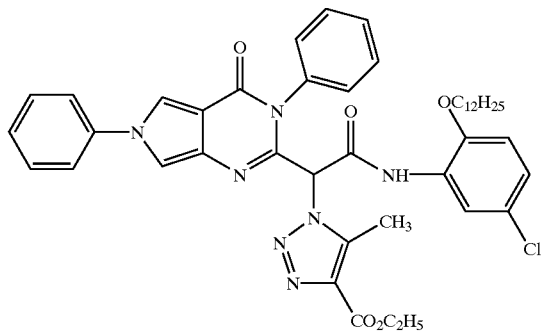
(35)
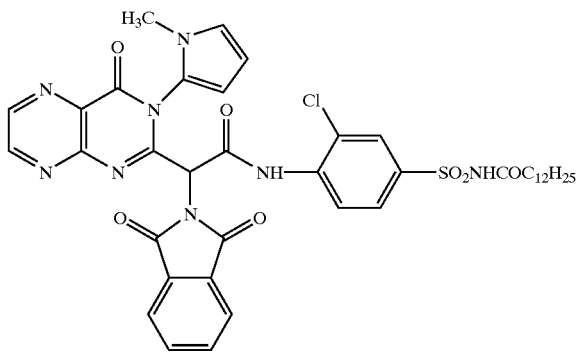
(36)
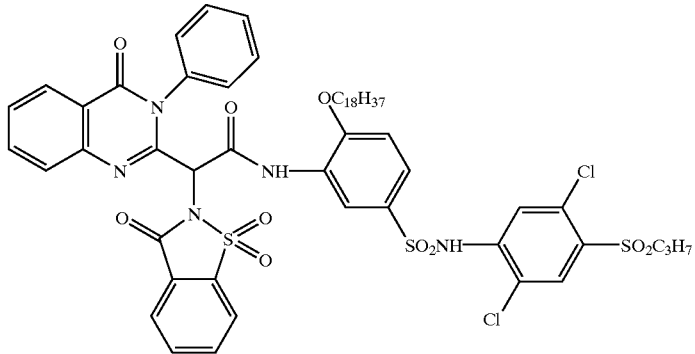
(37)

(38)

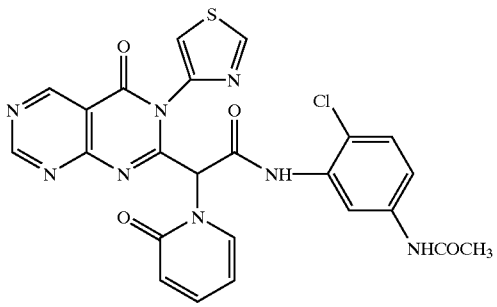

(39)

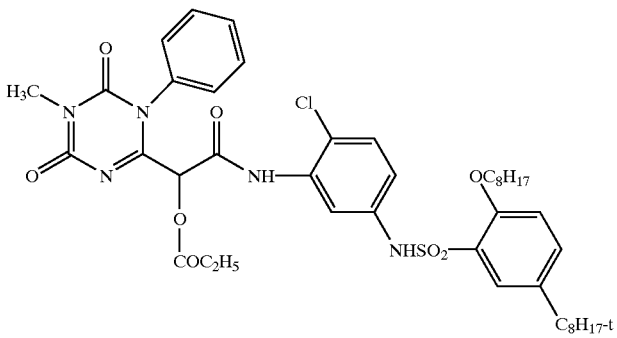

(40)

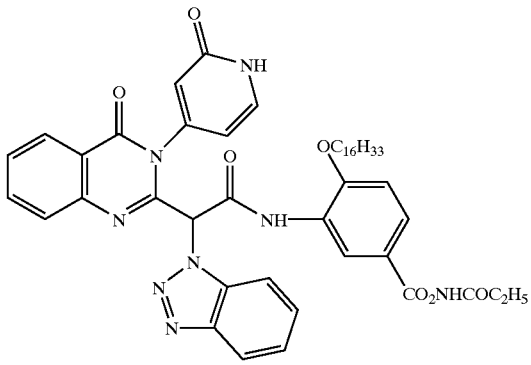

When any one of the exemplified compounds (which may also be referred to as dye-forming couplers) shown above is referred to in the following description, a number X put in parentheses, that is, (X) attached to the exemplified compound is used to express the compound as "the coupler (X)".

The following will describe specific synthetic examples of the compounds represented by formula (IA).

Synthetic Example 1

Synthesis of the Coupler (10)

The coupler (10) was synthesized according to the following route:

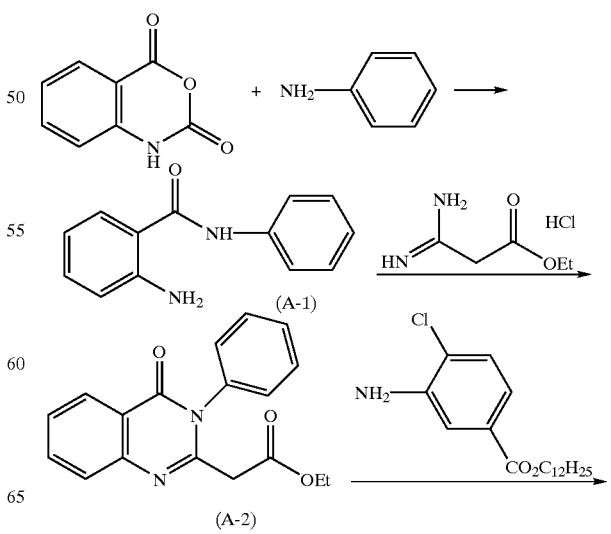

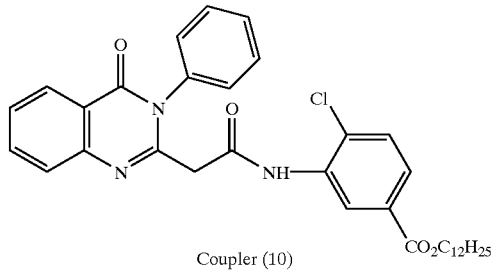

Coupler (10)

27.9 g of isatoic acid anhydride was added to a mixed solution of 200 ml of an acetonitrile containing 53.8 g of aniline and 200 ml of dimethylformamide, and the mixture was stirred at room temperature for 1 hour. The resulting mixture was heated up to 80° C. and further stirred for 1 hour. Thereafter, ethyl acetate and water were added to separate an organic layer from an aqueous layer. The organic layer was washed with 1-normal aqueous solution of hydrochloric acid, 1-normal aqueous solution of potassium carbonate and saturated brine, and then dried with magnesium sulfate anhydride. Thereafter the solvent was removed by vacuum distillation. Crystallization from a mixed solvent of ethyl acetate and hexane gave 20.1 g of Compound (A-1).

100 ml of an isopropyl alcohol solution containing 10.6 g of Compound (A-1) and 11.7 g of hydrochloride of iminoether was stirred for 3.5 hours with heating under reflux. 11.7 g of hydrochloride of iminoether was added and further stirred with heating under reflux for 3.5 hours. Crystals precipitated by cooling with ice. Suction filtration gave 11.2 g of Compound (A-2).

10 ml of a xylene solution containing 6.2 g of Compound (A-2) and 6.8 g of 2-chloro-5-dodecyloxycarbonylaniline was stirred for 4 hours with heating under reflux. Further, 1.2 g of Compound (A-2) was added and stirred for 5 hours with heating under reflux. Ethyl acetate and water were added to separate an organic layer from an aqueous layer. The organic layer was washed with 1-normal aqueous solution of hydrochloric acid and saturated brine, and then dried with magnesium sulfate anhydride. The solvent was removed by vacuum distillation. Crystallization from a mixed solvent of ethyl acetate and hexane gave 6.0 g of Coupler (10).

Synthetic Example 2

Synthesis of the Coupler (1)

The coupler (1) was synthesized according to the following route:

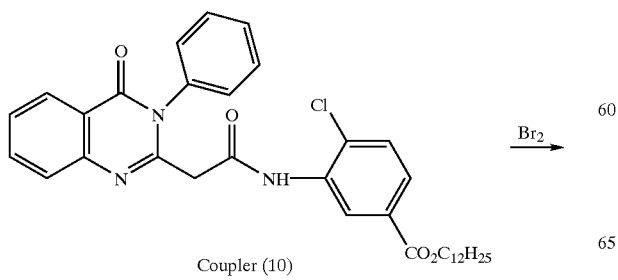

Coupler (10)

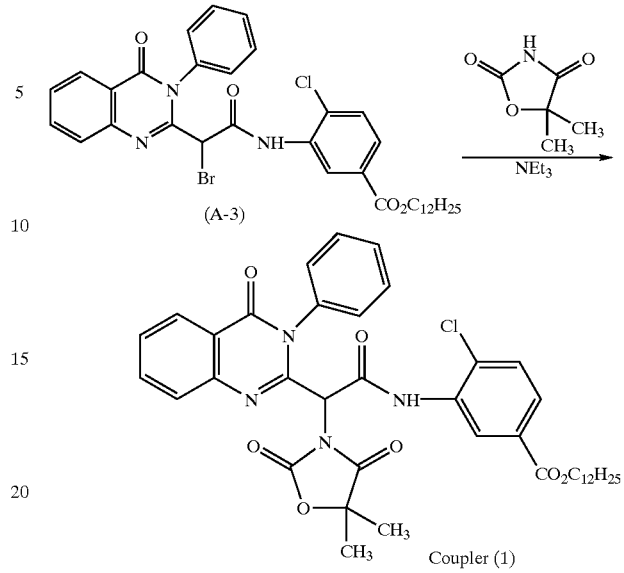

(A-3)

Coupler (1)

To 70 ml of a methylenechloride solution containing 5.4 g of Coupler (10), 15 ml of a methylenechloride solution containing 0.48 ml of bromine was added drop-wise under cooling with ice. After the mixture was stirred at room temperature for 30 minutes, methylene chloride and water were added to separate an organic layer from an aqueous layer. The organic layer was washed with saturated brine, and then dried with magnesium sulfate anhydride. The solvent was removed by vacuum distillation, to obtain a crude product of Compound (A-3).

To a solution which was prepared by dissolving 3.5 g of 5,5-dimethyloxazolidine-2,4-dione and 3.8 ml of triethylamine in 50 ml of N,N-dimethyl acetoamide, a solution containing all the previously synthesized crude product of Compound (A-3) dissolved in 50 ml of N,N-dimethylacetoamide was added drop-wise over 10 minutes at room temperature, and then stirred for 1 hour at room temperature. Ethyl acetate and water were added to separate an organic layer from an aqueous layer. The organic layer was washed with 1-normal aqueous solution of potassium carbonate, 1-normal aqueous solution of hydrochloric acid and saturated brine, and then dried with magnesium sulfate anhydride. The solvent was removed by vacuum distillation. Purification of the residue by silica gel column chromatography using a mixed solvent of ethyl acetate and hexane as the eluate gave 3.7 g of Coupler (1) as an amorphous product.

Synthetic Example 3

Synthesis of the Coupler (11)

The coupler (11) was synthesized according to the following route:

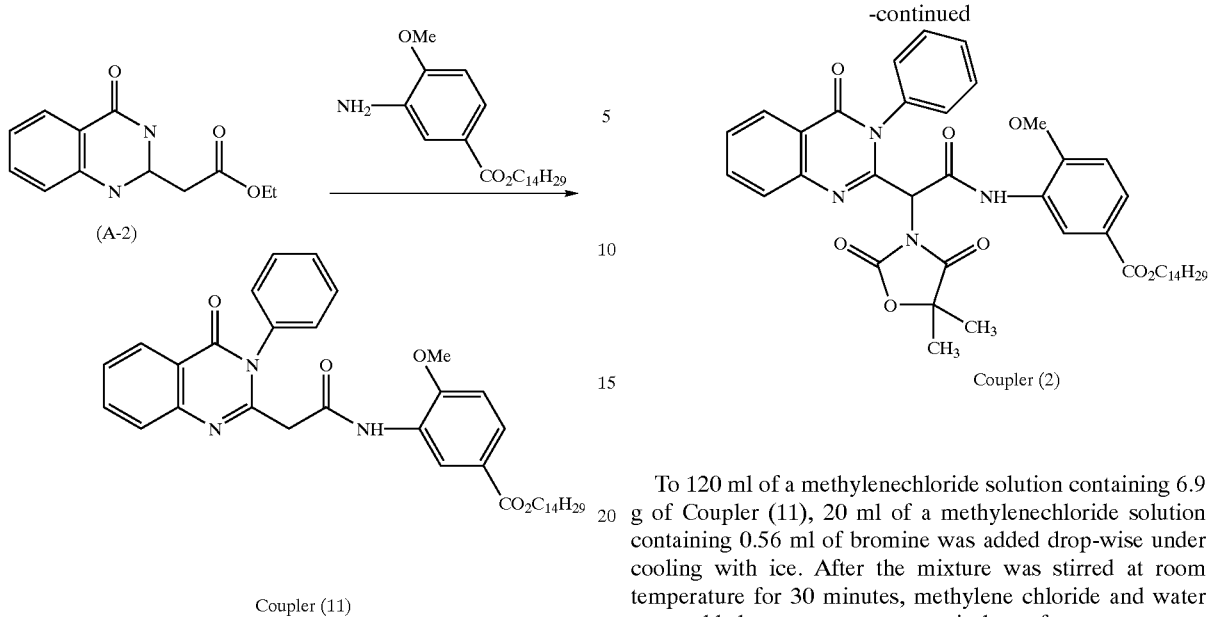

Coupler (11)

100 ml of a xylene solution containing 6.2 g of Compound (A-2) and 6.5 g of 2-methoxy-5-tetradecyloxycarbonylaniline was stirred with heating in reflux for 2 hours. Further, 0.5 g of p-toluenesulfonic acid monohydrate was added to the mixture, and the mixture was stirred with heating under reflux for 4 hours. Ethyl acetate and water were added to separate an organic layer from an aqueous layer. The organic layer was washed with 1-normal aqueous solution of hydrochloric acid and saturated brine, and then dried with magnesium sulfate anhydride. The solvent was removed by vacuum distillation. Crystallization from a mixed solvent of ethyl acetate and hexane gave 7.7 g of Coupler (11).

Synthetic Example 4

Synthesis of the Coupler (2)

The coupler (2) was synthesized according to the following route:

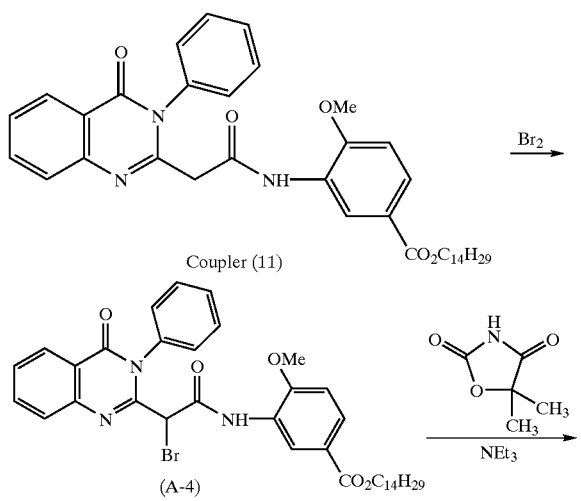

Coupler (2)

To 120 ml of a methylenechloride solution containing 6.9 g of Coupler (11), 20 ml of a methylenechloride solution containing 0.56 ml of bromine was added drop-wise under cooling with ice. After the mixture was stirred at room temperature for 30 minutes, methylene chloride and water were added to separate an organic layer from an aqueous layer. The organic layer was washed with saturated brine, and then dried with magnesium sulfate anhydride. The solvent was removed by vacuum distillation, to obtain a crude product of Compound (A-4).

To a solution which was prepared by dissolving 4.3 g of 5,5-dimethyloxazolidine-2,4-dione and 4.6 ml of triethylamine in 50 ml of N,N-dimethylacetoamide, a solution containing all the previously synthesized crude product of Compound (A-4) dissolved in 50 ml of N,N-dimethylacetoamide was added drop-wise over 10 minutes at room temperature, and then stirred for 1 hour at room temperature. Ethyl acetate and water were added to separate an organic layer from an aqueous layer. The organic layer was washed with 1-normal aqueous solution of potassium carbonate, 1-normal aqueous solution of hydrochloric acid and saturated brine, and then dried with magnesium sulfate anhydride. The solvent was removed by vacuum distillation. The residue was purified by silica gel column chromatography using a mixed solvent of ethyl acetate and hexane as the eluate. Crystallization from methanol gave 4.4 g of Coupler (2).

Next, the compounds represented by formula (IB) among the compounds represented by the aforementioned formula (I) of the present invention are explained in detail.

The compound represented by formula (IB) of the present invention is characterized in the nitrogen-containing heterocyclic ring of a nitrogen-containing heterocyclic acetoanilide compound. The above described problems in the conventional technique have been solved, by introducing a bulky substituent onto a nitrogen ring that constitutes the above-said heterocyclic ring. It is assumed that the introduction of the bulky-group has an influence on a dye structure control. If the degree of bulkiness of the group is too large, satisfactory photographic properties tends to become difficult to obtain, whereas if the degree is too small, it is difficult to solve the above-described problems in the conventional technique.

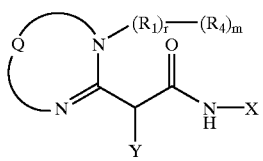

formula (IB)

In formula (IB), $R_1$ represents a methylene group (—$CH_2$—), a methine group (—CH(—)—), or a carbon atom (—C(—)(—)—).

r represents an integer of 1 to 30. $R_1$s may be the same or different independently, when r is 2 or more. r preferably represents an integer of 1 to 10, more preferably 1 to 7, furthermore preferably 1 to 6, and most preferably 1 to 3.

$R_4$ represents a substituent excepting a hydrogen atom. Examples of the substituent include halogen atoms, alkyl (including cycloalkyl and bicycloalkyl), alkenyl (including cycloalkenyl and bicycloalkenyl), alkynyl, aryl, heterocyclic, cyano, hydroxyl, nitro, carboxyl, alkoxy, aryloxy, silyloxy, heterocyclic oxy, acyloxy, carbamoyloxy, alkoxycarbonyloxy, aryloxycarbonyloxy, amino (including alkylamino and anilino), acylamino, aminocarbonylamino, alkoxycarbonylamino, aryloxycarbonylamino, sulfamoylamino, alkyl- or aryl-sulfonylamino, mercapto, alkylthio, arylthio, heterocyclic thio, sulfamoyl, sulfo, alkyl- or aryl-sulfinyl, alkyl- or aryl-sulfonyl, acyl, aryloxycarbonyl, alkoxycarbonyl, carbamoyl, aryl- or heterocyclic-azo, imido, phosphio, phosphinyl, phosphinyloxy, phosphinylamino, and silyl groups. m represents an integer of 1 to 30. m preferably represents an integer of 1 to 6, more preferably 1 or more and 3 or less, and furthermore preferably 1.

The above-mentioned substituents may be further substituted with a substituent such as those described above.

Examples of the group of $R_4$ are further explained below.

Examples of these substituents include a halogen atom (e.g., chlorine, bromine, iodine); an alkyl group (preferably a straight-chain or branched-chain, substituted or unsubstituted alkyl group, more preferably the alkyl group having 1 to 30 carbon atoms, e.g., methyl, ethyl, n-propyl, isopropyl, t-butyl, n-octyl, eicosyl, 2-chloroethyl, 2-cyanoethyl, 2-ethylhexyl); a cycloalkyl group (preferably a substituted or unsubstituted monocyclic cycloalkyl group having 3 to 30 carbon atoms, e.g., cyclohexyl, cyclopentyl, and 4-n-dodecylcyclohexyl, and a polycycloalkyl group including groups composed of a polycyclic structure such as a bicycloalkyl group (preferably a substituted or unsubstituted bicycloalkyl group having 5 to 30 carbon atoms, e.g., bicyclo[1,2,2]heptane-2-yl and bicyclo[2,2,2]octane-3-yl) or a tricycloalkyl group; more preferably a monocycloalkyl group or a bicycloalkyl group and particularly preferably a monocyclic cycloalkyl group); an alkenyl group (preferably a straight-chain or branched-chain, and substituted or unsubstituted alkenyl group, more preferably the alkenyl group having 2 to 30 carbon atoms, e.g., vinyl, allyl, prenyl, geranyl, oleyl); a cycloalkenyl group (preferably a substituted or unsubstituted cycloalkenyl group having 3 to 30 carbon atoms, e.g., 2-cyclopentene-1-yl, and 2-cyclohexene-1-yl; and a polycycloalkenyl group such as a bicycloalkenyl group (preferably a substituted or unsubstituted bicycloalkenyl group having 5 to 30 carbon atoms, e.g., bicyclo[2,2,1]hepto-2-ene-1-yl or bicyclo[2,2,2]octo-2-ene-4-yl), or a tricycloalkenyl group, with a monocyclic cycloalkenyl group being particularly preferred); an alkynyl group (preferably a substituted or unsubstituted alkynyl group having 2 to 30 carbon atoms, e.g., ethynyl, propargyl, trimethylsilylethynyl); an aryl group (preferably a substituted or unsubstituted aryl group having 6 to 30 carbon atoms, e.g., phenyl, p-tolyl, naphthyl, m-chlorophenyl, o-hexadecanoylaminophenyl); a heterocyclic group (preferably 5- to 7-membered substituted or unsubstituted, saturated or unsaturated, aromatic or non-aromatic, and monocyclic or condensed heterocyclic group, more preferably a heterocyclic group having ring-constituting atoms selected from carbon, nitrogen and sulfur atoms, the heterocyclic group containing at least one hetero atom selected from the group consisting of nitrogen, oxygen and sulfur atoms; furthermore preferably a 5- to 6-membered aromatic heterocyclic group having 3 to 30 carbon atoms, e.g., 2-furyl, 2-thienyl, 2-pyridyl, 4-pyridyl, 2-pyrimidinyl, 2-benzothiazolyl); a cyano group; a hydroxyl group; a nitro group; a carboxyl group; an alkoxy group (preferably a substituted or unsubstituted alkoxyl group having 1 to 30 carbon atoms, e.g., methoxy, ethoxy, isopropoxy, t-butoxy, n-octyloxy, 2-methoxyethoxy); an aryloxy group (preferably a substituted or unsubstituted aryloxy group having 6 to 30 carbon atoms, e.g., phenoxy, 2-methylphenoxy, 2,4-di-t-amylphenoxy, 4-t-buthylphenoxy, 3-nitrophenoxy, 2-tetradecanoylaminophenoxy); a silyloxy group (preferably a silyloxy group having 3 to 20 carbon atoms, e.g., trimethylsilyloxy, t-butyldimethylsilyloxy); a herocyclic oxy group (preferably a substituted or unsubstituted heterocyclic oxy group having 2 to 30 carbon atoms, more preferably those having the heterocyclic moiety as described to explain the above-mentioned heterocyclic group, e.g., 1-phenyltetrazole-5-oxy, 2-tetrahydropyranyloxy); an acyloxy group (preferably formyloxy, a substituted or unsubstituted alkylcarbonyloxy group having 2 to 30 carbon atoms or a substituted or unsubstituted arylcarbonyloxy group having 6 to 30 carbon atoms, e.g., formyloxy, acetyloxy, pivaloyloxy, stealoyloxy, benzoyloxy, p-methoxyphenylcarbonyloxy); a carbamoyloxy group (preferably a substituted or unsubstituted carbamoyloxy group having 1 to 30 carbon atoms, e.g., N,N-dimethylcarbamoyloxy, N,N-diethylcarbamoyloxy, morpholinocarbonyloxy, N,N-di-n-octylaminocarbonyloxy, N-n-octylcarbamoyloxy); an alkoxycarbonyloxy group (preferably a substituted or unsubstituted alkoxycarbonyloxy group having 2 to 30 carbon atoms, e.g., methoxycarbonyloxy, ethoxycarbonyloxy, t-butoxy carbonyloxy, n-octylcarbonyloxy); an aryloxycarbonyloxy group (preferably a substituted or unsubstituted aryloxycarbonyloxy group having 7 to 30 carbon atoms, e.g., phenoxycarbonyloxy, p-methoxyphenoxycarbonyloxy, p-n-hexadecyloxyphenoxycarbonyloxy); an amino group (preferably an unsubstituted amino group, a substituted or unsubstituted alkylamino group having 1 to 30 carbon atoms, a substituted or unsubstituted arylamino group having 6 to 30 carbon atoms and a heterocyclic amino group having 0 (zero) to 30 carbon atoms e.g., amino, methylamino, dimethylamino, anilino, N-methylanilino, diphenylamino, N-1,3,5-triazine-2-il amino); an acylamino group (preferably a formylamino group, a substituted or unsubstituted alkylcarbonylamino group having 1 to 30 carbon atoms, and a substituted or unsubstituted arylcarbonylamino group having 6 to 30 carbon atoms, e.g., formylamino, acetylamino, pivaloylamino, lauroylamino, benzoylamino and 3,4,5-tri-n-octyloxyphenylcarbonylamino); an aminocarbonylamino group (preferably a substituted or unsubstituted aminocarbonylamino group having 1 to 30 carbon atoms, e.g., carbamoylamino, N,N-dimethylaminocarbonylamino, N,N-diethylaminocarbonylamino, morpholinocarbonylamino); an alkoxycarbonylamino group (preferably a substituted or unsubstituted alkoxycarbonylamino group having 2 to 30 carbon atoms, e.g., methoxycarbonylamino, ethoxycarbonylamino, t-butoxycarbonylamino, n-octadecyloxycarbonylamino, N-methyl-methoxycarbonylamino); an aryloxycarbonylamino group (preferably a substituted or unsubstituted aryloxycarbonylamino group having 7 to 30 carbon atoms, e.g., phenoxycarbonylamino, p-chlorophenoxycarbonylamino, m-n-octyloxyphenoxycarbonyl amino); a sulfamoyl amino group (preferably a substituted or unsubstituted sulfamoylamino group having 0 (zero) to 30 carbon atoms, e.g., sulfamoylamino, N,N-dimethylaminosulfonylamino, N-n-octyl aminosulfonylamino); an alkyl- or aryl-sulfonylamino group (preferably a substituted or unsubstituted alkyl sulfonylamino group having 1 to 30 carbon atoms and a substituted or unsubstituted arylsulfonylamino group having 6 to 30 carbon atoms, e.g., methylsulfonylamino, butylsulfonylamino, phenylsulfonylamino, 2,3,5-trichlorophenylsulfonylamino, p-methylphenylsulfonylamino); a mercapto group; an alkylthio group (preferably a substituted or unsubstituted alkylthio group having 1 to 30 carbon atoms, e.g., methylthio, ethylthio, n-hexadecylthio); an arylthio group (preferably a substituted or unsubstituted arylthio group having 6 to 30 carbon atoms, e.g., phenylthio, p-chlorophenylthio, m-methoxyphenylthio); a heterocyclic thio group (preferably a substituted or unsubstituted heterocyclic thio group having 2 to 30 carbon atoms in which the heterocyclic moiety is preferably the same as that of the above-described heterocyclic group, e.g., 2-benzothiazolylthio, 1-phenyltetrazol-5-ylthio); a sulfamoyl group (preferably a substituted or unsubstituted sulfamoyl group having 0 (zero) to 30 carbon atoms, e.g., N-ethylsulfamoyl, N-(3-dodecyloxypropyl)sulfamoyl, N,N-dimethyl sulfamoyl, N-acetylsulfamoyl, N-benzoylsulfamoyl, N-(N'-phenylcarbamoyl) sulfamoyl); a sulfo group; an alkyl- or aryl-sulfinyl group (preferably a substituted or unsubstituted alkylsulfinyl group having 1 to 30 carbon atoms or a substituted or unsubstituted arylsulfinyl group having 6 to 30 carbon atoms, e.g., methylsulfinyl, ethylsulfinyl, phenylsulfinyl, p-methylphenylsulfinyl); an alkyl- or aryl-sulfonyl group (preferably a substituted or unsubstituted alkylsulfonyl group having 1 to 30 carbon atoms and a substituted or unsubstituted arylsulfonyl group having 6 to 30 carbon atoms, e.g., methylsulfonyl, ethylsulfonyl, phenylsulfonyl, p-methylphenylsulfonyl); an acyl group (preferably a formyl group, a substituted or unsubstituted alkylcarbonyl group having 2 to 30 carbon atoms and a substituted or unsubstituted arylcarbonyl group having 7 to 30 carbon atoms, e.g., acetyl, pivaloyl, 2-chloroacetyl, stearoyl, benzoyl, p-n-octyloxyphenylcarbonyl); an aryloxycarbonyl group (preferably a substituted or unsubstituted aryloxycarbonyl group having 7 to 30 carbon atoms, e.g., phenoxycarbonyl, o-chlorophenoxycarbonyl, m-nitrophenoxycarbonyl, p-t-butylphenoxycarbonyl); an alkoxycarbonyl group (preferably a substituted or unsubstituted alkoxycarbonyl group having 2 to 30 carbon atoms, e.g., methoxycarbonyl, ethoxycarbonyl, t-butoxycarbonyl, n-octadecyloxycarbonyl); a carbamoyl group (preferably a substituted or unsubstituted carbamoyl group having 1 to 30 carbon atoms, e.g., carbamoyl, N-methylcarbamoyl, N,N-dimethylcarbamoyl, N,N-di-n-octylcarbamoyl, N-(methylsulfonyl)carbamoyl); an aryl- or heterocyclic-azo group (preferably a substituted or unsubstituted aryl azo group having 6 to 30 carbon atoms, and a substituted or unsubstituted heterocyclic azo group having 3 to 30 carbon atoms in which the heterocyclic moiety is preferably the same as that of the above-described heterocyclic group, e.g., phenylazo, p-chlorophenylazo, 5-ethylthio-1,3,4-thiadiazole-2-yl azo); an imido group (preferably a substituted or unsubstituted imido group having 2 to 30 carbon atoms, e.g., N-succinimido, N-phthalimido); a phosphino group (preferably a substituted or unsubstituted phosphino group having 2 to 30 carbon atoms, e.g., dimethylphosphino, diphenylphosphino, methylphenoxyphosphino); a phosphinyl group (preferably a substituted or unsubstituted phosphinyl group having 2 to 30 carbon atoms, e.g., phosphinyl, dioctyloxyphosphinyl, diethoxyphosphinyl); a phosphinyloxy group (preferably a substituted or unsubstituted phosphinyloxy group having 2 to 30 carbon atoms, e.g., diphenoxyphosphinyloxy, dioctyloxyphosphinyloxy); a phosphinylamino group (preferably a substituted or unsubstituted phosphinylamino group having 2 to 30 carbon atoms, e.g., dimethoxyphosphinylamino, dimethylaminophosphinylamino); and a silyl group (preferably a substituted or unsubstituted silyl group having 3 to 30 carbon atoms, e.g., trimethylsilyl, t-butyldimethylsilyl, phenyldimethylsilyl).

Among the group represented by $R_4$, a hydrogen atom(s) in the substituents may be replaced with the above-described group. Examples of these group $R_4$s include an alkylcarbonylaminosulfonyl group, an arylcarbonylaminosulfonyl group, an alkylsulfonylaminocarbonyl group, and an arylsulfonyl aminocarbonyl group. As the specific examples, a methylsulfonyl aminocarbonyl, a p-methylphenylsulfonylaminocarbonyl, an acetylaminosulfonyl, a benzoylaminosulfonyl, a dodecylcarbonylaminosulfonyl, a p-chlorophenylcarbonylaminosulfonyl, a dodecanesulfonylaminocarbonyl, a p-toluene sulfonylaminocarbonyl, or a p-dodecyloxybenzenesulfonylaminocarbonyl group are enumerated.

The groups represented by $R_4$ may be the same or different independently, or the group represented by $R_4$ may bond with each other to form a ring, preferably a 5- to 7-membered saturated or unsaturated ring, when m is 2 or more. The ring may be an alicyclic ring, an aromatic ring, or a heterocyclic ring. Examples of these rings include a benzene, a furan, a thiophene, a cyclopentene or a cyclohexane ring.

The rings that are formed by bonding of these substituents with each other, may have a substituent such as those enumerated as the group represented by the above-mentioned $R_4$.

Further, $R_4$s may combine with each other to form a multiple bond. Specifically, the —$(R_1)_r$—$(R_4)_m$ group may be an alkenyl group or an alkynyl group. However, the —$(R_1)_r$—$(R_4)_m$ group does not represent a straight-chain alkyl group.

At least one $R_4$, preferably all the $R_4$s, preferably bonds with a carbon atom(s) at the α-, β-, γ- and/or δ-position(s) in the $(R_1)_r$. Herein, the position of a carbon atom in $(R_1)_r$ that directly bonds with the nitrogen atom on the heterocyclic ring composed of Q and the —N—C=N— moiety, is referred to as "α-position". Likewise, the position of a carbon atom adjacent to the α-position carbon atom is referred to as "β-position", the further adjacent position thereto as "γ-position", and the still further adjacent position thereto as "δ-position", in turn. Further, more preferably, in case where $R_4$ exclusively consists of alkyl groups, at least one of the alkyl groups preferably bonds with a carbon atom at the α-position or β-position. Besides, more preferably in case where at least one of $R_4$s is an aryl group, at least one of the aryl group(s) preferably bonds with a carbon atom at the α-position or β-position. On the other hand, in case where $R_4$ is a substituent which neither contains an aryl group nor exclusively consists of alkyl groups, the $R_4$ more preferably bonds with a carbon atom at the β-position, γ-position or δ-position (further preferably β- or γ-position).

In case where r is in the range of 8 to 30, bond of the substituents of $R_4$ is not limited to the particular position, but the above-described positions are preferable. On the other hand, a preferable range of r is the same as mentioned above.

The total carbon atoms of the substituents of $R_4$ is preferably 2 to 50, more preferably 7 to 45, further preferably 10 to 40, and most preferably 15 to 40.

Preferred of these substituents of $R_4$ are an alkyl group, an alkenyl group, an aryl group, a heterocyclic group, a halogen atom, an amino group, a hydroxyl group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, a cyano group, an alkoxy group and an aryloxy group.

More preferred of these substituents of $R_4$ are an alkyl group, an aryl group, a heterocyclic group, a halogen atom, an amino group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, a cyano group, an alkoxy group and an aryloxy group. An aryl group, an alkoxy group and an aryloxy group are furthermore preferred.

Concentrating on the —$(R_1)_r$—$(R_4)_m$ group of the dye-forming coupler represented by formula (IB) according to the present invention, the above-mentioned preferable group of $R_4$ can be grouped into the followings:

Group 1

In case where the —$(R_1)_r$—$(R_4)_m$ group is an unsubstituted branched alkyl group:

The total carbon atoms of the $(R_1)_r$ and $(R_4)_m$ is preferably 8 or more, more preferably 8 to 40, and further preferably 10 to 30. $R_4$ preferably bonds with $(R_1)_r$ at the α-position or β-position.

When $R_4$ bonds with $(R_1)_r$ at the α-position, the bulkiness at the neighborhood of the resultant dye increases, even though the total carbon atoms of the above-mentioned group is 7 or less. Consequently, such embodiment is also preferable in the second place to the above.

Group 2

In case where at least one of $R_4$ is an alkoxy group or an aryloxy group:

The total carbon atoms of the alkoxy group or the aryloxy group is preferably 8 or more, more preferably 8 to 40, and further preferably 10 to 30. The alkoxy group or the aryloxy group preferably bonds with $(R_1)_r$ at the β-position, γ-position or δ-position (more preferably β- or γ-position).

Group 3

In case where at least one of $R_4$ is an aryl group, a heterocyclic group, a halogen atom, an amino group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, or a cyano group:

When the at least one group $R_4$ is the aryl group, the aryl group preferably bonds with $(R_1)_r$ at the α-position or β-position, particularly preferably α-position. On the other hand, when $R_4$ does not contain an aryl group, at least one $R_4$ of a heterocyclic group, a halogen atom, an amino group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, and a cyano group preferably bonds with $(R)_r$ at the β-position or γ-position.

Among these groups, it is more preferable that at least one of $R_4$ is an aryl group. The $(R_4)_m$ in which $R_4$ is an aryl group and m is 1, is furthermore preferred. The —$(R_1)_r$—$(R_4)_m$ group as a whole including —$(R_1)_r$ is most preferably a benzyl group.

In formula (IB), Q represents a residue that forms, together with the —N—C=N— moiety, a nitrogen-containing 6-membered heterocyclic ring. The nitrogen-containing heterocyclic ring is a substituted or unsubstituted heterocyclic ring, more preferably a heterocyclic ring composed of a carbon atom and a nitrogen atom, as ring-forming atoms, and having 2 to 4 nitrogen atoms; furthermore preferably a nitrogen-containing 6-membered heterocyclic ring having 2 to 30 carbon atoms and 2 nitrogen atoms. Examples of the nitrogen-containing 6-membered ring that is formed by Q together with the —N—C=N— moiety, include 4-pyrimidone, 1,3-diazine-4,6-dione, 1,3,5-triazine-2-one and 1,2,4-triazine-5-one. The nitrogen-containing 6-membered ring that is formed by Q together with the —N—C=N— moiety, may have a substituent. Examples of the substituent are the same as those of $R_4$ mentioned above.

Further, the substituents adjacent to each other may combine together to form a ring, preferably a 5- to 7-membered saturated or unsaturated ring, and the ring may be alicyclic, aromatic or heterocyclic ring. As the examples of the ring, benzene, furan, thiophene, cyclopentane, and cyclohexane rings are enumerated.

Each of the above-mentioned substituents and the rings that are formed by combination of some of these substituents with each other, also may have a substituent. Examples of the substituent are the same as those of $R_4$ mentioned above.

The total carbon atoms of the above-mentioned substituent is preferably 2 to 50, more preferably 8 to 45, furthermore preferably 15 to 40.

Preferred of these substituents are an alkyl group, an alkenyl group, an aryl group, a heterocyclic group, a halogen atom, an alkoxy group, an aryloxy group, an alkylthio group, an arylthio group, a cyano group, an acylamino group, an alkyl- or aryl-sulfonylamino group, an alkoxycarboxyl group, a carbamoyl group, a sulfamoyl group, an alkylamino group and an arylamino group.

Q is preferably a residue that forms, together with the —N—C=N— moiety, a 4-pyrimidone ring. More preferably Q is represented by —C(—$R_2$)=C(—$R_3$)—CO—. $R_2$ and $R_3$, when combined with each other, form, together with the —C=C— moiety, a 5- to 7-membered ring, or $R_2$ and $R_3$ each independently represent a hydrogen atom or a substituent. The ring that is formed by combination of $R_2$ and $R_3$ together with the —C=C— moiety, is preferably a 5- to 7-membered alicyclic, aromatic or heterocyclic ring. As examples of the ring, benzene, pyrazole, furan, thiophene, cyclopentene and cyclohexene rings are enumerated. More preferably the ring is a 6-membered aromatic ring. A benzene ring is most preferred.

When $R_2$ and $R_3$ each represent a substituent, $R_2$ and $R_3$ may be the same or different independently. Examples of the substituent are the same as those of $R_4$ mentioned above.

In formula (IB), X represents an aryl group. The aryl group is preferably a substituted or unsubstituted aryl group having 6 to 30 carbon atoms, such as a phenyl group and a naphthyl group. X may have a substituent. Examples of the substituent are the same as those of $R_4$ mentioned above. Preferable examples of the substituent that X may have, include an alkyl group, an alkenyl group, an aryl group, a heterocyclic group, a halogen atom, an alkoxy group, an aryloxy group, an alkylthio group, an arylthio group, a cyano group, an acylamino group, an alkyl- or aryl-sulfonylamino group, an alkoxycarboxyl group, a carbamoyl group, a sulfamoyl group, an alkylamino group and an arylamino group.

Preferably the carbon atom adjacent to the position of the amido group on the aryl group, bonds with a halogen atom (e.g., fluorine, chlorine), an alkyl group (e.g., methyl), an alkoxy group (e.g., methoxy, isopropyloxy, dodecyloxy), or an aryloxy group (e.g., phenyloxy). Among these groups, a halogen atom and an alkoxy group are more preferred. An alkoxy group is furthermore preferred.

In the coupler of the present invention, X is preferably a phenyl group. Assuming that the position where the phenyl group bonds with the amido group is the 1-position, the phenyl group preferably has the above-mentioned substituent at least at the 2-position, more preferably has the substituents at the 2- and 5-positions.

In formula (IB), Y represents a hydrogen atom, or a group that is capable of being split-off upon a coupling reaction with an oxidized product of a developing agent. Examples of Y include a group that splits off with a nitrogen, oxygen, or sulfur atom (a splitting-off atom) and a halogen atom (e.g., chlorine, bromine).

Examples of the group that splits off with a nitrogen atom, include a heterocyclic group (preferably a 5- to 7-membered substituted or unsubstituted, saturated or unsaturated, aromatic (herein the term "aromatic" is used to embrace a substance that has (4n+2) cyclic conjugated electrons) or non-aromatic, monocyclic or condensed heterocyclic group, more preferably a 5- to 6-membered heterocyclic group, in which the ring-forming atom is selected from carbon, nitrogen and sulfur atoms and in addition at least one of hetero atoms selected from nitrogen, oxygen and sulfur atoms is incorporated, with specific examples of the heterocyclic ring including succinimide, maleinimide, phthalimide, diglycolimide, pyrrole, pyrazole, imidazole, 1,2,4-triazole, tetrazole, indole, benzopyrazole, benzimidazole, benzotriazole, imidazoline-2,4-dione, oxazolidine-2,4-dione, thiazolidine-2-one, benzimidazoline-2-one, benzoxazoline-2-one, benzothiazoline-2-one, 2-pyrroline-5-one, 2-imidazoline-5-one, indoline-2,3-dione, 2,6-dioxypurine parabanic acid, 1,2,4-triazolidine-3,5-dione, 2-pyridone, 4-pyridone, 2-pyrimidone, 6-pyridazone, 2-pyrazone, 2-amino-1,3,4-thiazolidine-4-one), a carbon-amido group (e.g., acetamido, trifluoroacetamido), a sulfonamido group (e.g., methanesulfonamido, benzenesulfonamido), an arylazo group (e.g., phenylazo, naphthylazo), and a carbamoylamino group (e.g., N-methyl carbamoylamino).

Preferred of the group that splits off with a nitrogen atom is a heterocyclic group, more preferably an aromatic heterocyclic group having 1, 2, or 4 ring-forming nitrogen atoms, or a heterocyclic group represented by the following formula (LB). The heterocyclic group represented by the following formula (LB) are furthermore preferred.

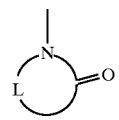

formula (LB)

In the formula (LB), L represents a residue that forms, together with —NC(=O)—, a 5- to 6-membered nitrogen-containing heterocyclic ring.

Examples of the residues are enumerated in the explanation of the above-mentioned heterocyclic group, and such residues as enumerated above are more preferred.

Particularly preferably L is a residue that forms, together with the —NC(=O)—, a 5-membered nitrogen-containing heterocyclic ring.

Examples of the group that splits off with an oxygen atom include an aryloxy group (e.g., phenoxy, 1-naphthoxy), a heterocyclic oxy group (e.g., pyridyloxy, pyrazolyloxy), an acyloxy group (e.g., acetoxy, benzoyloxy), an alkoxy group (e.g., methoxy, dodecyloxy), a carbamoyloxy group (e.g., N,N-diethylcarbamoyloxy, morpholinocarbamoyloxy), an aryloxycarbonyloxy group (e.g., phenoxycarbonyloxy), an alkoxycarbonyloxy group (e.g., methoxycarbonyloxy, ethoxycarbonyloxy), an alkylsulfonyloxy group (e.g., methanesulfonyloxy), and an arylsulfonyloxy group (e.g., benzenesulfonyloxy, toluenesulfonyloxy).

Preferred of these groups are an aryloxy group, an acyloxy group and a heterocyclic oxy group.

Examples of the group that splits off with a sulfur atom include an arylthio group (e.g., phenylthio, naphthylthio), a heterocyclic thio group (e.g., tetrazolylthio, 1,3,4-thiadiazolylthio, 1,3,4-oxazolylthio, benzimidazolylthio), an alkylthio group (e.g., methylthio, octylthio, hexadecylthio), an alkylsulfinyl group (e.g., methanesulfinyl), an arylsulfinyl group (e.g., benzenesulfinyl), an arylsulfonyl group (e.g., benzenesulfonyl), and an alkylsulfonyl group (e.g., methanesulfonyl).

Preferred of the group that splits off with a sulfur atom are an arylthio group and a heterocyclic thio group. A heterocyclic thio group is more preferred.

Y may be substituted with a substituent. Examples of the substituent include those enumerated as the substituent of $R_4$ described above.

Y is preferably the group that splits off with a nitrogen, an oxygen, or a sulfur atom, more preferably the group that splits off with a nitrogen atom. Further, those as enumerated as the preferable examples of the group that splits off with a nitrogen atom are more preferred in the same order as Y. Preferable examples of Y are further explained below.

Y is preferably an aromatic heterocyclic group having 1, 2, or 4 ring-forming nitrogen atom(s), or a heterocyclic group represented by the above-mentioned formula (LB) (the latter is particularly preferred), a group that splits off with an oxygen atom (particularly preferably aryloxy, acyloxy, heterocyclic oxy) and a group that splits off with a sulfur atom (preferably arylthio, heterocyclic thio, and particularly preferably heterocyclic thio).

Preferably, Y may be a photographically useful group. As the photographically useful group, a development inhibitor, a desilvering accelerator, a redox compound, a dye, a coupler and the like, or their precursors are enumerated. Y is more preferably a development inhibitor or a precursor thereof. Examples of the development inhibitor or the precursor thereof include those as enumerated in JP-A-2000-

17195. Preferable examples are the same as described therein.

In order to render the coupler inmobile in a light-sensitive material, at least one of Q, $R_1$, $R_4$, X and Y has preferably 8 to 50 carbon atoms, more preferably 10 to 40 carbon atoms in total respectively, including carbon atoms of substituent(s) that they may have.

Preferable specific examples of the coupler represented by formula (IB) according to the present invention are shown below. However, the present invention should not be construed as being limited to these compounds. The present invention includes tautomers having a hydrogen atom moved on a carbonyl group or a nitrogen-containing 6-membered ring.

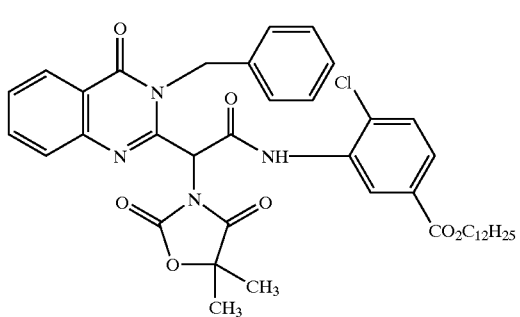
(1B)

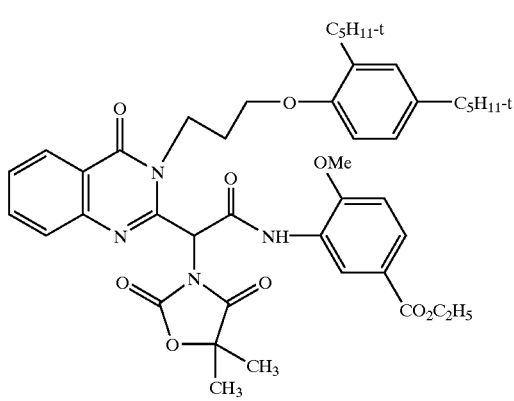
(2B)

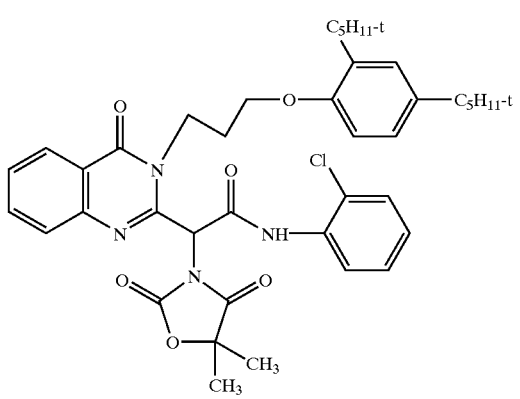
(3B)

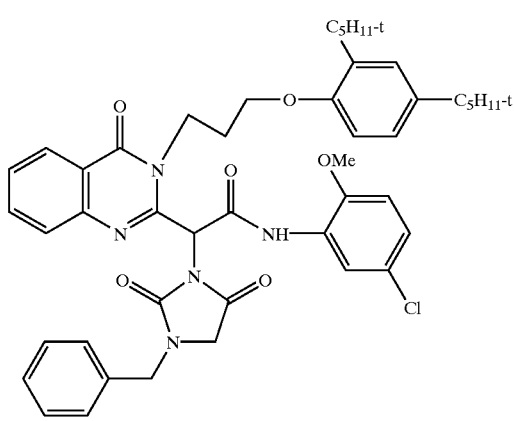
(4B)

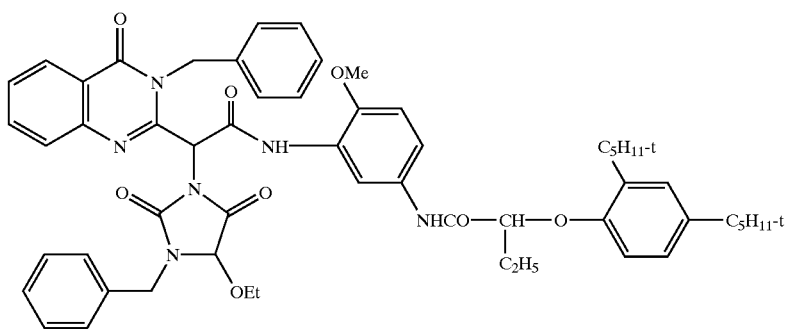
(5B)

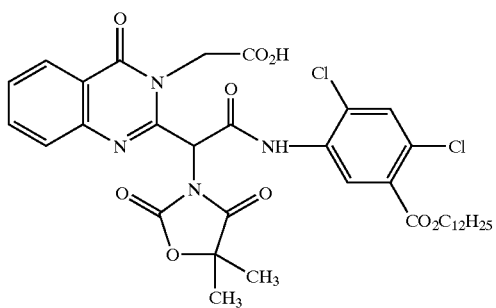
(6B)

-continued
(7B)
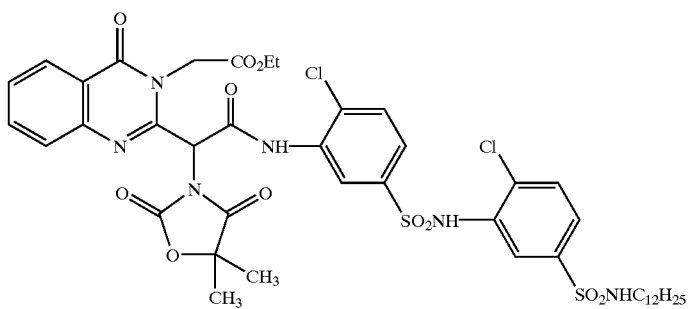
(8B)
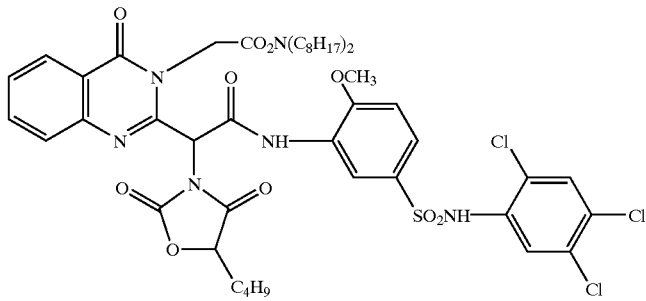
(9B)
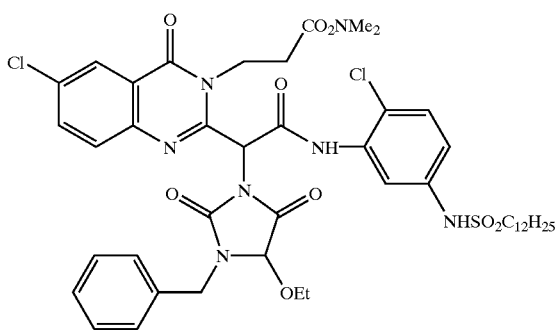
(10B)
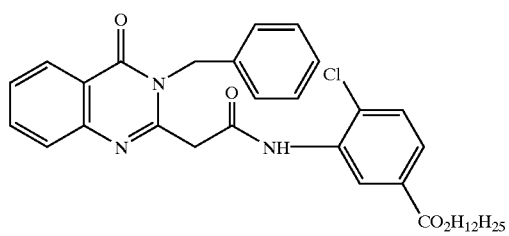
(11B)
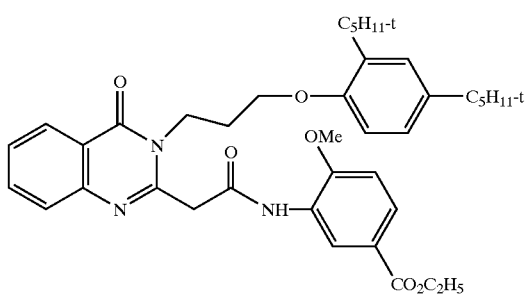
(12B)
(13B)
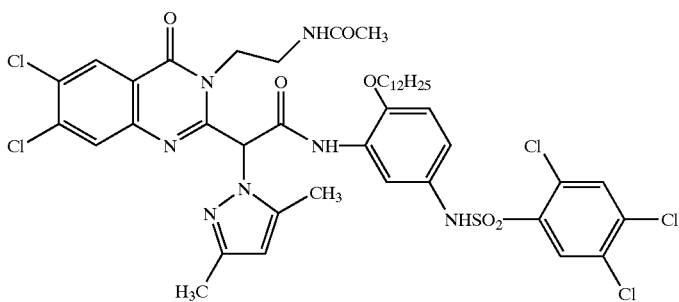

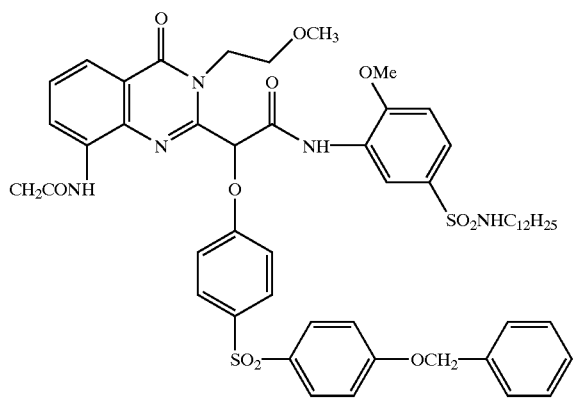
(14B)
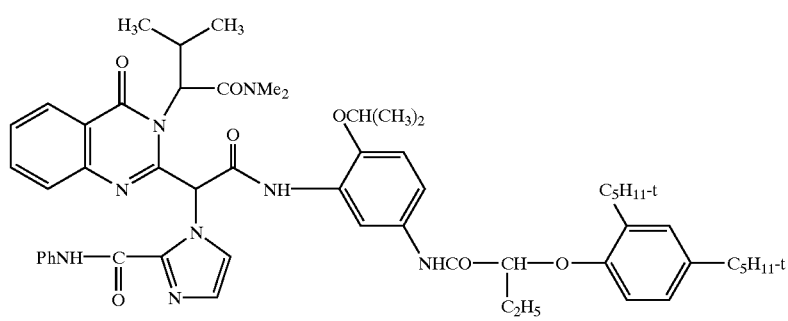
(15B)
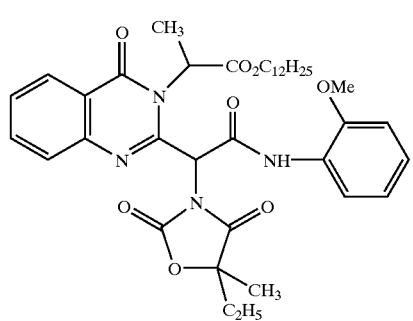
(16B)
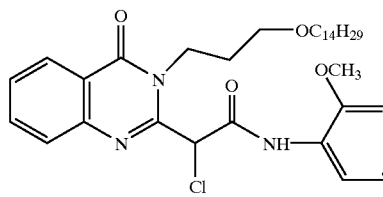
(17B)
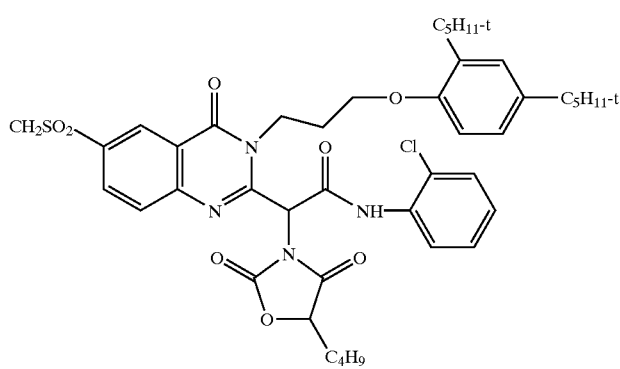
(18B)

-continued
(19B)
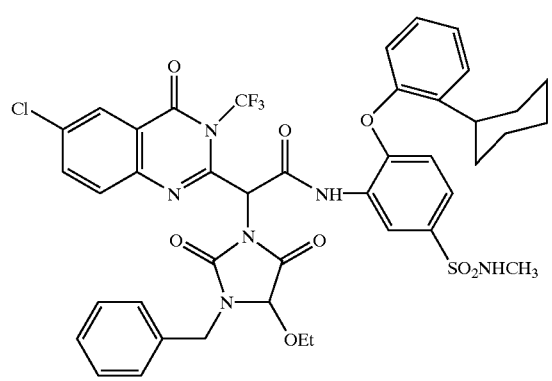
(20B)
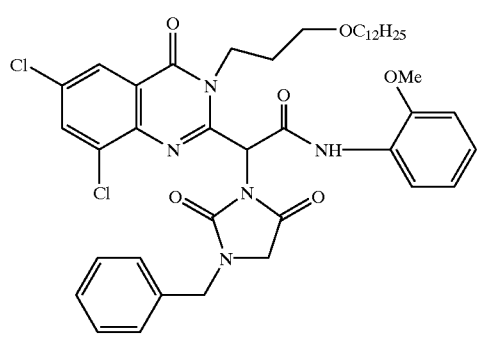
(21B)
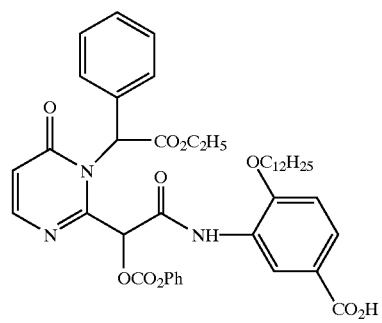
(22B)
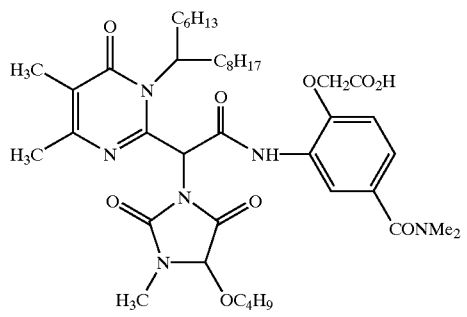
(23B)
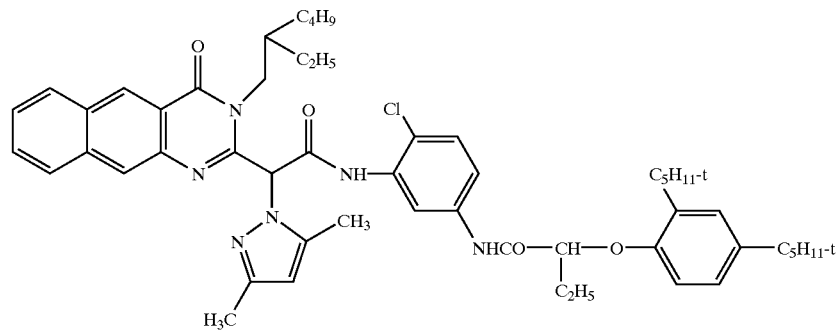
(24B)
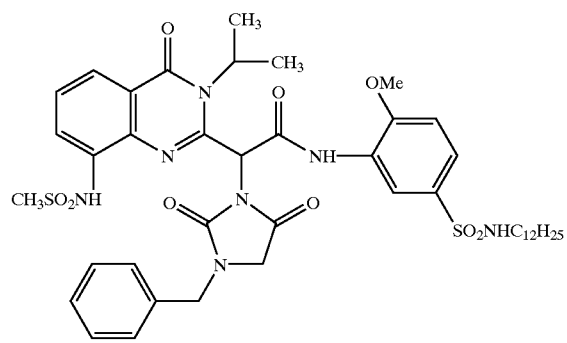

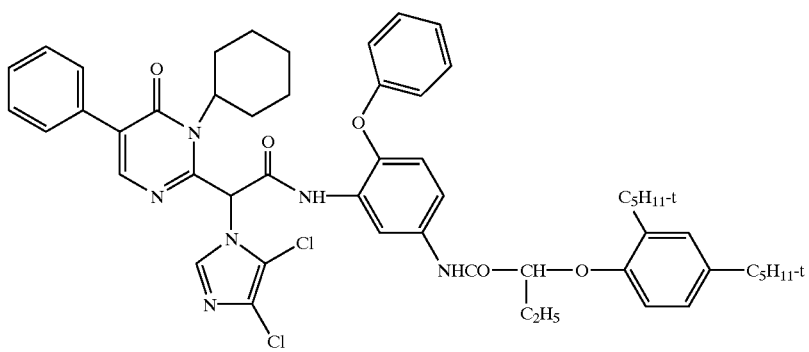
(25B)
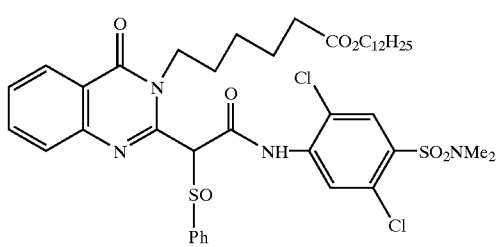
(26B)
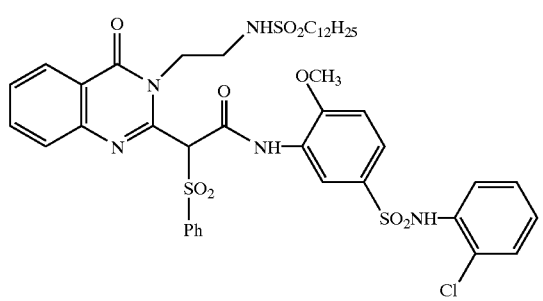
(27B)
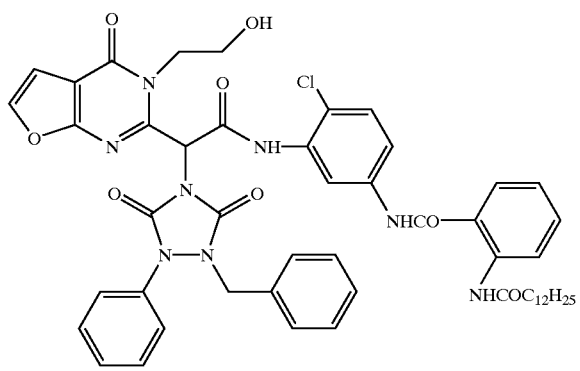
(28B)
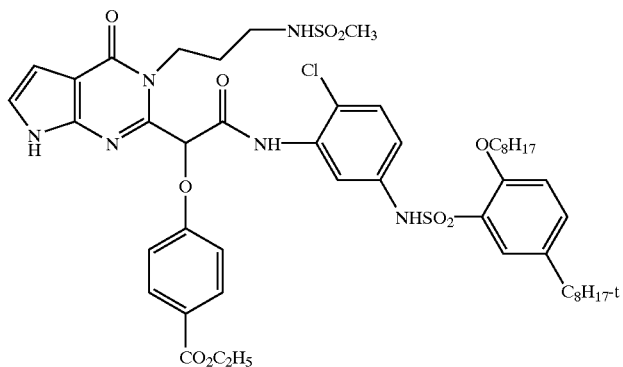
(29B)

-continued
(30B)
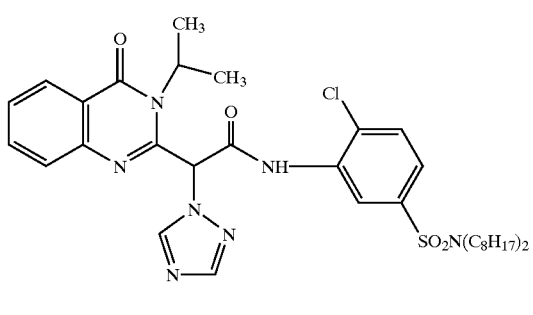
(31B)
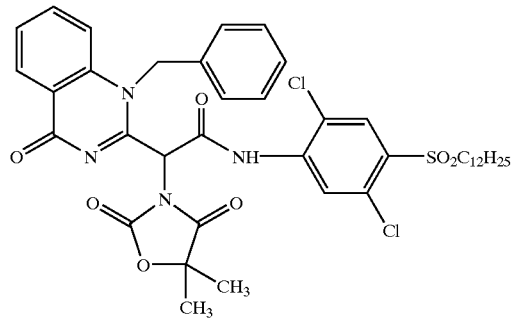
(32B)
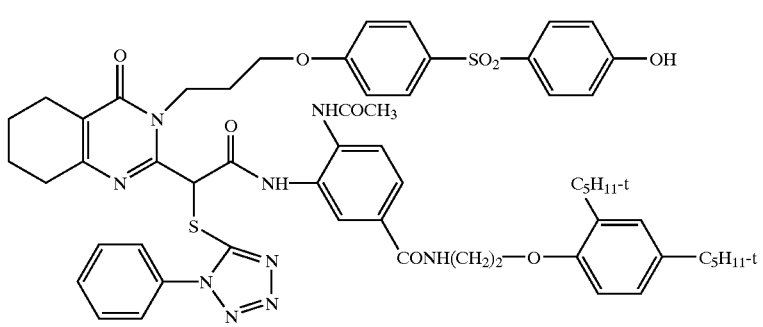
(33B)
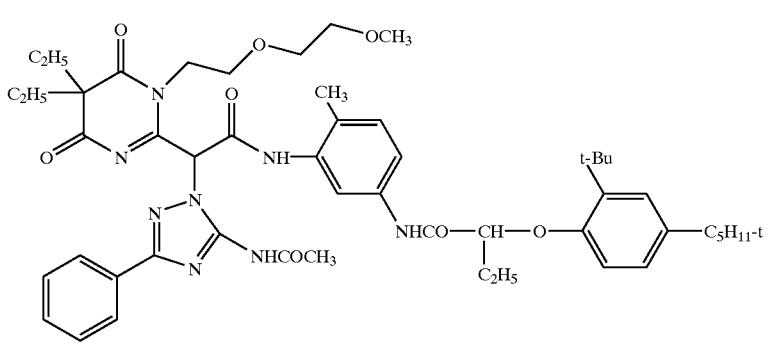
(34B)
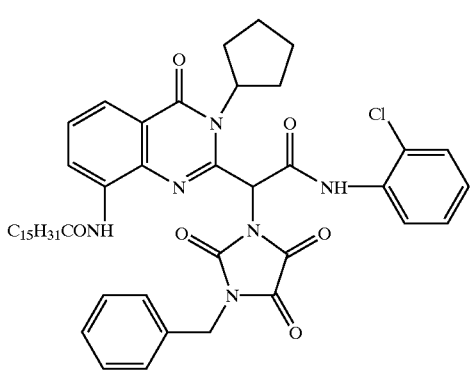

-continued
(35B)
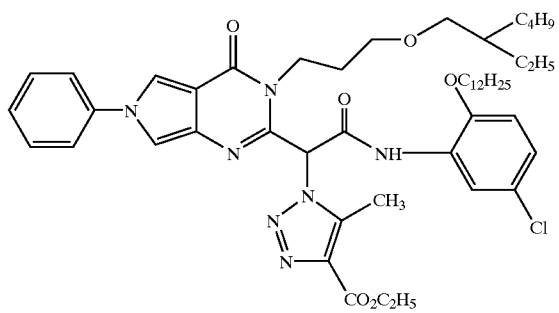
(36B)
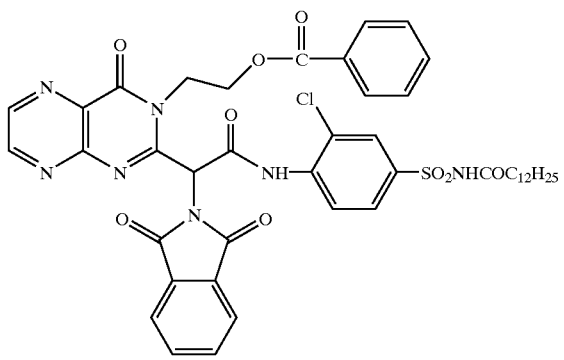
(37B)
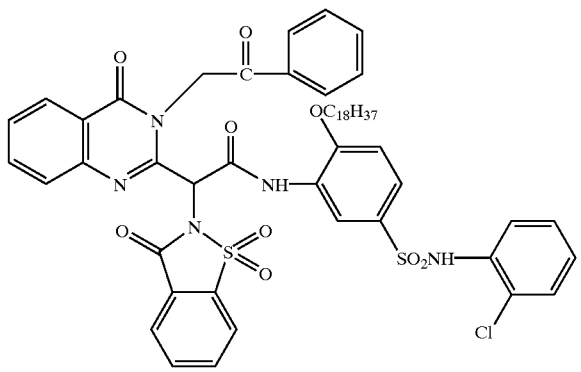
(38B)
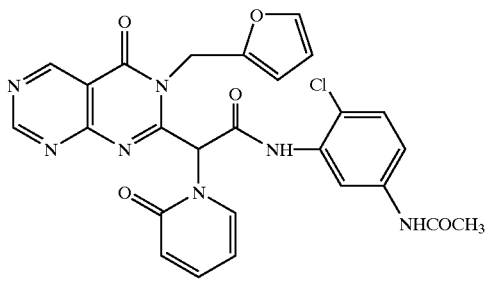

(39B)

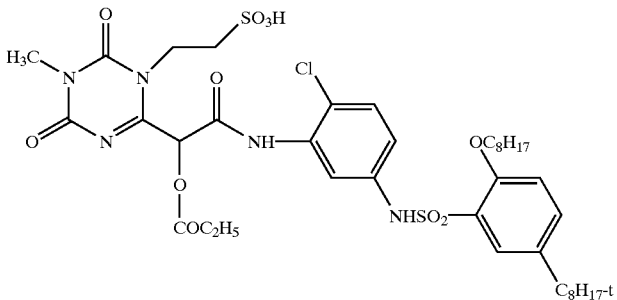

(40B)

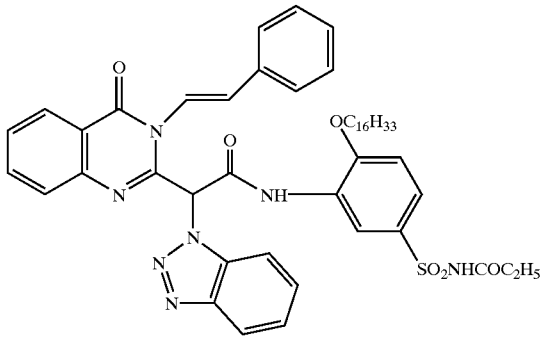

When any one of the exemplified compounds (which may also be referred to as dye-forming couplers) shown above is referred to in the following description, a number X put in parentheses, that is, (X) attached to the exemplified compound is used to express the compound as "the coupler (X)".

The following will describe specific synthetic examples of the compounds represented by formula (IB).

Synthetic Example 2-1

Synthesis of the Coupler (10B)

The coupler (10B) was synthesized according to the following route:

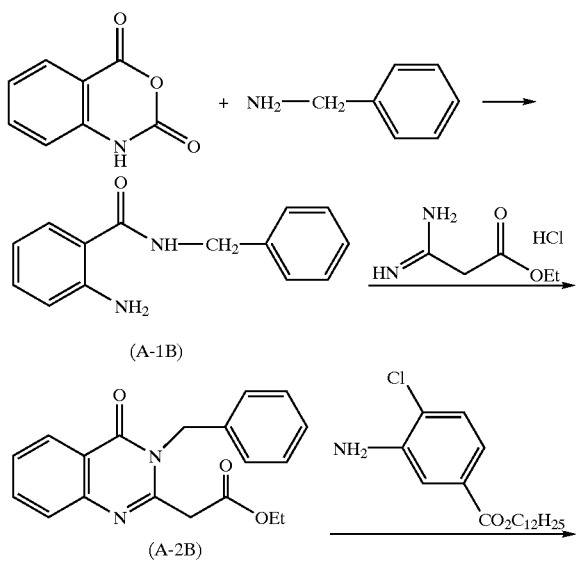

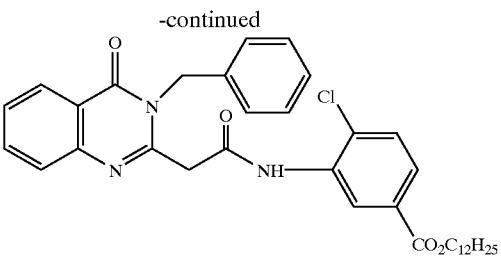

Coupler (10B)

32.2 g of benzylamine was added, drop-wise, with stirring, to 200 ml of an acetonitrile solution containing 48.9 g of isatoic acid anhydride, and the resulting mixture was stirred. The resulting mixture was heated up to 60° C. and further stirred for 10 minutes. Thereafter, ethyl acetate and water were added thereto, to separate an organic layer from an aqueous layer. The organic layer was dried with magnesium sulfate anhydride, and then the solvent was removed by vacuum distillation. Crystallization from a mixed solvent of ether and hexane gave 54.6 g of Compound (A-1B).

200 ml of an ethyl alcohol solution containing 24.9 g of Compound (A-1B), 21.6 g of hydrochloride of iminoether and 10.5 g of paratoluenesulfonic acid monohydrate was stirred for 3 hours with heating under reflux. After cooling, 21.6 g of hydrochloride of iminoether was added and further stirred with heating under reflux for 1 hour. Ethyl acetate and water were added to separate an organic layer from an aqueous layer. The organic layer was dried with magnesium sulfate anhydride. The solvent was removed by vacuum distillation. Crystallization from a mixed solvent of ether and hexane gave 33.6 g of Compound (A-2B).

50 ml of p-xylene solution containing 6.5 g of Compound (A-2B) and 6.5 g of 2-chloro-5-dodecyloxycarbonylaniline was stirred for 2 hours with heating under reflux. Further, 0.2 g of p-toluenesulfonic acid monohydrate was added and stirred for 4 hours with heating under reflux. Ethyl acetate and water were added to separate an organic layer from an aqueous layer. The organic layer was washed with 1-normal aqueous solution of hydrochloric acid and saturated brine, and then dried with magnesium sulfate anhydride. The solvent was removed by vacuum distillation. Crystallization from a mixed solvent of ethyl acetate and hexane gave 6.7 g of Coupler (10B).

Synthetic Example 2-2

Synthesis of the Coupler (1B)

The coupler (1B) was synthesized according to the following route:

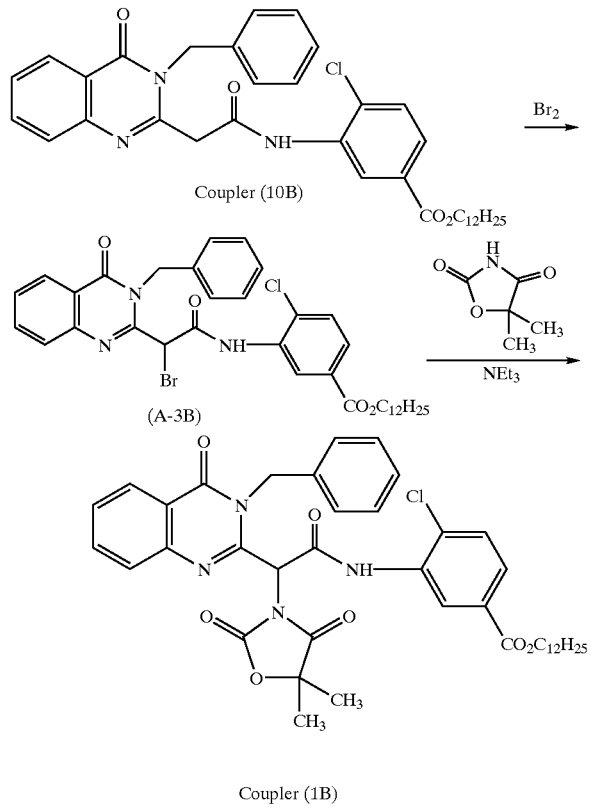

Coupler (1B)

To 70 ml of a methylene chloride solution containing 5.5 g of Coupler (10B), 15 ml of a methylene chloride solution containing 0.48 ml of bromine was added drop-wise under cooling with ice. After the mixture was stirred at room temperature for 30 minutes, methylene chloride and water were added to separate an organic layer from an aqueous layer. The organic layer was washed with saturated brine, and then dried with magnesium sulfate anhydride. The solvent was removed by vacuum distillation to obtain a crude product of Compound (A-3B).

To a solution which was prepared by dissolving 3.5 g of 5,5-dimethyl oxazolidine-2, 4-dione and 3.8 ml of triethylamine in 50 ml of N, N-dimethyl acetoamide, a solution containing all the previously synthesized crude product of Compound (A-3B) dissolved in 50 ml of N,N-dimethyl acetoamide was added drop-wise over 10 minutes at room temperature, and then stirred for 1 hour at room temperature. Ethyl acetate and water were added to separate an organic layer from an aqueous layer. The organic layer was washed with 1 normal aqueous solution of potassium carbonate, 1 normal aqueous solution of hydrochloric acid and saturated brine, and then dried with magnesium sulfate anhydride. The solvent was removed by vacuum distillation. Purification of the residue by silica gel column chromatography using a mixed solvent of ethyl acetate and hexane as the eluate gave 4.0 g of Coupler (1B) as an amorphous product.

Synthetic Example 2-3

Synthesis of the Coupler (11B)

The coupler (11B) was synthesized according to the following route:

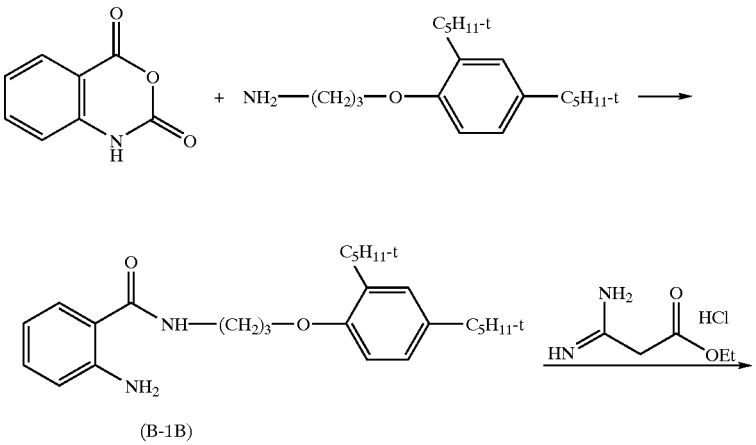

(B-1B)

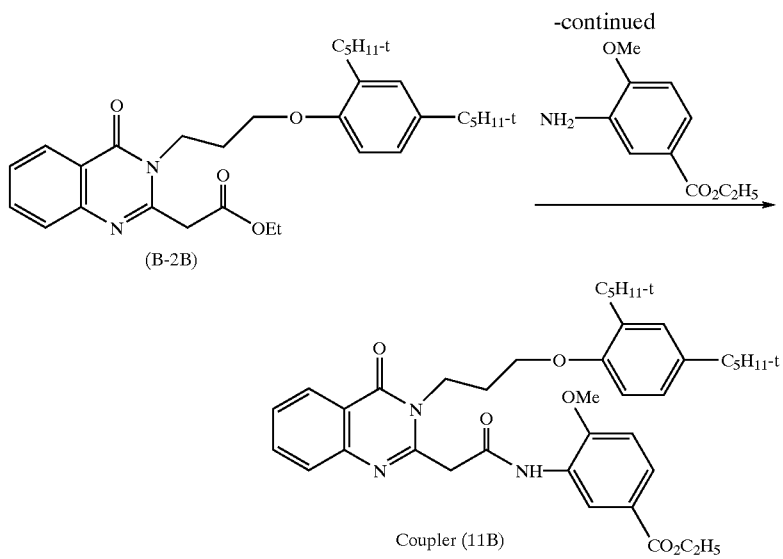

58.3 g of 3-(2,4-di-t-amyl-phenoxy)-propylamine was added with stirring to 200 ml of an acetonitrile solution containing 34.3 g of isatoic acid anhydride, and the resulting mixture was stirred. The resulting mixture was heated up to 40° C. and further stirred for 15 minutes. Thereafter, ethyl acetate and water were added to separate an organic layer from an aqueous layer. The organic layer was dried with magnesium sulfate anhydride, and then the solvent was removed by vacuum distillation, to obtain 81.3 g of Compound (B-1B) as an oily product.

200 ml of an ethyl alcohol solution containing 41.1 g of Compound (B-1B) and 39.1 g of hydrochloride of iminoether was stirred at 30° C. for 1 hour. 8.6 g of p-toluenesulfonic acid monohydrate was added and further stirred with heating under reflux for 2 hours. Ethyl acetate and water were added to separate an organic layer from an aqueous layer. The organic layer was dried with magnesium sulfate anhydride and then the solvent was removed by vacuum distillation. Crystallization from a methanol solvent gave 31.8 g of Compound (B-2B).

20 ml of p-xylene solution containing 10.1 g of Compound (B-2B) and 3.9 g of 2-methoxy-5-ethoxycarbonylaniline was stirred with heating under reflux for 4 hours. Ethyl acetate and water were added to separate an organic layer from an aqueous layer. The organic layer was washed with 1-normal aqueous solution of hydrochloric acid and saturated brine, and then dried with magnesium sulfate anhydride. The solvent was removed by vacuum distillation. Crystallization from a mixed solvent of ethyl acetate and hexane gave 6.3 g of Coupler (11B).

Synthetic Example 2-4

Synthesis of the Coupler (2B)

The coupler (2B) was synthesized according to the following route:

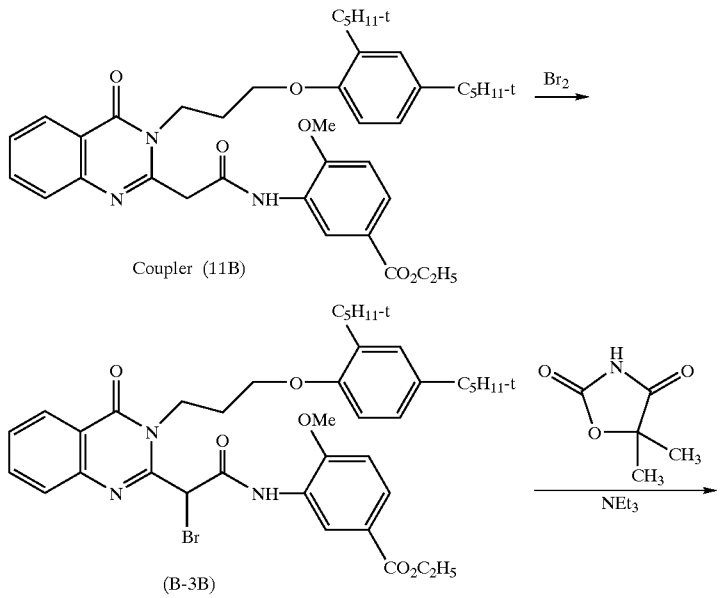

-continued

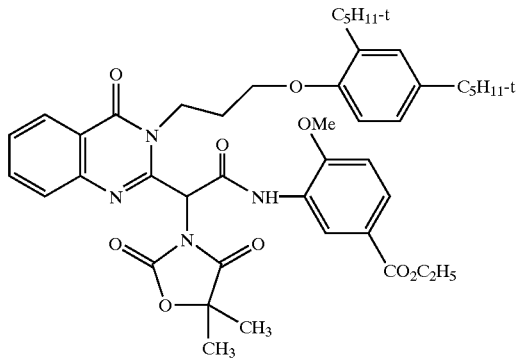

Coupler (2B)

To 120 ml of a methylene chloride solution containing 5.9 g of Coupler (11B), 20 ml of a methylene chloride solution containing 0.56 ml of bromine was added drop-wise under cooling with ice. After the mixture was stirred at room temperature for 30 minutes, methylene chloride and water were added to separate an organic layer from an aqueous layer. The organic layer was washed with saturated brine, and then dried with magnesium sulfate anhydride. The solvent was removed by vacuum distillation to obtain a crude product of Compound (B-3B).

To a solution which was prepared by dissolving 4.3 g of 5,5-dimethyloxazolidine-2,4-dione and 4.6 ml of triethylamine in 50 ml of N,N-dimethyl acetoamide, a solution containing all the previously synthesized crude product of Compound (B-3B) dissolved in 50 ml of N,N-dimethyl acetoamide was added drop-wise over 10 minutes at room temperature, and then stirred for 1 hour at room temperature. Ethyl acetate and water were added to separate an organic layer from an aqueous layer. The organic layer was washed with 1 normal aqueous solution of potassium carbonate, 1 normal aqueous solution of hydrochloric acid and saturated brine, and then dried with magnesium sulfate anhydride. The solvent was removed by vacuum distillation. The residue was purified by silica gel column chromatography using a mixed solvent of ethyl acetate and hexane as the eluate. Crystallization from methanol gave 4.1 g of Coupler (2B).

The dye-forming couplers of the present invention are explained above, referring to the formulae (IA) and (IB) as examples, and these explanations, as they are, can also be applied to the formula (I) that includes said formulae (IA) and (IB).

Silver Halide Photographic Light-sensitive Material

The light-sensitive material of the present invention is a silver halide photographic light-sensitive material, in which at least one light-sensitive layer is formed on a support, and the light-sensitive material contains the dye-forming coupler that is the compound represented by formula (I) of the present invention (for example, the compound represented by formula (IA) or (IB); the same is applied hereinafter), in at least one layer of the light-sensitive layer(s). The coupler is generally contained in a hydrophilic colloid layer composed of an ordinary gelatin binder. An ordinary light-sensitive material can be made by providing light-sensitive emulsion layers (light-sensitive layers) composed of at least one blue-sensitive silver halide emulsion layer, at least one green-sensitive silver halide emulsion layer, and at least one red-sensitive silver halide emulsion layer, on a support. The order of these light-sensitive layers may be selected arbitrarily. An infrared ray-sensitive silver halide emulsion layer may be used instead of at least one of the above-mentioned light-sensitive emulsion layers. Color reproduction based on subtractive color processes can be performed by incorporating, into each of these light-sensitive emulsion layers, a silver halide emulsion having sensitivity in the corresponding wavelength range, and a coupler for forming a dye having a color complementary to the color of sensitizing light. However, the light-sensitive emulsion layer and the developed hue of the coupler may not have a corresponding relationship as described above.

The dye-forming coupler represented by formula (I) can be incorporated into any one of the light-sensitive emulsion layers (preferably, the blue-sensitive silver halide emulsion layer or the green-sensitive silver halide emulsion layer, particularly preferably the blue-sensitive silver halide emulsion layer).

The dye-forming coupler represented by formula (I) is useful mainly as a yellow coupler or a magenta coupler, particularly as a yellow coupler, when combined with a p-phenylenediamine color-developing agent. Therefore, in the case that a p-phenylenediamine is used as a color-developing agent for the silver halide photographic light-sensitive material of the present invention, the dye-forming coupler represented by formula (I) is incorporated preferably into the yellow coupler- or magenta coupler-containing color-forming layer, particularly preferably into the yellow color-forming layer. In systems wherein a color-developing agent other than p-phenylenediamines is used, the dye-forming coupler represented by formula (I) is useful as a dye-forming coupler that can give a dye having various types of hue.

In the silver halide photographic light-sensitive material of the present invention, the coupler is added preferably in an amount of $1 \times 10^{-3}$ to 1 mole, more preferably in an amount of $2 \times 10^{-3}$ to $3 \times 10^{-1}$ mole, per mole of silver halide.

The coupler of the present invention may be incorporated in a light-sensitive material by various known dispersion processes. It is preferred to use an oil-in-water dispersion process in which first a compound is dissolved in a high-boiling-point organic solvent (in combination with a low-boiling-point organic solvent as occasion demands), thereby forming a solution and then the resulting solution is emulsified and dispersed in an aqueous gelatin solution, which is then added to a silver halide emulsion. Examples of the high-boiling-point organic solvent for use in the oil-in-water dispersion process are described in, for example, JP-A-5-313327, JP-A-5-323539, JP-A-5-323541, JP-A-6-258803, JP-A-8-262662, and U.S. Pat. No. 2,322,027. Further, the steps, effects and specific examples of latex polymers for impregnation, which are used in the latex dispersion process as one of polymer dispersion process, are described in, for example, U.S. Pat. No. 4,199,363, West German Patent Application (OLS) Nos. 2,541,274 and 2,541,230, JP-B-53-41091 ("JP-B" means examined Japanese patent publication), and European Patent Publication No. 029104. Further, dispersion processes using an organic solvent-soluble polymer are described in, for example, PCT International Publication WO 88/00723 and JP-A-5-150420. Methacrylate-series or acrylamide-series polymers are preferred. In particular, the use of acrylamide-series polymers is preferred, in view of enhancing image-fastness.

The term "high boiling point" herein used refers to a boiling point of 175° C. or more at ordinary pressure.

Examples of the high-boiling-point solvent for use in the present invention are described in, for example, U.S. Pat. No. 2,322,027. Specific examples of the high-boiling-point organic solvent having a boiling point of 175° C. or more at ordinary pressure include phthalic acid esters {e.g., dibutyl phthalate, dicyclohexyl phthalate, di-2-ethylhexyl phthalate, decyl phthalate, bis(2,4-di-tert-amylphenyl) phthalate, bis(2,4-di-tert-amylphenyl) iso-phthalate, bis(1,1-di-ethylpropyl) phthalate}, esters of phosphoric acid or phosphonic acid (e.g., triphenyl phosphate, tricresyl phosphate, 2-ethylhexyldiphenyl phosphate, tricyclohexyl phosphate, tri-2-ethlhexyl phosphate, tridodecyl phosphate, tributoxyethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecaneamide, N,N-diethyllaurylamide, N-tetradecylpyrrolidone), sulfonamides (e.g., N-butylbenzenesulfonamide), alcohols and phenols (e.g., isostearyl alcohol, 2,4-di-tert-amylphenol), aliphatic carboxylic acid esters (e.g., bis-(2-ethylhexyl) sebacate, dioctyl azelate, glycerol tributylate, isostearyl lactate, trioctyl citrate), aniline derivatives (e.g., N,N-dibutyl-2-butory-5-tert-octylaniline), hydrocarbons (e.g., paraffin, dodecylbenzene, diisopropylnaphthalene), and chlorinated paraffins. In particular, the foregoing phosphoric acid esters, and hydrogen-providing compounds described in JP-A-6-258803 and JP-A-8-262662 are preferably used, since they help to provide an excellent hue.

In order to reduce a load to environment, it is preferred to use compounds described in European Patent Nos. EP-969320A1 and EP-969321A1, in place of the foregoing phthalic acid esters. In addition to the above-mentioned compounds, tributyl citrate, pentaglycelol triesters and the like may be used.

The dielectric constant of the high-boiling-point organic solvent varies depending on the purpose for use, but it is preferably in the range of 2.0 to 7.0, more preferably in the range of 3.0 to 6.0.

The high-boiling-point organic solvent is used preferably in an amount of 0 to 10 times of the mass of the coupler, more preferably in an amount of 0 to 4 times thereof.

Further, as an auxiliary solvent, an organic solvent having a boiling point of 30° C. or more, preferably in the range of from 50° C. to about 160° C. may be used. Typical examples of the auxiliary solvent include ethyl acetate, butyl acetate, ethyl propionate, methyl ethyl ketone, cyclohexane, 2-ethoxyethyl acetate and dimethylformamide.

All or a part of the auxiliary solvent may be removed from an emulsified dispersion by means of a vacuum distillation, a noodle washing, an ultrafiltration, or the like, as occasion demands for the purpose of improving storage stability with the lapse of time in the state of the emulsified dispersion, or inhibiting a fluctuation in photographic properties or improving storage stability with the lapse of time of the final coating composition in which the emulsified dispersion is mixed with a silver halide emulsion.

The average particle size of the oleophilic fine particle dispersion thus obtained is preferably in the range of 0.001 to 1.0 μm, more preferably in the range of 0.05 to 0.30 μm, and most preferably in the range of 0.08 to 0.20 μm. The average particle size can be determined with a measuring device such as Coulter submicron particle analyzer model N4 (trade name, made by Coulter Electronics Co., Ltd.). If the average particle size of the oleophilic fine particles dispersion is too large, such problems easily arise that a color-formation efficiency of a coupler is lessened, or gloss on the surface of a light-sensitive material deteriorates. In contrast, if the average particle size is too small, viscosity of the dispersion increases and consequently a handling becomes difficult at the time of production.

The amount to be used (in terms of mass ratio) of a dispersion of oleophilic fine particles composed of the coupler of the present invention to a dispersion medium is preferably in the range of 2 to 0.1, more preferably in the range of 1.0 to 0.2, per 1 part by mass of the dispersion medium. Examples of the dispersion medium include gelatin that is a typical example, and in addition thereto mention can be made of hydrophilic polymers, such as polyvinyl alcohol. The oleophilic fine-particle dispersion may contain various compounds, together with the coupler of the present invention, according to the purpose of use.

Other known photographic materials and additives may be used in the silver halide photographic light-sensitive material of the present invention.

For example, as a photographic support (base), any one of a transmissive type support and a reflective type support may be used. As the transmissive type support, it is preferred to use transparent supports, such as a cellulose nitrate film, and a transparent film of polyethylene terephthalate, or a polyester of 2,6-naphthalenedicarboxylic acid (NDCA) and ethylene glycol (EG), or a polyester of NDCA, terephthalic acid and EG, provided thereon with an information-recording layer such as a magnetic layer. As the reflective type support, it is especially preferable to use a reflective support having a substrate laminated thereon with a plurality of polyethylene layers or polyester layers (water-proof resin layers or laminate layers), at least one of which contains a white pigment such as titanium oxide.

A more preferable reflective support for use in the present invention is a support having a paper substrate provided with a polyolefin layer having fine holes, on the same side as silver halide emulsion layers. The polyolefin layer may be composed of multi-layers. In this case, it is more preferable for the support to be composed of a fine hole-free polyolefin (e.g., polypropylene, polyethylene) layer adjacent to a gelatin layer on the same side as the silver halide emulsion layers, and a fine hole-containing polyolefin (e.g., polypropylene, polyethylene) layer closer to the paper substrate. The density of the multi-layer or single-layer of polyolefin layer(s) existing between the paper substrate and photographic constituting layers is preferably in the range of 0.40 to 1.0 g/ml, more preferably in the range of 0.50 to 0.70 g/ml. Further, the thickness of the multi-layer or single-layer of polyolefin layer(s) existing between the paper substrate and photographic constituting layers is preferably in the range of 10 to 100 μm, more preferably in the range of 15 to 70 μm. Further, the ratio of thickness of the polyolefin layer(s) to the paper substrate is preferably in the range of 0.05 to 0.2, more preferably in the range 0.1 to 0.5.

Further, it is also preferable for enhancing rigidity (mechanical strength) of the reflective support, by providing a polyolefin layer on the surface of the foregoing paper substrate opposite to the side of the photographic constituting layers, i.e., on the back surface of the paper substrate. In this case, it is preferable that the polyolefin layer on the back surface be polyethylene or polypropylene, the surface of which is matted, with the polypropylene being more preferable. The thickness of the polyolefin layer on the back surface is preferably in the range of 5 to 50 μm, more preferably in the range of 10 to 30 μm, and further the density thereof is preferably in the range of 0.7 to 1.1 g/ml. As to the reflective support for use in the present invention, preferable embodiments of the polyolefin layer provide on the paper substrate include those described in JP-A-10-333277, JP-A-10-333278, JP-A-11-52513, JP-A-11-65024, European Patent Nos. 0880065 and 0880066.

Further, it is preferred that the above-described waterproof resin layer contains a fluorescent whitening agent. Further, the fluorescent whitening agent also may be dispersed in a hydrophilic colloid layer of the light-sensitive material. Preferred fluorescent whitening agents that can be used, include benzoxazole series, coumarin series, and pyrazoline series compounds. Further, fluorescent whitening agents of benzoxazolylnaphthalene series and benzoxazolylstilbene series are more preferably used. The amount of the fluorescent whitening agent to be used is not particularly limited, and preferably in the range of 1 to 100 mg/m$^2$. When a fluorescent whitening agent is mixed with a waterproof resin, a mixing ratio of the fluorescent whitening agent to be used to the water-proof resin is preferably in the range of 0.0005 to 3% by mass, and more preferably in the range of 0.001 to 0.5% by mass of the resin.

Further, a transmissive type support or the foregoing reflective type support each having coated thereon a hydrophilic colloid layer containing a white pigment may be used as the reflective type support.

Furthermore, a reflective type support having a mirror plate reflective metal surface or a secondary diffusion reflective metal surface may be employed as the reflective type support.

As the support for use in the light-sensitive material of the present invention, a support of the white polyester type, or a support provided with a white pigment-containing layer on the same side as the silver halide emulsion layer, may be adopted for display use. Further, it is preferable for improving sharpness that an antihalation layer is provided on the silver halide demulsion layer side or the reverse side of the support. In particular, it is preferable that the transmission density of support is adjusted to the range of 0.35 to 0.8 so that a display may be enjoyed by means of both transmitted and reflected rays of light.

In the light-sensitive material of the present invention, in order to improve, e.g., sharpness of an image, a dye (particularly an oxonole-series dye) that can be discolored by processing, as described in European Patent No. 0337490 A2, pages 27 to 76, is preferably added to the hydrophilic colloid layer such that an optical reflection density at 680 nm in the light-sensitive material is 0.70 or more. It is also preferable to add 12% by mass or more (more preferably 14% by mass or more) of titanium oxide that is surface-treated with, for example, dihydric to tetrahydric alcohols (e.g., trimethylolethane) to a water-proof resin layer of the support.

The light-sensitive material of the present invention preferably contains, in their hydrophilic colloid layers, dyes (particularly oxonole dyes and cyanine dyes) that can be discolored by processing, as described in European Patent No. 0337490 A2, pages 27 to 76, in order to prevent irradiation or halation or to enhance safelight safety (immunity) or the like. Further, dyes described in European Patent No. 0819977 are also preferably used in the present invention.

Among these water-soluble dyes, some deteriorate color separation or safelight safety when used in an increased amount. Preferable examples of the dye which can be used and which does not deteriorate color separation include water-soluble dyes described in JP-A-5-127324, JP-A-5-127325 and JP-A-5-216185.

In the present invention, it is possible to use a colored layer that can be discolored during processing, in place of the water-soluble dye, or in combination with the water-soluble dye. The colored layer capable of being discolored with a processing to be used may contact with a light-sensitive emulsion layer directly, or indirectly through an interlayer containing an agent for preventing color-mixing during processing, such as hydroquinone and gelatin. The colored layer is preferably provided as a lower layer (closer to a support) with respect to the light-sensitive emulsion layer that develops the same primary color as the color of the colored layer. It is possible to provide colored layers independently, each corresponding to respective primary colors. Alternatively, only one layer or some layers selected from the above colored layers may be provided. In addition, it is possible to provide a colored layer subjected to coloring so as to match a plurality of primary-color regions. With respect to the optical reflection density of the colored layer, at the wavelength which provides the highest optical density in a range of wavelengths used for exposure (a visible light region from 400 nm to 700 nm for an ordinary printer exposure, and the wavelength of the light generated from the light source in the case of scanning exposure), the optical density is preferably within the range of 0.2 to 3.0, more preferably 0.5 to 2.5, and particularly preferably 0.8 to 2.0.

The colored layer described above may be formed by a known method. For example, there are a method in which a dye in a state of a dispersion of solid fine particles is incorporated in a hydrophilic colloid layer, as described in JP-A-2-282244, from page 3, upper right column to page 8, and JP-A-3-7931, from page 3, upper right column to page 11, left under column; a method in which an anionic dye is mordanted in a cationic polymer, a method in which a dye is adsorbed onto fine grains of silver halide or the like and fixed in the layer, and a method in which a colloidal silver is used, as described in JP-A-1-239544. As to a method of dispersing fine-powder of a dye in solid state, for example, JP-A-2-308244, pages 4 to 13 describes a method in which solid fine particles of dye which is at least substantially water-insoluble at the pH of 6 or less, but at least substantially water-soluble at the pH of 8 or more, are incorporated. The method of mordanting an anionic dye in a cationic polymer is described, for example, in JP-A-2-84637, pages 18 to 26. U.S. Pat. Nos. 2,688,601 and 3,459,563 disclose a method of preparing colloidal silver for use as a light absorber. Among these methods, preferred are the methods of incorporating fine particles of dye and of using colloidal silver.

Silver halide grains in the silver halide emulsion which can be used in the present invention, are preferably cubic or tetradecahedral crystal grains substantially having {100} planes (these grains may be rounded at the apexes thereof and further may have planes of higher order), or octahedral crystal grains. Alternatively, a silver halide emulsion in which the proportion of tabular grains having an aspect ratio of 2 or more and composed of {100} or {111} planes accounts for 50% or more in terms of the total projected area, can also be preferably used. The term "aspect ratio" refers to the value obtained by dividing the diameter of the circle having an area equivalent to the projected area of an individual grain by the thickness of the grain. In the present invention, cubic grains, or tabular grains having {100} planes as major faces, or tabular grains having {111} planes as major faces are preferably used.

As a silver halide emulsion which can be used in the present invention, for example, a silver chloride, silver bromide, silver iodobromide, or silver chloro(iodo)bromide emulsion may be used. It is preferable for a rapid processing to use a silver chloride or silver chlorobromide emulsion having a silver chloride content of 95 mole % or greater, more preferably a silver halide emulsion having a silver chloride content of 98 mole % or greater. Especially preferred of these silver halide emulsions are those containing silver chloride grains having a silver bromide localized phase on the surface thereof, since both high sensitivity and stabilization of photographic properties are attained.

The silver bromide localized phase is preferably formed by epitaxial growth of the localized phase having a total silver bromide content of at least 10 mole % in the silver bromide localized phase. A silver bromide content of the silver bromide localized phase is preferably in the range of 10 to 60 mole %, and most preferably in the range of 20 to 50 mole %. The silver bromide localized phase is preferably composed of silver having population of 0.1 to 5 mole %, more preferably 0.3 to 4 mole %, to the molar amount of entire silver which constitutes silver halide grains for use in the present invention. The silver bromide localized phase is preferably doped with complex ions of a metal of Group VIII in the periodic table, such as iridium (III) chloride, iridium (III) bromide, iridium (IV) chloride, sodium hexachloroiridate (III), potassium hexachloroiridate (IV), hexaammineiridium (IV) salts, trioxalatoiridium (III) salt, and trioxalatoiridium (IV) salt. The amount of these compounds to be added can be varied in a wide range depending on the purposes for use, and it is preferably in the range of 10 to 10 mole, per mole of silver halide.

In a silver halide emulsion for use in the present invention, various kinds of polyvalent metal ion impurities other than iridium may be incorporated, during grain formation or in the course of physical ripening of the emulsion. As for examples of the impurities to be used, salts or complex salts of metals of Group VIII of the periodic table, such as iron, ruthenium, osmium, rhenium, rhodium, cadmium, zinc, lead, copper and thallium, may be used in combination thereof. In the present invention, compounds of metals, such as iron, ruthenium, osmium and rhenium, which have at least four cyano ligands, are particularly preferred, since high-illumination-intensity sensitivity is further enhanced and latent-image sensitization is also inhibited. Iridium compounds provide an outstanding effect on the high-illumination intensity exposure suitability. The amount of these compounds to be added can be varied in a wide range depending on the purposes, and it is preferably in the range of $10^{-9}$ mole to $10^{-2}$ mole, per mole of silver halide.

The silver halide grains contained in the silver halide emulsion for use in the present invention have an average grain size (the grain size herein refers to the diameter of a circle equivalent to the projected area of an individual grain, and the number average is taken as the average grain size) of preferably from 0.1 $\mu$m to 2 $\mu$m.

With respect to the distribution of sizes of these grains, a so-called monodisperse emulsion having a variation coefficient (the value obtained by dividing the standard deviation of the grain size distribution by the average grain size) of 20% or less, more preferably 15% or less, and further preferably 10% or less, is preferred. For obtaining wide latitude, it is also preferred to blend the above-described monodisperse emulsions in the same layer or to form a multilayer structure by multilayer-coating of the monodisperse emulsions.

Various compounds or precursors thereof can be contained in the silver halide emulsion for use in the present invention to prevent fogging from occurring or to stabilize photographic performance during manufacture, storage or photographic processing of the photographic material. Specific examples of compounds useful for the above purposes are disclosed in JP-A-62-215272, pages 39 to 72, and they can be preferably used. In addition, 5-arylamino-1,2,3,4-thiatriazole compounds (in which the aryl residual group has at least one electron-attractive group), as disclosed in European Patent No. 0447647, are also preferably used.

Further, in the present invention, in order to enhance stability of the silver halide emulsion, it is preferable to use hydroxamic acid derivatives described in JP-A-11-109576, cyclic ketones having a double bond both ends of which are substituted with an amino group or a hydroxyl group, in adjacent to a carbonyl group, as described in JP-A-11-327094 (particularly those represented by formula (SI) and the descriptions of paragraph numbers 0036 to 0071 of JP-A-11-327094 can be incorporated herein by reference), catechols and hydroquinones each substituted with a sulfo group, as described in JP-A-11-143011 (e.g., 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid, and salts thereof), water-soluble reducing agents represented by any of formulae (I) to (III) of JP-A-11-102045, and hydroxylamines represented by the formula (A) in U.S. Pat. No. 5,556,741 (the descriptions of column 4, line 56 to column 11, line 22 in the U.S. Pat. No. 5,556,741 can be preferably applied to the present invention, and incorporated herein by reference).

Spectral sensitization is generally carried out, for the purpose of imparting spectral sensitivity in a desired light wavelength region to the light-sensitive emulsion in each layer of the photographic material of the present invention.

Spectral sensitizing dyes which are used in the photographic material of the present invention for spectral sensitization of blue, green and red light regions, include, for example, those disclosed by F. M. Harmer, in *Heterocyclic Compounds—Cyanine Dyes and Related Compounds,* John Wiley & Sons, New York, London (1964). Specific examples of the compounds and spectral sensitization processes that are preferably used in the present invention include those described in JP-A-62-215272, from page 22, right upper column to page 38. In addition, the spectral sensitizing dyes described in JP-A-3-123340 are very preferred as red-sensitive spectral sensitizing dyes for silver halide emulsion grains having a high silver chloride content from the viewpoint of stability, adsorption strength and the temperature dependency of exposure, and the like.

The amount of these spectral sensitizing dyes to be added can be varied in a wide range depending on the occasion, and it is preferably in the range of $0.5 \times 10^{-6}$ mole to $1.0 \times 10^{-2}$ mole, more preferably in the range of $1.0 \times 10^{-6}$ mole to $5.0 \times 10^{-3}$ mole, per mole of silver halide.

The silver halide emulsion that can be used in the present invention is generally chemically sensitized. Chemical sensitization can be performed by utilizing a sulfur sensitization, represented by the addition of an unstable sulfur compound, noble metal sensitization represented by gold sensitization, and reduction sensitization, each singly or in combination thereof. Compounds that are preferably used in chemical sensitization include those described in JP-A-62-215272, from page 18, right lower column to page 22, right upper column. Of these chemical sensitization, gold-sensitized silver halide emulsion are particularly preferred, since fluctuation in photographic properties which occurs when scanning exposure to laser beams or the like is conducted, can be further reduced by gold sensitization. In order to conduct gold sensitization, compounds such as chloroauric acid or a salt thereof, gold thiocyanates, gold thiosulfates, and colloidal gold sulfide may be used. The amount of these compounds to be added can be varied in a wide range depending on the occasion, and it is generally in the range of $5 \times 10^{-7}$ mole to $5 \times 10^{-3}$ mole, preferably in the range of $1.0 \times 10^{-6}$ mole to $1 \times 10^{-4}$ mole, per mole of silver halide. In the present invention, gold sensitization may be used in combination with other sensitizing methods, for example, sulfur sensitization, selenium sensitization, tellurium sensitization, reduction sensitization, or noble metal sensitization using a noble metal compound other than gold compounds.

The silver halide photographic light-sensitive material of the present invention can be used for a color negative film, a color positive film, a color reversal film, a color reversal photographic printing paper, a color photographic printing paper and the like. Among these materials, the light-sensitive material of the present invention is preferably used for a color photographic printing paper.

The color photographic printing paper preferably has at least one yellow color-forming silver halide emulsion layer, at least one magenta color-forming silver halide emulsion layer, and at least one cyan color-forming silver halide emulsion layer, on a support. Generally, these silver halide emulsion layers are in the order, from the support, of the yellow color-forming silver halide emulsion layer, the magenta color-forming silver halide emulsion layer and the cyan color-forming silver halide emulsion layer.

However, another layer arrangement which is different from the above, may be adopted.

When, for example, the coupler represented by formula (I) functions as a yellow coupler, a yellow coupler-containing silver halide emulsion layer may be disposed at any position on a support. However, in the case where silver halide tabular grains are contained in the yellow coupler-containing layer, it is preferable that the yellow coupler-containing layer is positioned more apart from a support than at least one of a magenta coupler-containing silver halide emulsion layer and a cyan coupler-containing silver halide emulsion layer. Further, it is preferable that the yellow coupler-containing silver halide emulsion layer is positioned most apart from a support of other silver halide emulsion layers, from the viewpoint of color-development acceleration, desilvering acceleration, and reduction in a residual color due to a sensitizing dye. Further, it is preferable that the cyan coupler-containing silver halide emulsion layer is disposed in the middle of other silver halide emulsion layers, from the viewpoint of reduction in a blix fading. On the other hand, it is preferable that the cyan coupler-containing silver halide emulsion layer is the lowest layer, from the viewpoint of reduction in a light fading. Further, each of a yellow-color-forming layer, a magenta-color-forming layer and a cyan-color-forming layer may be composed of two or three layers. It is also preferable that a color-forming layer is formed by disposing a silver halide emulsion-free layer containing a coupler in adjacent to a silver halide emulsion layer, as described in, for example, JP-A-4-75055, JP-A-9-114035, JP-A-10-246940, and U.S. Pat. No. 5,576,159.

Preferred examples of silver halide emulsions and other materials (additives or the like) for use in the present invention, photographic constitutional layers (arrangement of the layers or the like), and processing methods for processing the photographic materials and additives for processing are disclosed in JP-A-62-215272, JP-A-2-33144 and European Patent No. 0355660 A2. Particularly, those disclosed in European Patent No. 0355660 A2 are preferably used. Further, it is also preferred to use silver halide color photographic light-sensitive materials and processing methods therefor disclosed in, for example, JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641 and European Patent Publication No. 0520457 A2.

In particular, as the above-described reflective support and silver halide emulsion, as well as the different kinds of metal ions to be doped in the silver halide grains, the storage stabilizers or antifogging agents of the silver halide emulsion, the methods of chemical sensitization (sensitizers), the methods of spectral sensitization (spectral sensitizing dyes), the cyan, magenta, and yellow couplers and the emulsifying and dispersing methods thereof, the dye-image stability-improving agents (stain inhibitors and discoloration inhibitors), the dyes (colored layers), the kinds of gelatin, the layer structure of the light-sensitive material, and the film pH of the light-sensitive material, those described in the patent publications as shown in the following Table 1 are preferably used in the present invention.

TABLE 1

| Element | JP-A-7-104448 | JP-A-7-77775 | JP-A-7-301895 |
|---|---|---|---|
| Reflective-type bases | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |

TABLE 1-continued

| Element | JP-A-7-104448 | JP-A-7-77775 | JP-A-7-301895 |
|---|---|---|---|
| Different metal ion species | Column 74, lines 19 to 44 | Column 46, line 30 to Column 47, line 5 | Column 80, line 29 to Column 81, line 6 |
| Storage stabilizers or antifoggants | Column 75, lines 9 to 18 | Column 47, lines 20 to 29 | Column 18, line 11 to Column 31, line 37 (Especially, mercaptoheterocyclic compounds) |
| Chemical sensitizing methods (Chemical sensitizers) | Column 74, line 45 to Column 75, line 6 | Column 47, lines 7 to 17 | Column 81, lines 9 to 17 |
| Spectrally sensitizing methods (Spectral sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Column 63, line 3 to Column 64, line 11 | Column 31, line 34 to Column 77, line 44 and column 88, lines 32 to 46 |
| Emulsifying and dispersing methods of couplers | Column 71, line 3 to Column 72, line 11 | Column 61, lines 36 to 49 | Column 87, lines 35 to 48 |
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (coloring layers) | Column 77, line 42 to Column 78, line 41 | Column 7, line 14 to Column 19, line 42, and Column 50, line 3 to Column 51, line 14 | Column 9, line 27 to Column 18, line 10 |
| Kind of gelatins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| Film pH of light-sensitive materials | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As other cyan, magenta and yellow couplers which can be used in combination in the present invention, those disclosed in JP-A-62-215272, page 91, right upper column line 4 to page 121, left upper column line 6, JP-A-2-33144, page 3, right upper column line 14 to page 18, left upper column bottom line, and page 30, right upper column line 6 to page 35, right under column, line 11, European Patent No. 0355, 660 (A2), page 4 lines 15 to 27, page 5 line 30 to page 28 bottom line, page 45 lines 29 to 31, page 47 line 23 to page 63 line 50, are also advantageously used.

Further, it is preferred for the present invention to add compounds represented by formula (II) or (III) in WO 98/33760 or compounds represented by formula (D) described in JP-A-10-221825.

In the silver halide photographic light-sensitive material of the present invention, the dye-forming coupler represented by the above-described formula (I) may be used singly or in combination of two or more. In the case where the coupler of formula (I) is used as a yellow coupler, examples of another yellow coupler(s) which may be preferably used in combination with the above coupler of the present invention, include acylacetoamide-type yellow couplers in which the acyl group has a 3-membered to 5-membered cyclic structure, such as those described in European Patent No.0447969A1; malonic acid dianilide-type yellow couplers having a cyclic structure, as described in European Patent No.0482552A1; pyrrol-2- or 3-yl-, or indole-2- or 3-yl-carbonylacetic acid anilide-series couplers, as described in European Patent Nos. 0953870A1, 0953871A1, 0953872A1, 0953873A1, 0953874A1 and 0953875A1; acylacetamide-type yellow couplers having a dioxane structure, as those described in U.S. Pat. No. 5,118,599; in addition to the compounds described in the above-mentioned table. Above all, acylacetamide-type yellow couplers in which the acyl group is an 1-alkylcyclopropane-1-carbonyl group, or malonic acid dianilide-type yellow couplers in which one anilide constitutes an indoline ring is especially preferably used in combination with the above coupler of formula (I) of the present invention.

The cyan coupler that can be used in the present invention is preferably a phenol-series or naphthol-series cyan coupler, or a heterocyclic coupler.

The phenol coupler is preferably, for example, the cyan coupler represented by formula (ADF), as described in JP-A-10-333297, as well as any coupler in the above-mentioned table.

A 2,5-diacylaminophenol coupler, which is improved in hue and fastness of the resulting dye and which is described in U.S. Pat. No. 5,888,716, is preferably used.

As the heterocyclic coupler, the followings are preferred to use in combination with the coupler of the present invention: pyrroloazole-type cyan couplers described in EP 0488248 and EP0491197A1, and pyrazoloazole-type cyan couplers having a hydrogen bond group or an electron withdrawing group at its 6 position, as described in U.S. Pat. Nos. 4,873,183 and No. 4,916,051, particularly preferably pyrazoloazole-type cyan couplers having a carbamoyl group at its 6 position, as described in JP-A-8-171185, JP-A-8-311360 and JP-A-8-339060.

Among these cyan couplers, pyrroloazole-series cyan couplers represented by formula (I), as described in JP-A-11-282138, are particularly preferred. The descriptions in paragraph Nos. 0012 to 0059 of this publication, as well as the exemplified cyan couplers (1) to (47), can be applied to the present invention, and are preferably incorporated herein by reference.

In addition, the coupler of the present invention can also be used together with a diphenylimidazole-series cyan coupler described in JP-A-2-33144; a 3-hydroxypyridine-series cyan coupler (particularly a 2-equivalent coupler formed by allowing a coupler (42) of a 4-equivalent coupler to have a chlorine splitting-off group, and couplers (6) and (9), enumerated as specific examples are preferable) described in EP 0333185 A2; a cyclic active methylene-series cyan coupler (particularly couplers 3, 8, and 34 enumerated as specific examples are preferable) described in JP-A-64-32260; a pyrrolopyrazole-type cyan coupler described in European Patent No. 0456226 A1; or a pyrroloimidazole-type cyan coupler described in European Patent No. 0484909.

As the magenta coupler that can be used in the present invention, use can be made of a 5-pyrazolone-series magenta coupler or a pyrazoloazole-series magenta coupler, such as those described in the above-mentioned patent publications in the above Table. Among these, preferred are pyrazolotriazole couplers in which a secondary or tertiary alkyl group is directly bonded to the 2-, 3- or 6-position of the pyrazolotriazole ring, as described in JP-A-61-65245; pyrazoloazole couplers having a sulfonamido group in its molecule, as described in JP-A-61-65246; pyrazoloazole couplers having an alkoxyphenylsulfonamido ballasting group, as described in JP-A-61-147254; and pyrazoloazole couplers having an alkoxy or aryloxy group on its 6-position, as described in European Patent Nos. 0226849 A2 and 0294785 A, in view of the hue and stability of image to be formed therefrom and color-forming property of the couplers.

Particularly as the magenta coupler, pyrazoloazole couplers represented by formula (M-I), as described in JP-A-8-122984, are preferred. The descriptions of paragraph Nos. 0009 to 0026 of the patent publication can be entirely applied to the present invention and therefore are incorporated herein by reference.

In addition, pyrazoloazole couplers having a steric hindrance group at both the 3- and 6-positions, as described in European Patent Nos. 854384 and 884640, are also preferably used.

It is preferred that magenta or cyan couplers, as well as the (yellow) coupler of the present invention, are also pregnated into a loadable latex polymer (as described, for example, in U.S. Pat. No. 4,203,716) in the presence (or absence) of the high-boiling-point organic solvent described in the foregoing table, or they are dissolved in the presence (or absence) of the foregoing high-boiling-point organic solvent with a polymer insoluble in water but soluble in an organic solvent, and then emulsified and dispersed into an aqueous hydrophilic colloid solution.

The water-insoluble but organic solvent-soluble polymers that can be preferably used, include the homo-polymers and co-polymers disclosed in U.S. Pat. No. 4,857,449, from column 7 to column 15 and WO 88/00723, from page 12 to page 30. The use of methacrylate-series or acrylamide-series polymers, especially acrylamide-series polymers are more preferable in view of color-image stabilization and the like.

To suppress Blix discoloration (leuco dye reciprocity failure) by a bleaching solution or bleach-fixing solution, it is preferred to use a polymer described in JP-A-8-62797, JP-A-9-171240 and JP-A-9-329861, in the hydrophilic colloid layer.

In the present invention, known color mixing-inhibitors may be used. Among these compounds, those described in the following patent publications are preferred.

For example, high molecular weight redox compounds described in JP-A-5-333501; phenidone- or hydrazine-series compounds as described in, for example, WO 98/33760 and U.S. Pat. No. 4,923,787; and white couplers as described in, for example, JP-A-5-249637, JP-A-10-282615 and German Patent No. 19629142 A1, may be used. Further, in order to accelerate developing speed by increasing the pH of a developing solution, redox compounds described in, for example, German Patent Nos. 19,618,786 A1 and 19,806, 846 A1, European Patent Nos. 0,839,623 A1 and 0,842,975 A1, and French Patent No. 2,760,460 A1, are also preferably used.

In the present invention, as an ultraviolet ray absorbent, it is preferred to use compounds having a high molar extinction coefficient. Examples of these compounds include those having a triazine skeleton. Among these compounds, use can be made of those described, for example, in JP-A-46-3335, JP-A-55-152776, JP-A-5-197074, JP-A-5-232630, JP-A-5-307232, JP-A-6-211813, JP-A-8-53427, JP-A-8-234364, JP-A-8-239368, JP-A-9-31067, JP-A-10-115898, JP-A-10-147577, JP-A-10-182621, JP-T-8-501291 ("JP-T" means searched and published International patent application), European Patent No. 0,711,804 A1 and German Patent No. 19,739,797A.

In the present invention, examples of a decoloration inhibitor (anti-fading agent), a hue adjusting agent, and the like other than those described in the above Table, include vinyl compounds represented by formula (II), aniline derivatives represented by formula (III) having an oxygen-nitrogen bond or substituted with an alkoxy group, non-diffusible phenydone derivatives represented by formula (IV), nondiffusion carboxylic acids represented by formula (V), non-diffusible arylcarbamoyl derivatives represented by formula (VI), arylamide derivatives represented by formula (VII), and cyclic imide derivatives represented by formula (VIII), each of which are described in JP-A-11-258748, and all of them can be preferably used.

As the binder or protective colloid that can be used in the light-sensitive material of the present invention, gelatin is used advantageously, but another hydrophilic colloid can be used singly or in combination with gelatin. It is preferable for the gelatin for use in the present invention that the content of heavy metals, such as Fe, Cu, Zn and Mn, as impurities therein, is reduced to 5 ppm or below, more preferably 3 ppm or below.

Further, the amount of calcium contained in the light-sensitive material is preferably 20 mg/m$^2$ or less, more preferably 10 mg/m$^2$ or less, and most preferably 5 mg/m or less.

In the present invention, it is preferred to add an antibacterial (fungi-preventing) agent and antimold agent, as described in JP-A-63-271247, in order to destroy various kinds of molds and bacteria which propagate in a hydrophilic colloid layer and deteriorate the image.

Further, the pH of the film of the light-sensitive material is preferably in the range of 4.0 to 7.0, more preferably in the range of 4.0 to 6.5.

The light-sensitive material of the present invention can preferably be used, in addition to the printing system using a general negative printer, in a scanning exposure system using a cathode ray tube (CRT).

The cathode ray tube exposure apparatus is simpler and more compact, and therefore less expensive than a laser-emitting apparatus. Further, optical axis and color (hue) can easily be adjusted.

In a cathode ray tube that is used for image-wise exposure, various light-emitting substances which emit a light in the spectral region, are used as occasion demands. For example, any one of red-light-emitting substances, green-light-emitting substances, blue-light-emitting substances, or a mixture of two or more of these light-emitting substances may be used. The spectral regions are not limited to the above red, green and blue, and fluorophoroes which can emit a light in a region of yellow, orange, purple or infrared can be used. Particularly, a cathode ray tube that emits a white light by means of a mixture of these light-emitting substances is often used.

In the case where the light-sensitive material has a plurality of light-sensitive layers each having different spectral sensitivity distribution from each other and also the cathode ray tube has fluorescent substances which emit light in a plurality of spectral regions, exposure to a plurality of colors may be carried out at the same time. Namely, color image signals may be input into a cathode ray tube, to allow light to be emitted from the surface of the tube. Alternatively, a method in which an image signal of each of colors is successively input and light of each of colors is emitted in order, and then exposure is carried out through a film capable of cutting a color other than the emitted color, i.e., a surface successive exposure, may be used. Generally, among these methods the surface successive exposure is preferred from the viewpoint of high quality enhancement, because a cathode ray tube having high resolution can be used.

The light-sensitive material of the present invention can preferably be used in the digital scanning exposure system using monochromatic high density light, such as a gas laser, a light-emitting diode, a semiconductor laser, a second harmonic generation light source (SHG) comprising a combination of nonlinear optical crystal with a semiconductor or a solid state laser using a semiconductor laser as an excitation light source. It is preferred to use a semiconductor laser, or a second harmonic generation light source (SHG) comprising a combination of nonlinear optical crystal with a solid state laser or a semiconductor laser, to make a system more compact and inexpensive. In particular, to design a compact and inexpensive apparatus having a longer duration of life and high stability, use of a semiconductor laser is preferable; and it is preferred that at least one of exposure light sources should be a semiconductor laser.

When such a scanning exposure light source is used, the maximum spectral sensitivity wavelength of the light-sensitive material of the present invention can be arbitrarily set up in accordance with the wavelength of a scanning exposure light source to be used. Since oscillation wavelength of a laser can be made half, using a SHG light source obtainable by a combination of a nonlinear optical crystal with a semiconductor laser or a solid state laser using a semiconductor as an excitation light source, blue light and green light can be obtained. Accordingly, it is possible to have the spectral sensitivity maximum of a photographic material in normal three wavelength regions of blue, green and red.

The exposure time in such a scanning exposure is defined as the time necessary to expose the size of the picture element (pixel) with the density of the picture element being 400 dpi, and preferred exposure time is 10$^{-4}$ sec or less and more preferably 10$^{-6}$ sec or less.

The scanning exposure system that can preferably be used for the present invention is described in detail in the patent publications as shown in the above table.

With respect to the processing of the photographic material of the present invention, processing materials and processing methods, as disclosed in JP-A-2-207250, from page 26, right under column, line 1 to page 34, right upper column, line 9, and JP-A-4-97355, from page 5, left upper column, line 17 to page 18, right under column, line 20, can be preferably applied. Further, as preservatives which are used in the developing solution, compounds described in the patent publications as shown in the above table can be preferably used.

The present invention is preferably applied to a light-sensitive material having rapid processing suitability.

The term "color-developing time" as used herein refers to a period of time required from the beginning of dipping a light-sensitive material into a color-developing solution until the light-sensitive material is dipped into a blix solution in the subsequent processing step. In the case where a processing is carried out using, for example, an autoprocessor, the color-developing time is the sum total of a time in which a light-sensitive material has been dipped in a color-developing solution (so-called "time in the solution") and a time in which the light-sensitive material has been conveyed in air toward a bleach-fixing bath in the step subsequent to color development (so-called "time in the air"). Likewise, the term "blix time" as used herein refers to a period of time required from the beginning of dipping a light-sensitive material into a blix solution until the light-sensitive material is dipped into a washing bath or a stabilizing bath in the subsequent processing step. Further, the term "washing or stabilizing time" as used herein refers to a period of time required from the beginning of dipping a light-sensitive material into a washing solution or a stabilizing solution until the end of the dipping toward a drying step (so-called "time in the solution").

In the present invention, the color-developing time is preferably 60 sec or less, more preferably from 50 sec to 6 sec, further preferably from 30 sec to 6 sec. Likewise, the blix time is preferably 60 sec or less, more preferably from 50 sec to 6 sec, further preferably from 30 sec to 6 sec. Further, the washing or stabilizing time is preferably 150 sec or less, more preferably from 130 sec to 6 sec.

Examples of a development method applicable to the photographic material of the present invention after exposure, include a conventional wet system, such as a development method using a developing solution containing an alkali agent and a developing agent, and a development method wherein a developing agent is incorporated in the photographic material and an activator solution, e.g., a developing agent-free alkaline solution is employed for the development, as well as a heat development system using no processing solution. In particular, the activator method using a developing agent-free alkaline solution is preferred over the other methods, because the processing solution contains no developing agent, thereby it enables easy management and handling of the processing solution, and reduction in waste disposal load to make for environmental preservation.

The preferable developing agents or their precursors to be incorporated in the photographic materials in the case of adopting the activator method include the hydrazine compounds described in, for example, JP-A-8-234388, JP-A-9-152686, JP-A-9-152693, JP-A-9-211814 and JP-A-9-160193.

Further, the processing method in which the photographic material reduced in the amount of silver to be applied undergoes the image amplification processing using hydrogen peroxide (intensification processing), can be employed preferably. In particular, it is preferably to apply this processing method to the activator method. Specifically, the image-forming methods utilizing an activator solution containing hydrogen peroxide, as disclosed in JP-A-8-297354 and JP-A-9-152695 can be preferably used.

The processing with an activator solution is generally followed by a desilvering step in the activator method, but the desilvering step can be omitted in the case of applying the image amplification processing method to photographic materials of a low silver amount. In such a case, washing or stabilization processing can follow the processing with an activator solution to result in simplification of the processing process. On the other hand, when the system of reading the image information from photographic materials by means of a scanner or the like is employed, the processing form requiring no desilvering step can be applied, even if the photographic materials are those of a high silver amount, such as photographic materials for shooting.

The activator solution, desilvering solution (bleach-fixinging solution), washing solution and stabilizing solution for use in the present invention can contain known ingredients and can be used in conventional manners. Preferably, those described in *Research Disclosure*, Item 36544, pp. 536–541 (September 1994), and JP-A-8-234388 can be used in the present invention.

It is preferred to use a band stop filter, as described in U.S. Pat. No. 4,880,726, when the photographic material of the present invention is subjected to exposure with a printer. Color mixing of light can be excluded and color reproducibility is remarkably improved by the above means.

In the present invention, a yellow microdot pattern may be previously formed by pre-exposure before giving an image information, to thereby perform copy restraint, as described in European Patent Nos. 0789270 A1 and 0789480 A1.

The light-sensitive material of the present invention can be preferably used as a light-sensitive material for the advanced photo-system, which has a magnetic recording layer. The light-sensitive material of the present invention can be preferably used in a system wherein a small amount of water is used to perform heat-development, or in a complete dry system wherein no water is used to perform heat-development. Detailed descriptions on these systems are found, for example, in JP-A-6-35118, JP-A-6-17528, JP-A-56-146133, JP-A-60-119557, and JP-A-1-161236.

In the present invention, the wording "a silver halide photographic light-sensitive material" means to include not only a light-sensitive material for forming a color image but also a light-sensitive material for forming a monotone image, an example of which is a black and white image.

In case where the coupler of the present invention is applied to a color paper, light-sensitive material and the like described in JP-A-11-7109, particularly descriptions in paragraph numbers 0071 to 0087 in JP-A-11-7109 are preferable, and therefore the above descriptions in JP-A-11-7109 are incorporated herein by reference.

In case where the coupler of the present invention is applied to a color negative film, the descriptions at paragraph Nos. 0115 to 0217 of the specification of JP-A-11-305396 can be preferably applied thereto, and therefore incorporated herein by reference.

In case where the coupler of the present invention is applied to a color reversal film, the descriptions at paragraph Nos. 0018 to 0021 of the specification of JP-A-11-84601 can be preferably applied thereto, and therefore incorporated herein by reference.

Azomethine Dye

First, the compound represented by formula (IIA) of the present invention, among the compounds represented by formula (II) (herein they are also referred to as azomethine dye compounds) of the present invention, are explained in detail.

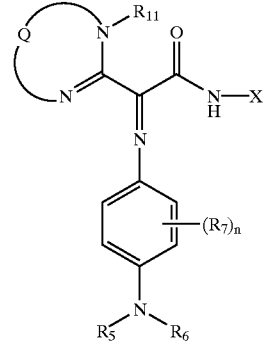

formula (IIA)

In formula (IIA), $R_{11}$, Q and X each have the same meanings as defined in formula (IA). Preferable examples of these $R_{11}$, Q and X are also the same as those in formula (IA).

In formula (IIA), $R_5$ and $R_6$ each represent a hydrogen atom or a substituent, or $R_5$ and $R_6$ may bond with each other to form a ring; $R_7$ represents a hydrogen atom or a substituent. n represents 0 (zero) or an integer of 1 to 4. When $R_5$, $R_6$ and $R_7$ each represent a substituent, examples of the substituent are the same as those exemplified above as the substituent that $R_{11}$ may have.

$R_7$s may be the same or different independently, or $R_7$s may be combined together to form a condensed ring, when n is 2 or more. Alternatively $R_7$ may bond together with $R_5$ or $R_6$ to form a condensed ring, n is 1 or more.

$R_7$ is preferably a hydrogen atom, a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, a substituted or unsubstituted alkoxy group having 1 to 30 carbon atoms, a halogen atom, or a substituted or unsubstituted acylamino group having 1 to 30 carbon atoms, more preferably a hydrogen atom or an alkyl group. Furthermore preferably, $R_7$ is a methyl group at the ortho position to the azomethine-nitrogen atom.

$R_5$ and $R_6$ each are preferably a substituted or unsubstituted alkyl group having 1 to 30 carbon atoms or a substituted or unsubstituted aryl group having 6 to 30 carbon atoms, more preferably an alkyl group. Furthermore preferably, one of $R_5$ and $R_6$ is an ethyl group, and the other is a 2-hydroxyethyl group or a 2-methanesulfonamidoethyl group.

Preferable specific examples of the azomethine dye represented by formula (IIA) according to the present invention are shown below. However, the present invention should not be construed as being limited to these compounds.

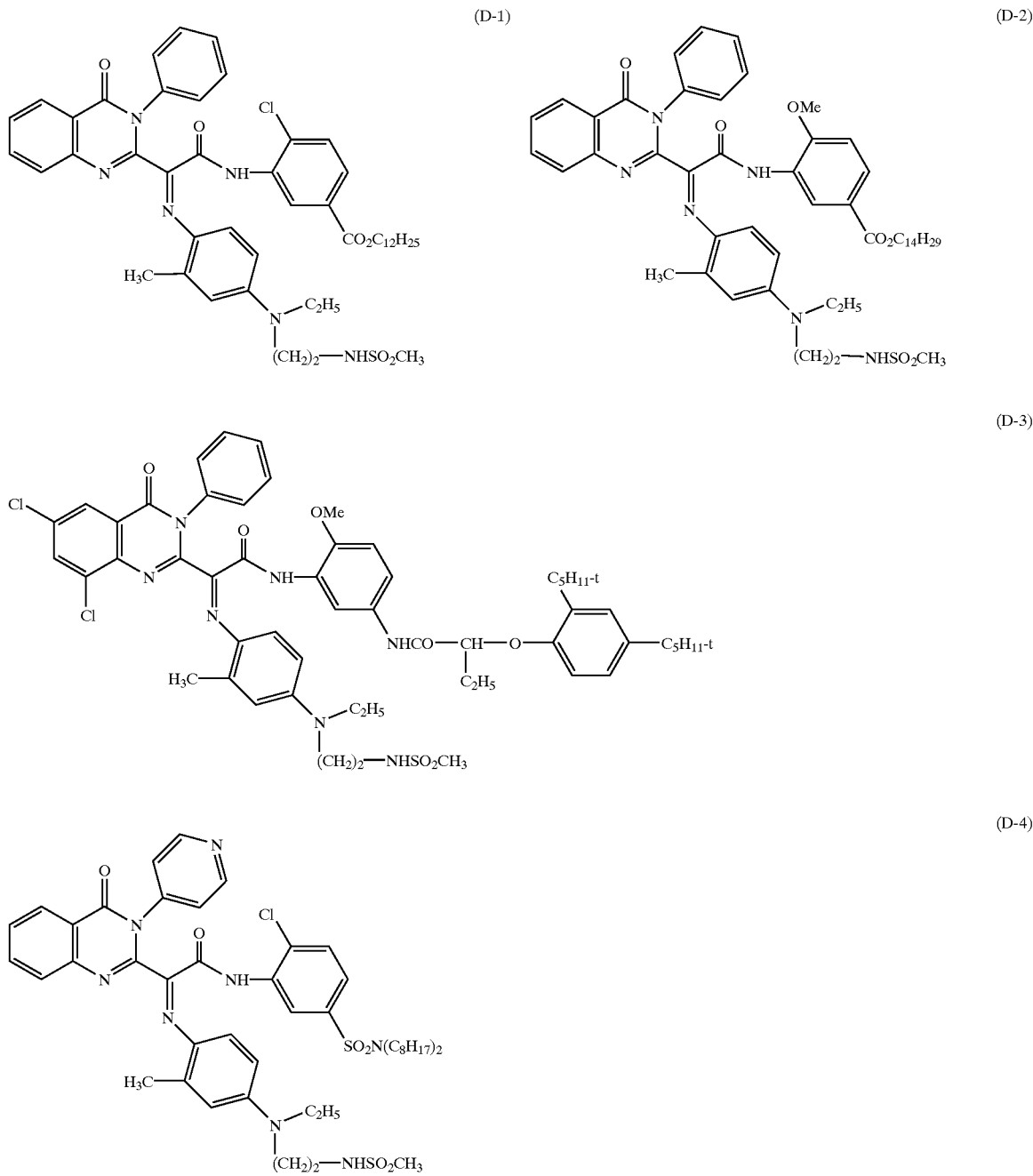

-continued
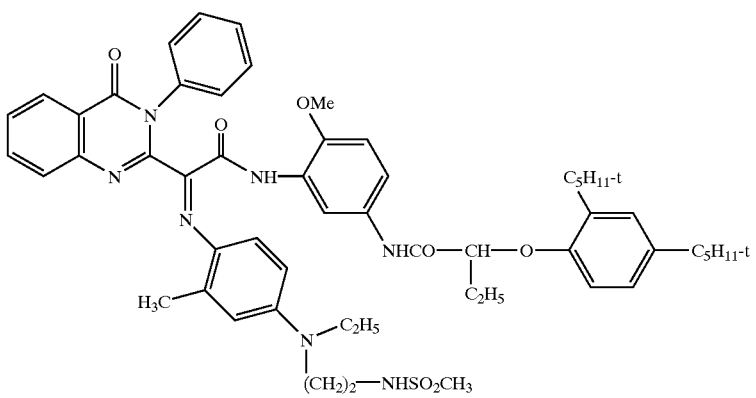
(D-5)
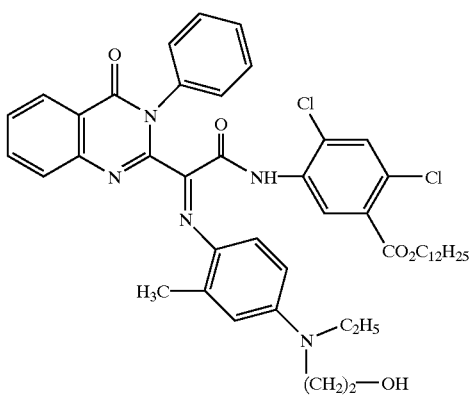
(D-6)
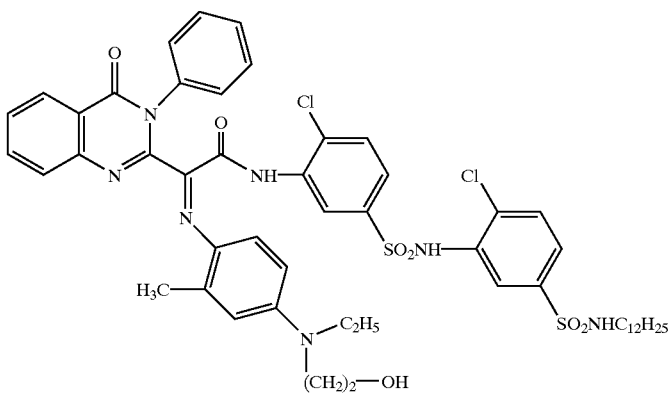
(D-7)
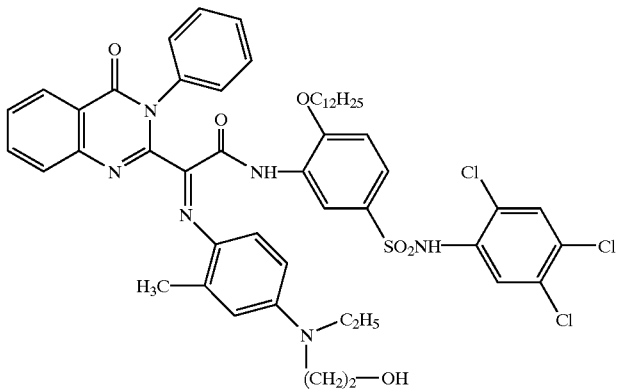
(D-8)

(D-9)
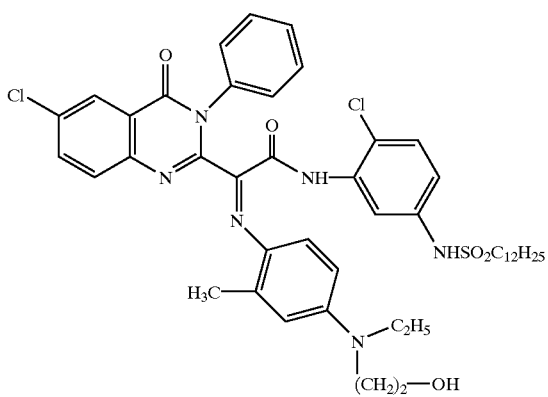
(D-10)
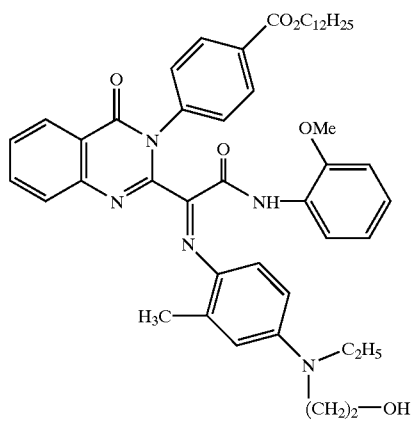
(D-11)
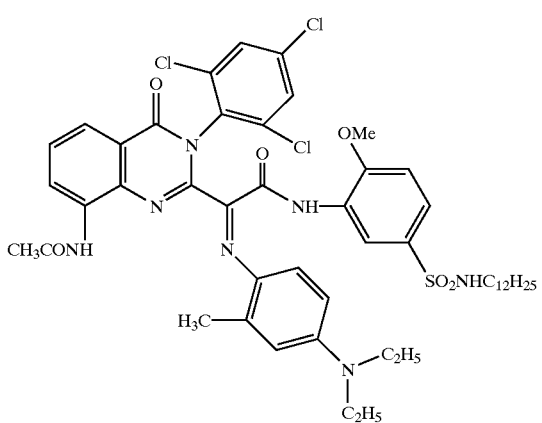
(D-12)
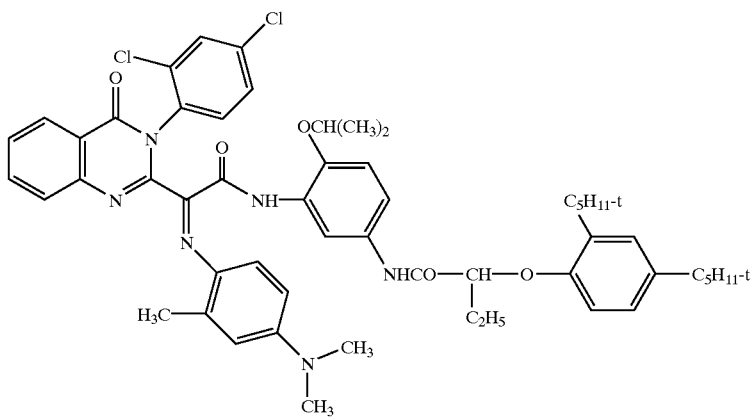
(D-13)
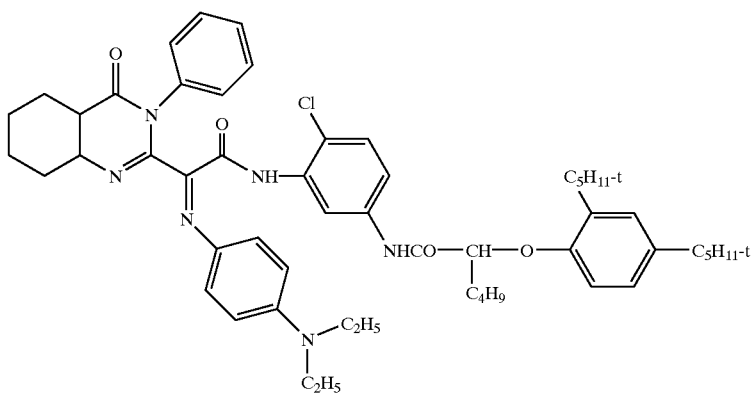

-continued
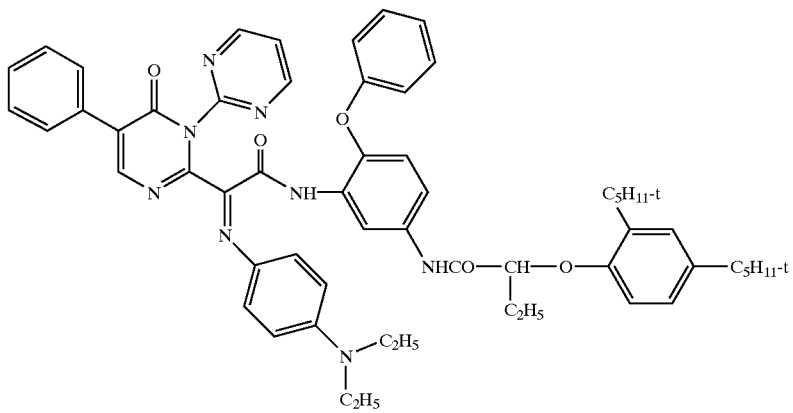
(D-14)
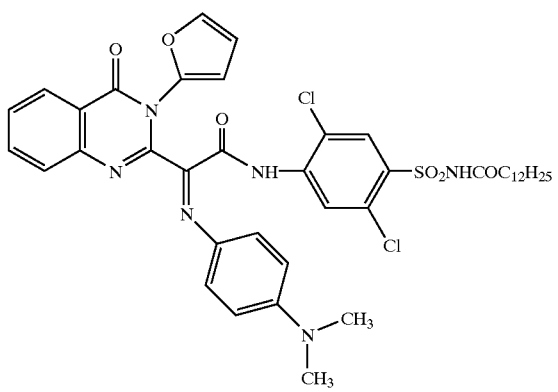
(D-15)
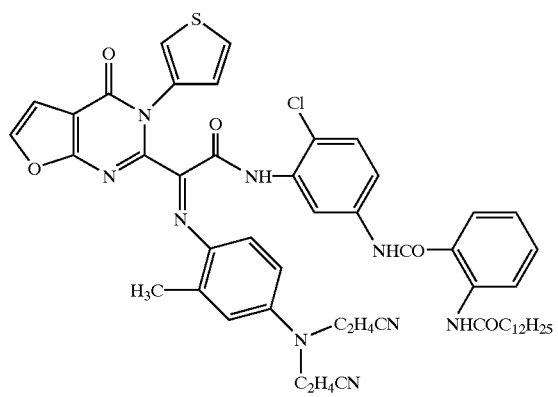
(D-16)
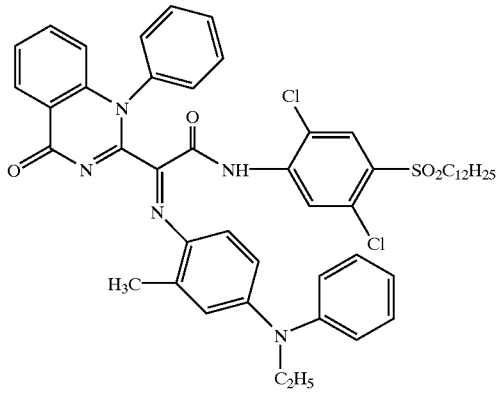
(D-17)
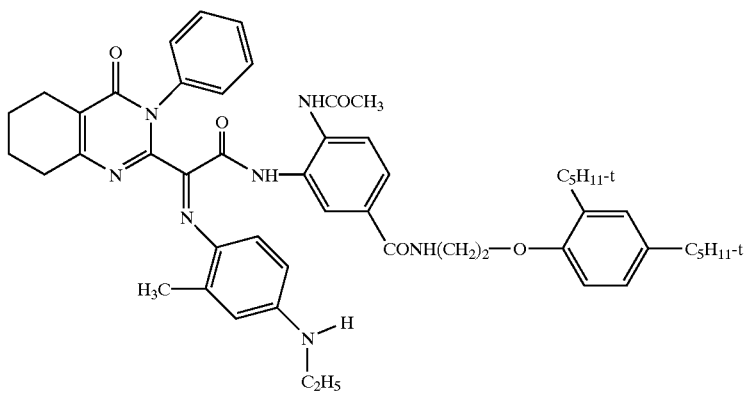
(D-18)

-continued
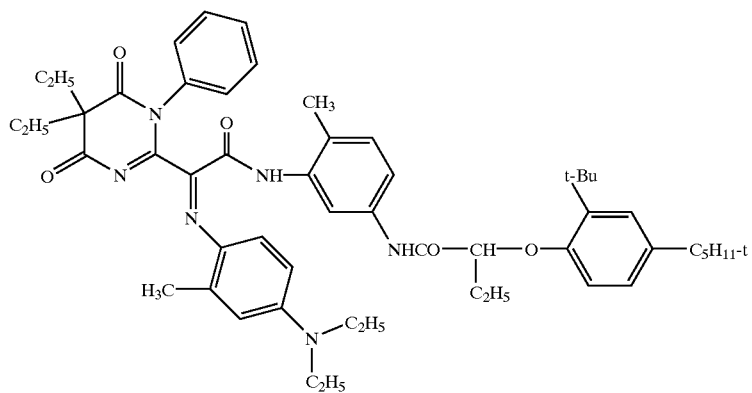
(D-19)
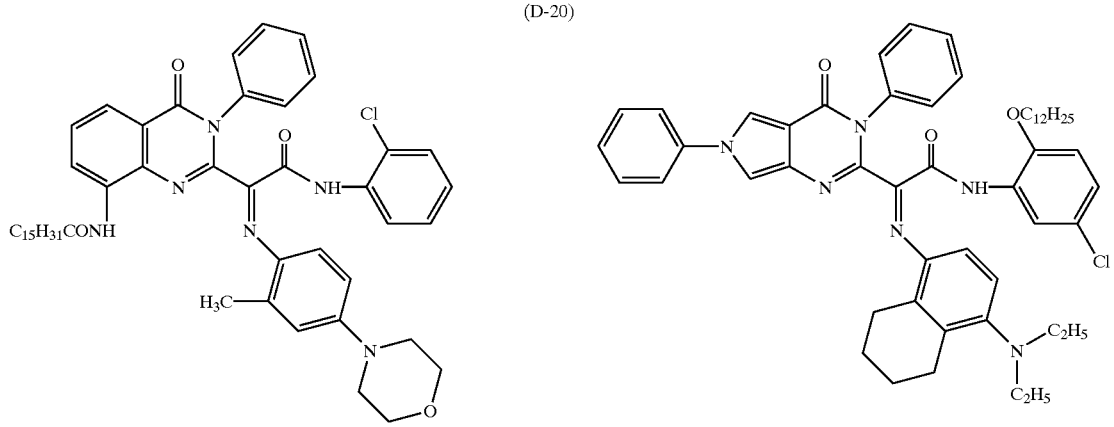
(D-20) (D-21)
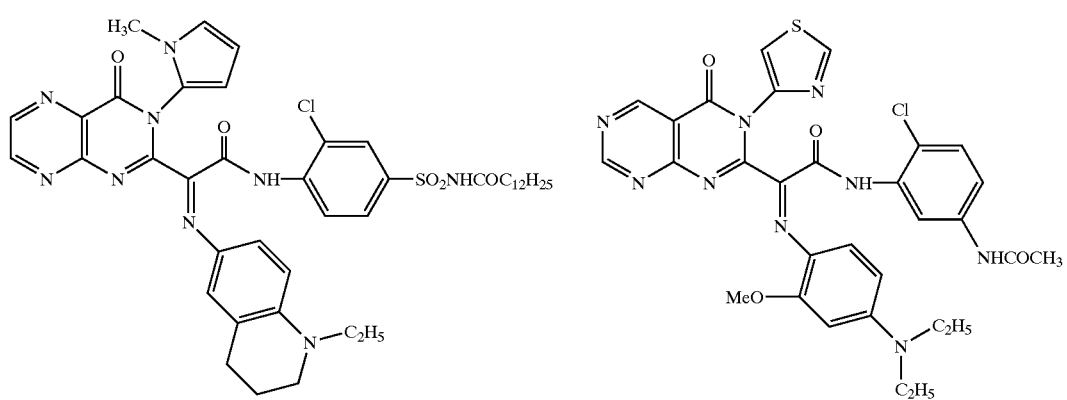
(D-22) (D-23)

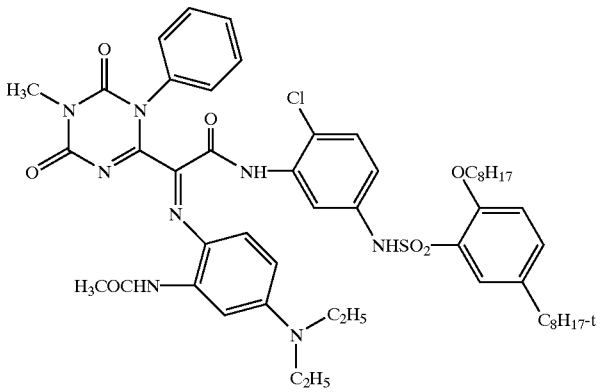

(D-24)

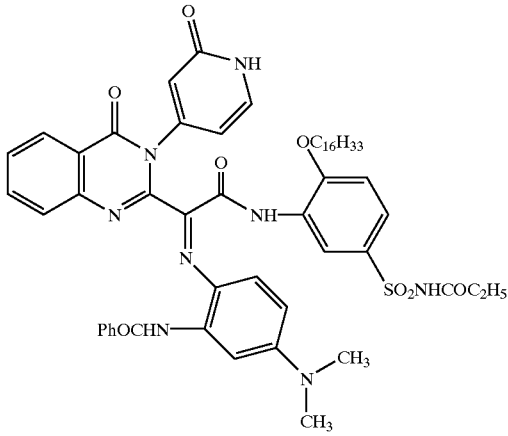

(D-25)

The compounds represented by formula (IIA) according to the present invention can be synthesized by a coupling reaction of the compound represented by formula (IA) according to the present invention, with an oxidized product of a phenylenediamine-series developing agent (particularly an N,N-di-substituted-p-phenylenediamine derivative). Besides, the compound of the formula (IIA) can be synthesized by reaction of the compound represented by formula (IA) in which Y is a hydrogen atom, with a 4-nitrosoaniline-series compound. Specific synthesis of the compounds is explained in the Examples described below.

Next, the compounds represented by formula (IIB), among the compounds represented by formula (II) of the present invention, are explained in detail.

formula (IIB)

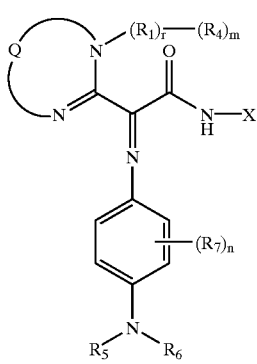

In formula (IIB), $R_1$, $R_4$, Q and X each have the same meanings as defined in formula (IB). Preferable examples of $R_1$, $R_4$, Q and X are also the same as those in formula (IB).

In formula (IIB), $R_5$ and $R_6$ each represent a hydrogen atom or a substituent, or $R_5$ and $R_6$ may bond with each other to form a ring; $R_7$ represents a hydrogen atom or a substituent. n represents 0 (zero) or an integer of 1 to 4. When $R_5$, $R_6$ and $R_7$ each represent a substituent, examples of the substituent are the same as those of $R_4$ described above.

$R_7$s may be the same or different independently, or $R_7$s may be combined together to form a condensed ring, when n is 2 or more. Alternatively $R_7$ may be combined together with $R_5$ or $R_6$ to form a condensed ring, when n is 1 or more.

$R_7$ is preferably a hydrogen atom, a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, a substituted or unsubstituted alkoxy group having 1 to 30 carbon atoms, a halogen atom, or a substituted or unsubstituted acylamino group having 1 to 30 carbon atoms, more preferably a hydrogen atom and an alkyl group. Furthermore preferably, $R_7$ is a methyl group at the ortho position to the azomethine-nitrogen atom.

$R_5$ and $R_6$ each are preferably a substituted or unsubstituted alkyl group having 1 to 30 carbon atoms or a substituted or unsubstituted aryl group having 6 to 30 carbon atoms, more preferably an alkyl group. Furthermore preferably, one of $R_5$ and $R_6$ is an ethyl group, and the other is a 2-hydroxyethyl group or a 2-methanesulfonamidoethyl group.

Preferable specific examples of the azomethine dye represented by formula (IIB) according to the present invention are shown below. However, the present invention should not be construed as being limited to these compounds.
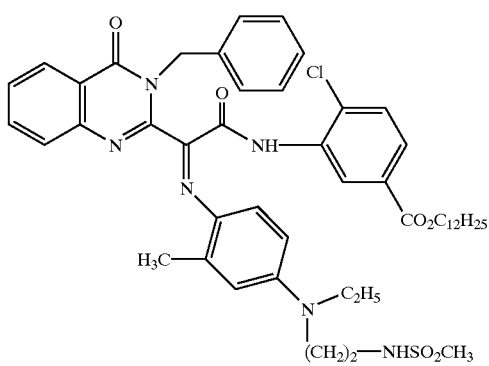
(D-1B)
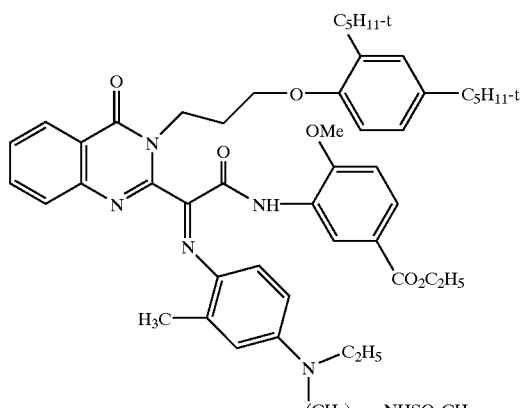
(D-2B)
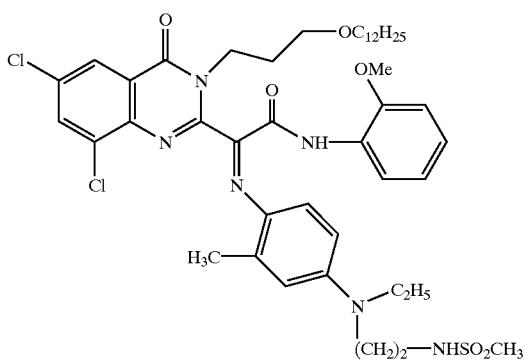
(D-3B)
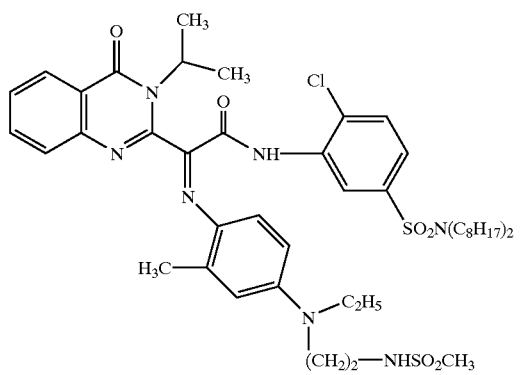
(D-4B)
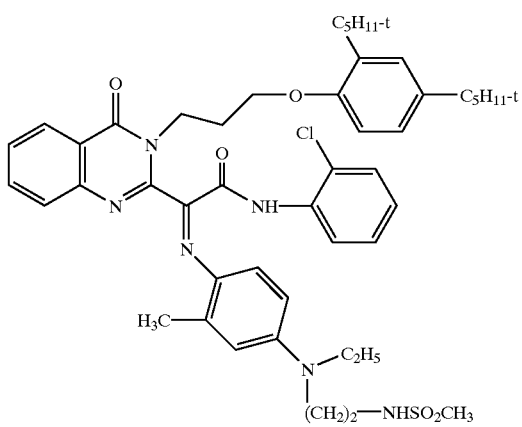
(D-5B)
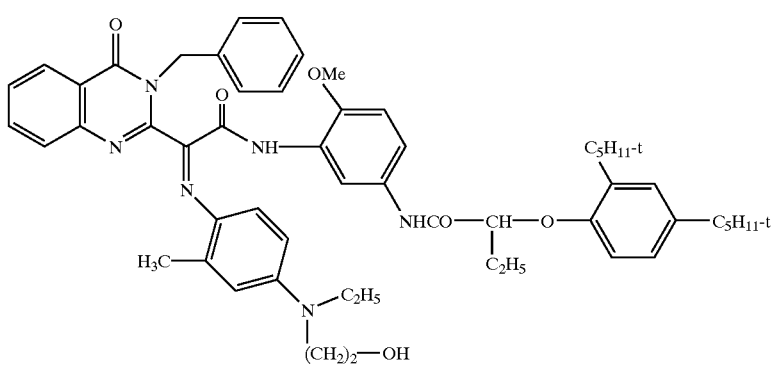
(D-6B)

-continued
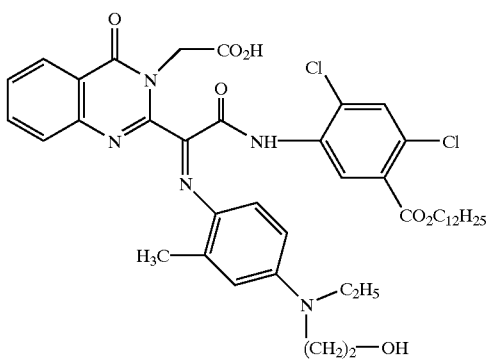
(D-7B)
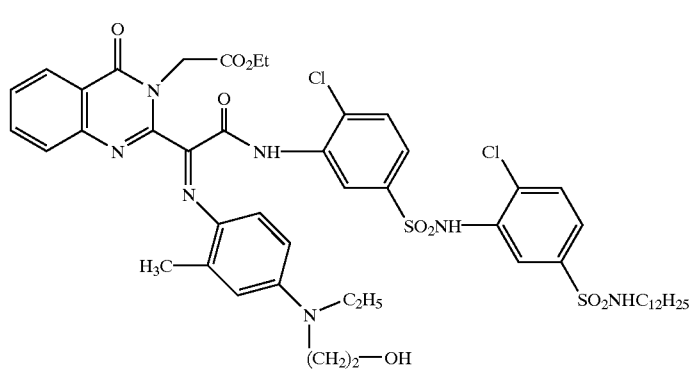
(D-8B)
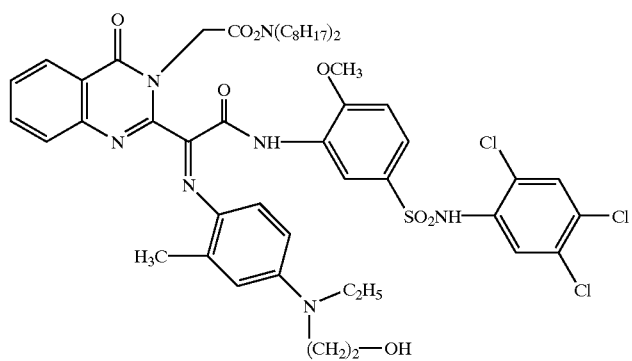
(D-9B)
(D-10B)
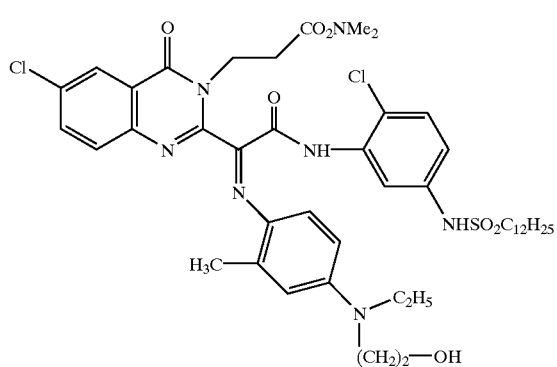
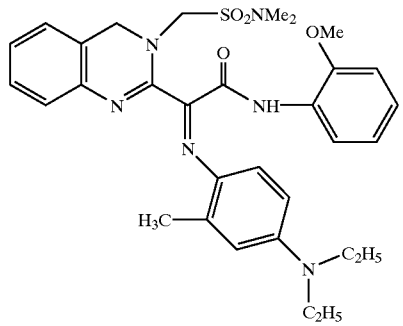
(D-11.B)

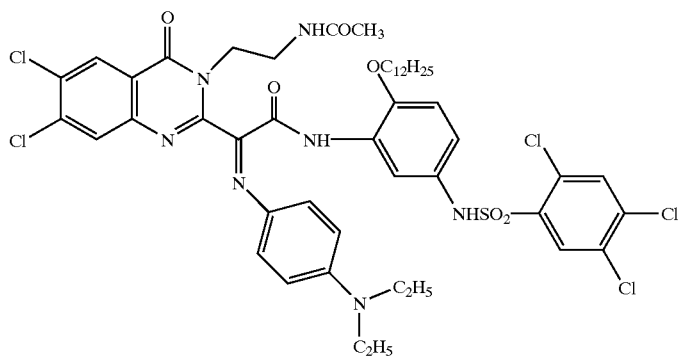
(D-12B)
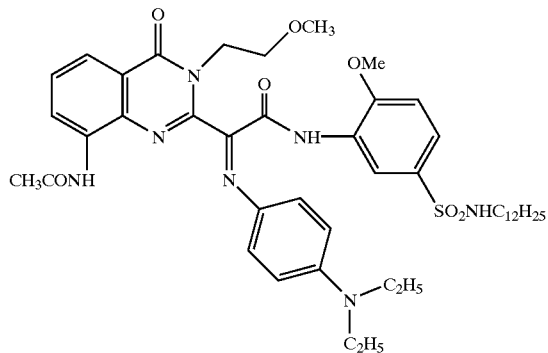
(D-13B)
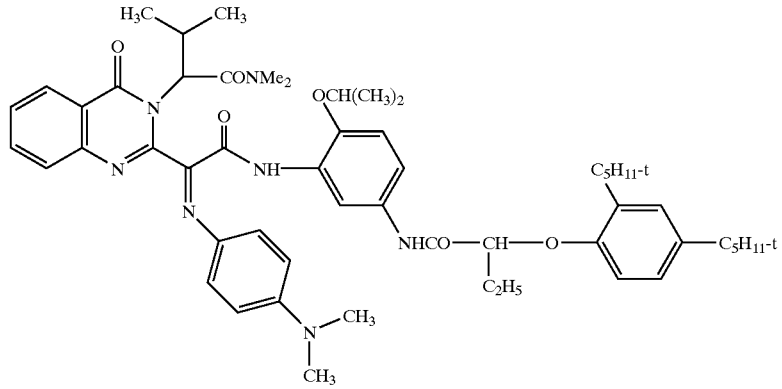
(D-14B)
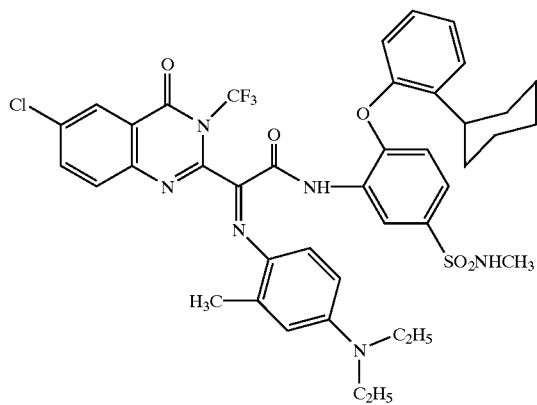
(D-15B)
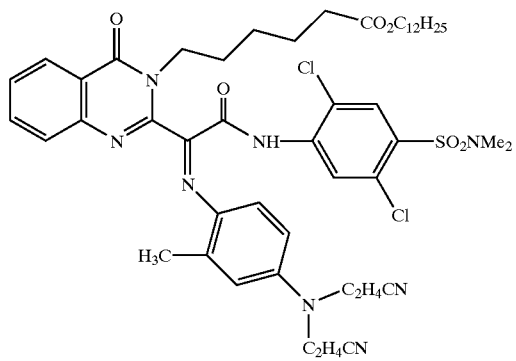
(D-16B)

-continued
(D-17B)
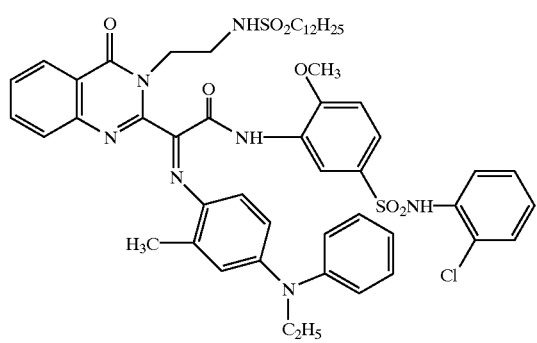
(D-18B)
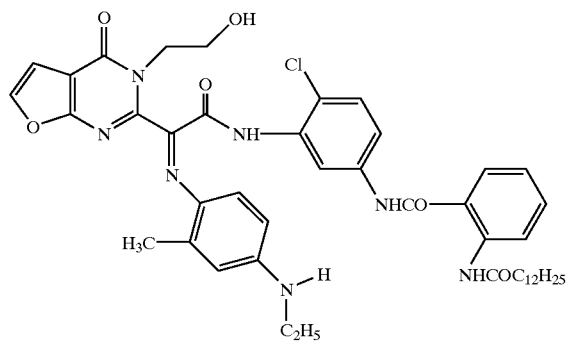
(D-19)
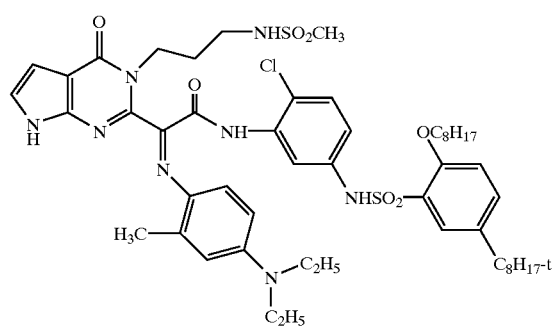
(D-20)
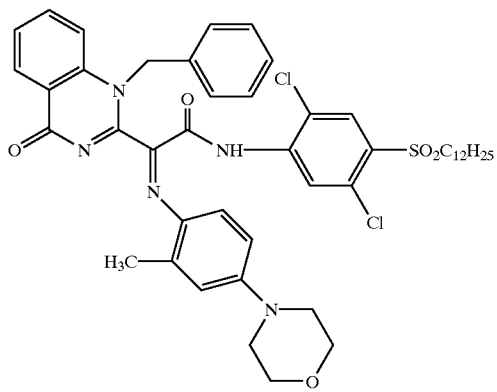
(D-21)
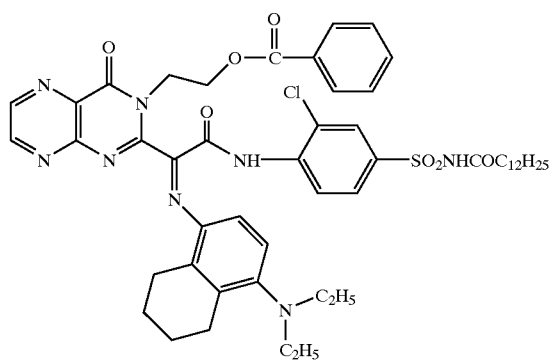
(D-22)
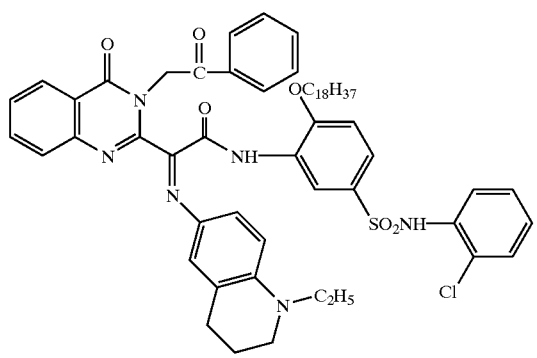
(D-23)
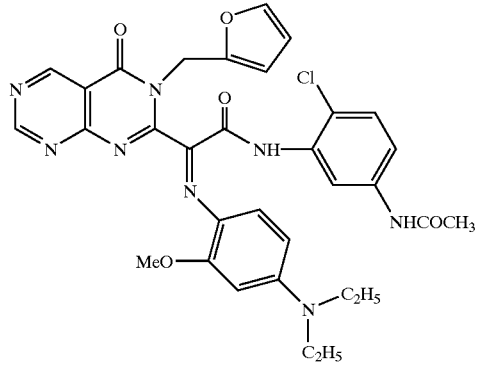
(D-24)
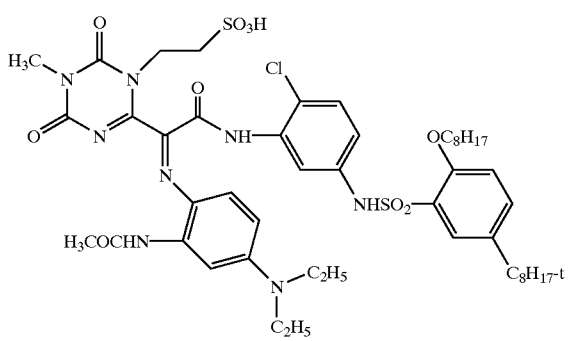

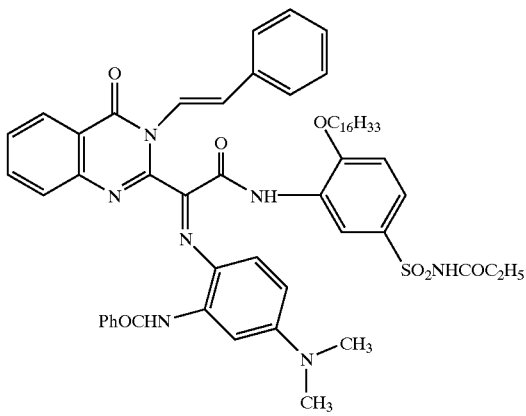

(D-25B)

The compounds represented by formula (IIB) according to the present invention can be synthesized by a coupling reaction of the compound represented by formula (IB) according to the present invention, with an oxidized product of a phenylenediamine-series developing agent (particularly an N,N-di-substituted-p-phenylenediamine derivative). Besides, the compound of formula (IIB) can be synthesized by reaction of the compound represented by formula (IB) according to the present invention in which Y is a hydrogen atom, with a 4-nitrosoaniline-series compound. Specific synthesis of the compounds is explained in the Examples described below.

The azomethine dye compounds of the present invention, which are excellent in both hue and fastness, can be used in many fields. Particularly the azomethine dye compounds are useful for the ink, dyestuffs, and the like. Further, the azomethine dye compounds are useful as an image-forming dye, for example, dyestuffs for the ink which is used for an ink-jet printer. Besides, the azomethine dye compounds are useful as dyestuffs for color photography.

According to the present invention, can be provided a dye-forming coupler that gives a dye having an excellent hue and an excellent storage stability. Further, in addition to the above, according to the present invention, can also be provided a dye-forming coupler that gives a dye having an excellent hue, especially an excellent sharpness at the foot portion of a peak in interest of the absorption curve at the longer wavelength side, and that can be produced at a low production cost owing to reduced steps. Furthermore, in addition to the above, according to the present invention, can also be provided a dye-forming coupler that gives a dye having a large molecular extinction coefficient, an excellent storage stability, especially an excellent light-fastness, and that can be produced at a low production cost owing to reduced steps.

Further, according to the present invention, can be provided a silver halide photographic light-sensitive material that exhibits both excellent color reproducibility and dye-image fastness, by adding the coupler in the light-sensitive material. Furthermore, in addition to the above, according to the present invention, can be also provided a silver halide photographic light-sensitive material that exhibits good sharpness.

Still further, according to the present invention, can be provided an azomethine dye compound having both excellent hue and storage stability. Further, in addition to the above, according to the present invention, can be also provided an azomethine dye compound having a large molecular extinction coefficient.

The present invention will now be described in more detail with reference to the following examples, but the invention is not limited to those.

EXAMPLES

Comparative Examples 1 to 2

1. Preparation of a Dye for Comparison (CD-1)

To a mixture of 0.85 g of the following coupler for comparison (C-1), 0.80 g of N-ethyl-N-(β-methanesulfoneamidoethyl)-3-methyl-4-aminoaniline sulfate, 3.75 g of sodium carbonate, 60 ml of THF and 50 ml of water, was gradually added a solution of 1.45 g of ammonium persulfate dissolved in 10 ml of water, at room temperature under stirring. The reaction liquid was stirred for 1 hour and then the THF phase was separated. The THF phase was purified by silica gel chromatography, to give a dye for comparison (CD-1), which was the following yellow azomethine dye for comparison.

Coupler for Comparison (C-1)

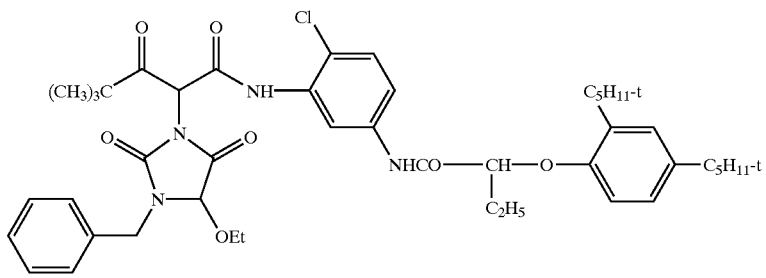

Dye for Comparison (CD-1)

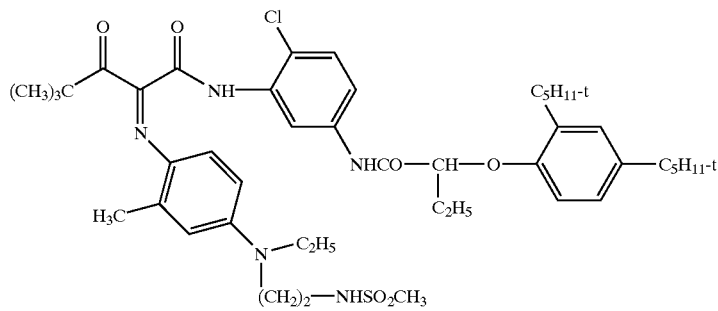

2. Preparation of A dye for Comparison (CD-2)

To a mixture of 0.73 g of the following coupler for comparison (C-2) (Compound (2) described in U.S. Pat. No. 5,455,149), 0.80 g of N-ethyl-N-(β-methanesulfonamidoethyl)-3-methyl-4-aminoaniline sulfate, 3.75 g of sodium carbonate, 60 ml of THF and 50 ml of water, a solution of 1.45 g of ammonium persulfate dissolved in 10 ml of water was gradually added with stirring at room temperature. After stirring the reaction mixture at 60° C. for 10 minutes, the THF layer was separated and purified by silica gel column chromatography, to obtain a dye for comparison (CD-2) which was a yellow azomethine dye for comparison as shown below.

Coupler for Comparison (C-2) (Compound (2) Described in U.S. Pat. No. 5,455,149)

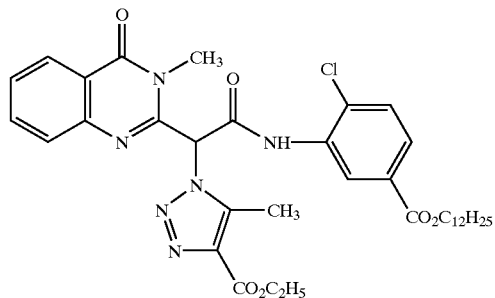

Dye for Comparison (CD-2)

Examples 1 to 4
1. Preparation of Dyes (D-1) to (D-4)

The following dyes: D-1 (wherein the coupler (1) was used), D-2 (wherein the coupler (2) was used), D-3 (wherein the coupler (20) was used), and D-4 (wherein the coupler (30) was used), which were azomethine dye compounds obtained from the dye-forming couplers of the present invention, were synthesized in the same manner as the "Preparation of a dye for comparison (CD-2)" in Comparative Example 2, except for replacing the coupler for comparison (C-2) with the above-shown exemplified coupler (1), coupler (2), coupler (20) and coupler (30) of the present invention, respectively.

(D-1)

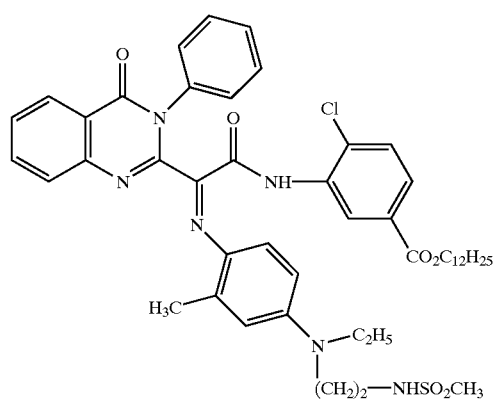

-continued

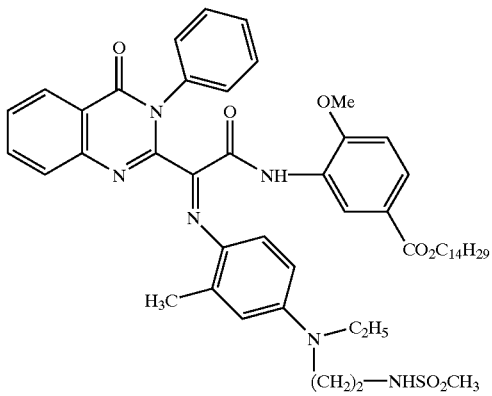
(D-2)

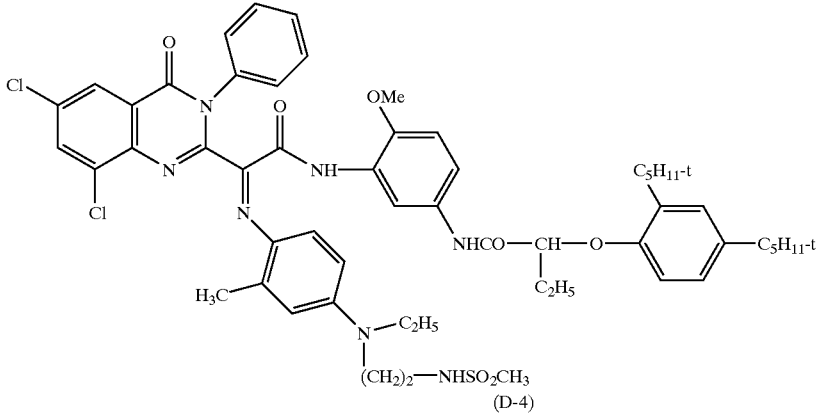
(D-3)

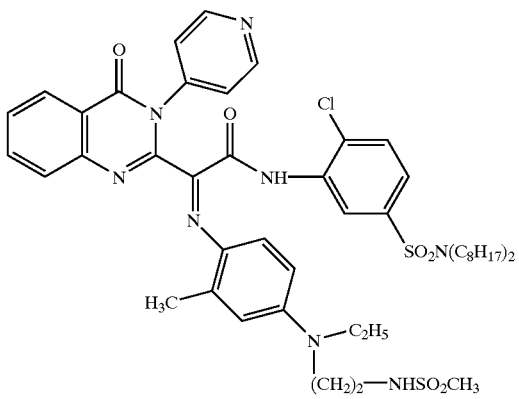
(D-4)

Measurement of Absorption Spectrum

Using each of the dyes for comparison (CD-1) and (CD-2) and the dyes (D-1) to (D-4) of the present invention, each of which was obtained in Comparative Examples 1 and 2 and Examples 1 to 4 described above, absorption spectra were measured in the following manner.

1.5 mg of any one of the dyes for comparison (CD-1) and (CD-2) and the dyes (D-1) to (D-4) was precisely weighed in a 100-ml measuring flask. 100 ml of ethyl acetate was added to dissolve the dye. Each resulting solution was diluted with ethyl acetate, to prepare a sample solution 101 containing the dye for comparison (CD-1), a sample solution 102 containing the dye for comparison (CD-2), a sample solution 103 containing the dye (D-1), a sample solution 104 containing the dye (D-2), a sample solution 105 containing the dye (D-3), and a sample solution 106 containing the dye (D-4), respectively.

Each of the thus-obtained sample solutions 101 to 106 was placed in 1-cm thick-quartz cell, and visible absorption spectrum was measured by an ultraviolet-visible spectrophotometer, manufactured by Shimadzu Corporation. Further, as the parameter that expresses the sharpness at the foot portion of a peak in interest of the absorption curve at the longer wavelength side of the dye to be used, $\Delta S(0.05)$/nm of each dye was obtained, according to the following manner. Assuming that absorbance (A) of the maximum absorption wavelength ($\lambda$max) is 1, the wavelength ($\lambda(0.05)$) corresponding to A=0.05 at the longer wavelength side was measured. The $\Delta S(0.05)$/nm is obtained by calculation according to the following expression:

$$\Delta S(0.05) = \lambda max - \lambda(0.05)$$

The results that were obtained by the above calculation, are shown in Table 2.

TABLE 2

| Sample No. | Kind of Coupler | Kind of Dye | ΔS (0.05)/nm | Remarks |
|---|---|---|---|---|
| 101 | Coupler for comparison (C-1) | CD-1 | 78.0 | Comparative Example |
| 102 | Coupler for comparison (C-2) | CD-2 | 74.2 | Comparative Example |
| 103 | Coupler (1) | D-1 | 72.9 | This invention |
| 104 | Coupler (2) | D-2 | 70.6 | This invention |
| 105 | Coupler (20) | D-3 | 70.3 | This invention |
| 106 | Coupler (30) | D-4 | 71.2 | This invention |

From the results shown in Table 2, it is understood that the dyes obtained from the dye-forming couplers of the present invention exhibit smaller ΔS (0.05)/nm than those obtained from dye-forming couplers for comparison, which means that the dyes of the present invention are excellent in sharpness at the foot portion of a peak of the absorption curve at the longer wavelength side. In other words, in a silver halide photographic light-sensitive material containing the coupler of the present invention, only a small portion of a reddish tinge is mixed in a yellow dye obtained from the coupler, resulting in improvement in color reproducibility of the obtained image (particularly color reproducibility of lemon yellow).

Test of Fading Resistance of Dyes to an Acid

With respect to each of the dyes for comparison (CD-1) and (CD-2) and the dyes (D-1) to (D-4), which were obtained in Comparative Examples 1 and 2 and Examples 1 to 4 described above, a test of fading resistance to an acid was carried out in the following manner.

1.0 mg of any one of the dyes for comparison (CD-1) and (CD-2) and the dyes (D-1) to (D-4) was dissolved in 15 ml of NMP (1-methyl-2-pyrrolidinone; purity for peptide synthesis: 99%), to prepare a sample solution 201 containing the dye for comparison (CD-1), a sample solution 202 containing the dye for comparison (CD-2), a sample solution 203 containing the dye (D-1), a sample solution 204 containing the dye (D-2), a sample solution 205 containing the dye (D-3), and a sample solution 206 containing the dye (D-4), respectively.

0.49 g of boric acid, 8 ml of 1-normal acetic acid aqueous solution and 16 ml of 1-normal phosphoric acid aqueous solution were mixed in a 200-ml measuring flask, to prepare a solution (Britton-Robinson buffer solution; hereinafter referred to as "B. R. buffer A solution" for short). Then, phosphoric acid was added to the resulting solution and pH was adjusted to 1.15, and then the temperature of the solution was maintained at 60° C. The resulting buffer solution was added to the previously prepared sample solutions 201 to 206 until the total amount would become 25 ml. Then, visible absorption spectra of the thus-obtained solutions directly after the preparation by adding the buffer solution to the sample solutions, and after 4 hour storage at a constant temperature of 60° C., were measured, by means of ultraviolet-visible spectrometer, manufactured by Shimadzu Corporation. Absorbance of each of the solutions at the maximum absorption wavelength was calculated respectively.

The rate of density (the remaining ratio: %) was calculated in the ratio of absorbance of a sample before the test of fading resistance to an acid and absorbance of the same sample after the test of fading resistance to an acid. The resultant remaining ratio was utilized as an evaluation indicator of fastness of the dye to an acid. The results that were obtained are shown in Table 3.

TABLE 3

| Sample No. | Kind of Coupler | Kind of Dye | Remaining ratio (%) | Remarks |
|---|---|---|---|---|
| 201 | Coupler for comparison (C-1) | CD-1 | 15 | Comparative Example |
| 202 | Coupler for comparison (C-2) | CD-2 | 94 | Comparative Example |
| 203 | Coupler (1) | D-1 | 98 | This invention |
| 204 | Coupler (2) | D-2 | 98 | This invention |
| 205 | Coupler (20) | D-3 | 99 | This invention |
| 206 | Coupler (30) | D-4 | 98 | This invention |

It is apparent from the Table 3 that the dye obtained from the dye-forming coupler of the present invention is remarkably excellent in fastness of the dye to an acid.

Comparative Example 3

1. Preparation of Emulsified Dispersion of Coupler for comparison (C-1)

0.88 g of coupler for comparison (C-1) and 2.6 g of tricresyl phosphate were dissolved with heating in 10 ml of ethyl acetate. The resulting solution is referred to as an oil phase solution. Separately, 4.2 g of gelatin was added to 25 ml of water at room temperature and swelled sufficiently. Thereafter, the gelatin mixture was heated to 40° C. and completely dissolved. To the resulting aqueous gelatin solution kept at about 40° C., 3 ml of 5% aqueous sodium dodecylbenzenesulfonate solution and the previously prepared oil phase solution were added. Then, the resulting mixture was emulsified dispersed by a homogenizer, to prepare the emulsified dispersion of coupler for comparison (C-1).

2. Preparation of Light-sensitive Material for Comparison

A coating solution having the composition described below, including the previously prepared emulsified dispersion of coupler for comparison (C-1), was prepared. On a polyethylene laminate paper having an undercoat layer, the thus-obtained coating solution was coated so that the coating amounts of the silver halide emulsion and the coupler became 0.33 mmol/m$^2$ (in terms of silver) and 1 mmol/m$^2$, respectively. Furthermore, a gelatin was coated as a protective layer so that the coating amount of gelatin became 2 g/m$^2$. Thus, Sample 301 of a light-sensitive material for comparison, was prepared.

(Composition of Coating Solution)

| | |
|---|---|
| Emulsion: Silver Chlorobromide (cubic grains in which 0.3 mole % in total of silver bromide was locally contained in a portion of the grain surface and the substrate was silver chloride with average grain size of 60 μm. To spectrally sensitize this emulsion, each of sensitizing dyes A, B and C was added in 1.4 × 10$^{-4}$ mole per mole of silver halide, respectively) | 13 g |
| 10% Gelatin | 28 g |
| Emulsified Dispersion of the above-described Coupler for comparison (C-1) | 22 g |

-continued

| | |
|---|---|
| Water | 37 ml |
| 4% Aqueous Solution of Sodium 1-Hydroxy-3,5-dichloro-s-triazine | 5 ml |

(Sensitizing Dye A)

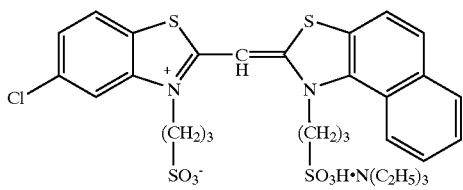

(Sensitizing Dye B)

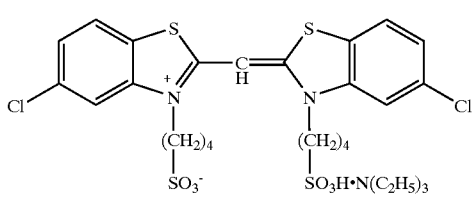

(Sensitizing Dye C)

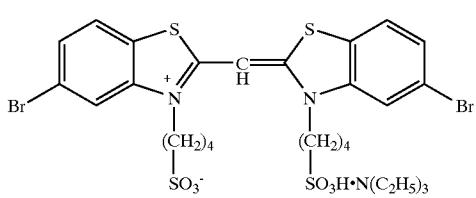

Comparative Example 4

1. Preparation of Emulsified Dispersion of Coupler for Comparison (C-2)

Emulsified dispersion of Coupler for comparison (C-2) was prepared in the same manner as the "1. Preparation of Emulsified Dispersion of Coupler for comparison (C-1)" in Comparative Example 3, except for replacing the Coupler for comparison (C-1) with the Coupler for comparison (C-2) (Compound (2) described in U.S. Pat. No. 5,455,149).

2. Preparation of Light-sensitive Material for Comparison

Light-sensitive material for comparison sample 302 was prepared in the same manner as the "2. Preparation of Light-sensitive material for comparison" in Comparative Example 3, except for replacing the emulsified dispersion of Coupler for comparison (C-1) with the emulsified dispersion of Coupler for comparison (C-2) (Compound (2) described in U.S. Pat. No. 5,455,149).

Examples 5 to 8

1. Preparation of each of Emulsified Dispersions of Couplers (1), (2), (20) and (30)

Each of emulsified dispersions of couplers according to the present invention was prepared in the same manner as the "1. Preparation of Emulsified Dispersion of Coupler for comparison (C-1)" in Comparative Example 3, except for replacing the coupler for comparison (C-1) with the foregoing exemplified couplers (1), (2), (20) and (30) of the present invention, respectively.

2. Preparation of Light-sensitive Material of the Present Invention

In the same manner as in "2. Preparation of Light-sensitive material for comparison" in Comparative Example 3, Sample 303 (use was made of the coupler (1)), Sample 304 (use was made of the coupler (2)), Sample 305 (use was made of the coupler (20)), Sample 306 (use was made of the coupler (30)), each of which was the light-sensitive material of the present invention, were prepared, except for replacing the emulsified dispersion of Coupler for comparison (C-1) with the emulsified dispersions of the foregoing exemplified couplers (1), (2), (20) and (30) of the present invention, respectively.

Evaluation Tests of Color-image Fastness

Using the samples 301 to 306 which were obtained in the foregoing Comparative Examples 3 to 4 and Examples 5 to 8, the evaluation tests of color-image fastness was carried out in the following way.

First, each of the samples was wedge-wise exposed to a white light, and then subjected to color-development processing according to the processing steps as shown below.

(Processing Steps)

| Step | Temperature | Time |
|---|---|---|
| Color-developing | 38.5° C. | 45 seconds |
| Bleach-fixing | 30 to 36° C. | 45 seconds |
| Stabilization (1) | 30 to 37° C. | 20 seconds |
| Stabilization (2) | 30 to 37° C. | 20 seconds |
| Stabilization (3) | 30 to 37° C. | 20 seconds |
| Drying | 70 to 85° C. | 70 seconds |

The respective steps of the color developing, the bleach-fixing, and the stabilization (1), (2) and (3) were carried out by immersing each of the samples into the following respective processing solutions under the above-mentioned conditions.

| (Color-developing solution in the color-developing step) | |
|---|---|
| Water | 800 ml |
| Dimethylpolysiloxane-series surfactant (Silicone KF351A (trade name), manufactured by Shin-Etsu Chemical Co., Ltd.) | 0.1 g |
| Triethanolamine | 11.6 g |
| Ethylenediaminetetraacetic acid | 4.0 g |
| Sodium 4,5-dihydroxybenzene-1,3-disulfonate | 0.5 g |
| Potassium chloride | 10.0 g |
| Potassium bromide | 0.040 g |
| Triazinylaminostylbene-series fluorescent whitening agent (Hakkol FWA-SF (trade name), manufactured by Showa Chemicals Inc.) | 2.5 g |
| Sodium sulfite | 0.1 g |
| Disodium N,N-bis(sulfonatoethyl) hydroxylamine | 8.5 g |
| N-ethyl-N-(β-methanesulfonamidoethyl)-3-methyl-4-aminoaniline · 3/2 · sulfate · monohydrate | 5.0 g |
| Potassium carbonate | 26.3 g |
| Water to make | 1000 ml |
| pH (adjusted with potassium hydroxide and sulfuric acid at 25° C.) | 10.15 |

-continued

| (Bleach-fixing solution in the bleach-fixing step) | |
|---|---|
| Water | 800 ml |
| Iron (III) ammonium ethylenediaminetetraacetate | 47.0 g |
| Ethylenediaminetetraacetic acid | 1.4 g |
| m-Carboxymethylbenzenesulfinic acid | 8.3 g |
| Nitric acid (67%) | 16.5 g |
| Imidazole | 14.6 g |
| Ammonium thiosulfate aq. solution (750 g/liter) | 107 ml |
| Ammonium sulfite | 16.0 g |
| Potassium metabisulfite | 23.1 g |
| Water to make | 1000 ml |
| pH (adjusted with acetic acid and ammonia at 25° C.) | 6.0 |
| (Stabilizing solution in the stabilization (1) to (3) steps) | |
| Sodium chlorinated-isocyanurate | 0.02 g |
| Deionized water (electroconductivity: 5 μS/cm or less) | 1000 ml |
| pH | 6.5 |

The processed samples each colored yellow. Each of the light-sensitive material, samples 303 to 306 according to the present invention gave the dye image having a sharper hue than those of light-sensitive material for comparison, samples 301 to 302.

Then, each of the color developing-processed samples 301 to 306 was irradiated with Xenon light source (100,000 lux) with intermittent illumination under the conditions of light for 5 hours/darkness for 1 hour, for 14 days, and light-fastness of the dye image was evaluated. The density after irradiation at a portion where the initial density D=1.0 is indicated as the remaining ratio in percent. The results that were obtained are shown in Table 4.

As is apparent from Table 4, it is understood that the light-sensitive materials of the present invention are excellent in light-fastness.

TABLE 4

| Sample No. | Kind of Coupler | Kind of Dye | Remaining ratio (%) | Remarks |
|---|---|---|---|---|
| 301 | Coupler for comparison (C-1) | CD-1 | 85 | Comparative Example |
| 302 | Coupler for comparison (C-2) | CD-2 | 74 | Comparative Example |
| 303 | Coupler (1) | D-1 | 92 | This invention |
| 304 | Coupler (2) | D-2 | 90 | This invention |
| 305 | Coupler (20) | D-3 | 93 | This invention |
| 306 | Coupler (30) | D-4 | 91 | This invention |

Example 9

After corona discharge treatment was performed on the surface of a paper support whose both surfaces were laminated with polyethylene resin, a gelatin undercoat layer containing sodium dodecylbenzenesulfonate was formed on that surface. In addition, photographic constituting layers from the first layer to the seventh layer were successively coated on the support, to make a silver halide color photographic light-sensitive material (sample 001) having the following layer arrangement. The coating solution for each of the photographic constituting layers was prepared as follows.

Preparation of Coating-solution for First Layer 62 g of a yellow coupler (ExY), 8 g of a dye-image stabilizer (Cpd-1), 4 g of a dye-image stabilizer (Cpd-2), 8 g of a dye-image stabilizer (Cpd-3) and 2 g of a dye-image stabilizer (Cpd-8) were dissolved in 23 g of a solvent (Solv-1) and 80 ml of ethyl acetate. The resultant solution was added to 220 g of 23.5% by mass gelatin aqueous solution containing 4 g of sodium dodecylbenzenesulfonate. The resultant mixture was emulsified and dispersed by a high speed stirring emulsifier (DISOLVER), followed by addition of water, to prepare 900 g of emulsified dispersion A.

Separately, a silver chlorobromide emulsion A (cubic, a 3:7 mixture (Ag molar ratio) of a large-size emulsion A with an average grain size of 0.72 μm and a small-size emulsion A with an average grain size of 0.60 μm. The variation coefficients of grain size distributions of the large-size and the small-size emulsions were 0.08 and 0.10, respectively. Each emulsion consisted of silver halide grains in which 0.3 mole % of AgBr was locally contained in a portion of the grain surface and the substrate was silver chloride) was prepared.

To this emulsion, were added blue-sensitive sensitizing dyes A, B and C shown below in $1.4 \times 10^{-4}$ mole for the large-size emulsion and $1.7 \times 10^{-4}$ mole for the small-size emulsion per mole of silver halide, respectively. Chemical ripening of this emulsion was carried out optimally, by adding a sulfur sensitizer and a gold sensitizer.

The emulsified dispersion A described above and this silver chlorobromide emulsion A were mixed and dispersed, to prepare a coating solution of the first layer having the following composition. The coating amount of each silver halide emulsion is in terms of silver.

Preparation of Coating-solutions for Second Layer to Seventh Layer

The coating solutions for the second to seventh layers were prepared in the similar manner as for the coating solution of the first layer. 1-oxy-3,5-dichloro-s-triazine sodium salt was used as a gelatin hardener in each layer. In addition, Ab-1, Ab-2, Ab-3 and Ab-4 were added to each layer such that their total amounts were 15.0 mg/m², 60.0 mg/m², 5.0 mg/m² and 10.0 mg/m², respectively.

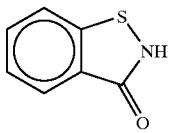
(Ab-1) Antiseptic

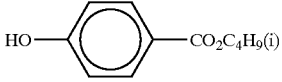
(Ab-2) Antiseptic

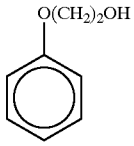
(Ab-3) Antiseptic (Ab-4) Antiseptic

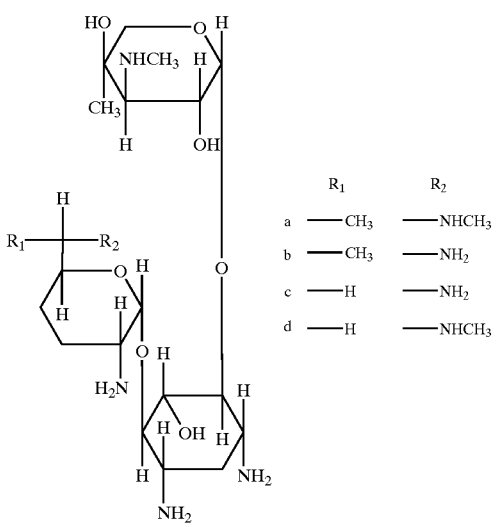

A mixture in 1:1:1:1 (molar ratio) of a, b, c, and d

For the silver chlorobromide emulsion of the respective light-sensitive emulsion layer, the following spectral sensitizing dyes were used.

Blue-sensitive Emulsion Layer (Sensitizing Dye A)

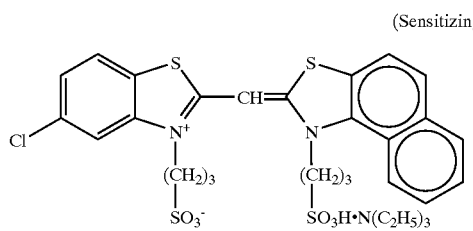

(Sensitizing dye A)

(Sensitizing dye B)

(Sensitizing dye C)

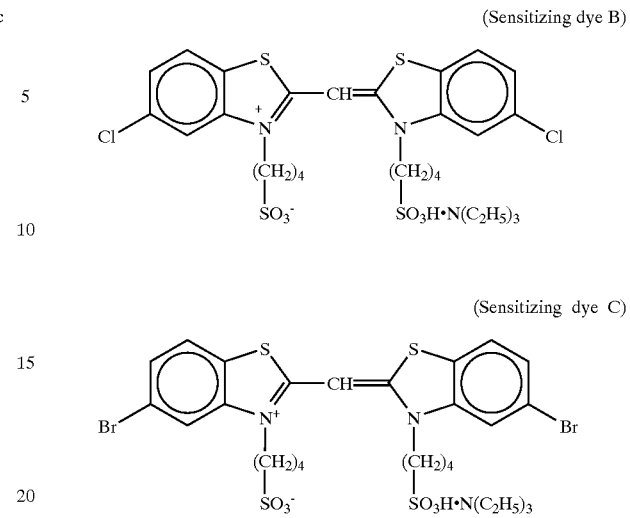

(The sensitizing dyes A, B, and C were added to the large-size emulsion in an amount of $1.4 \times 10^{-4}$ mol, respectively per mol of silver halide, and to the small-size emulsion in an amount of $1.7 \times 10^{-4}$ mol, respectively per mol of silver halide.)

Green-Sensitive Emulsion Layer (Sensitizing dye D)

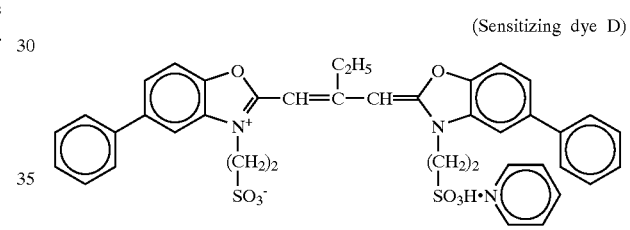

(Sensitizing dye E)

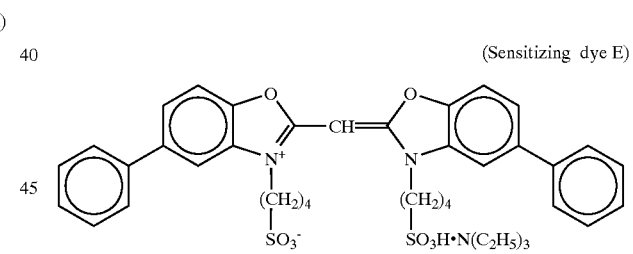

(Sensitizing dye F)

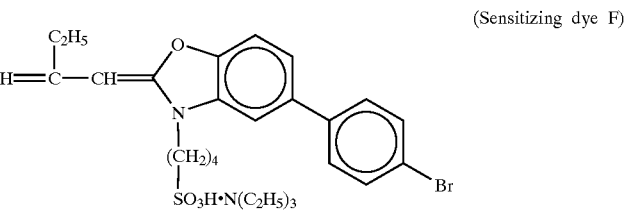

(The sensitizing dye D was added to the large-size emulsion in an amount of $3.0 \times 10^{-4}$ mol, and to the small-size emulsion in an amount of $3.6 \times 10^{-4}$ mol, per mol of the silver halide; the sensitizing dye E was added to the large-size emulsion in an amount of $4.0 \times 10^{-5}$ mol, and to the small-size emulsion in an amount of $7.0 \times 10^{-5}$ mol, per mol of the silver halide; and the sensitizing dye F was added to the large-size emulsion in an amount of $2.0 \times 10^{-4}$ mol, and to the small-size emulsion in an amount of $2.8 \times 10^{-4}$ mol, per mol of the silver halide.)

Red-Sensitive Emulsion Layer (Sensitizing dye G)

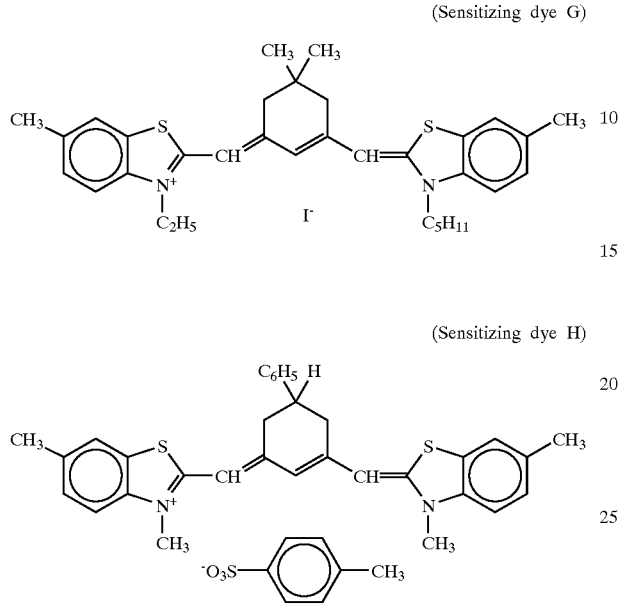

(Sensitizing dye H)

(The sensitizing dyes G, and H were added to the large-size emulsion in an amount of $6.0 \times 10^{-5}$ mol, respectively per mol of silver halide, and to the small-size emulsion in an amount of $9.0 \times 10^{-5}$ mol, respectively per mol of silver halide.)

Further, the following compound I was added to the red-sensitive emulsion layer in an amount of $2.6 \times 10^{-3}$ mol per mol of the silver halide.

(Compound I)

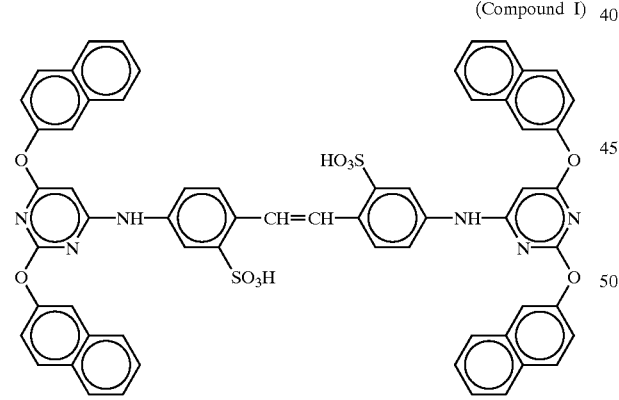

Further, to the blue-sensitive emulsion layer, the green-sensitive emulsion layer, and the red-sensitive emulsion layer, was added 1-(3-methylureidophenyl)-5-mercaptotetrazole in amounts of $3.3 \times 10^{-4}$ mol, $1.0 \times 10^{-3}$ mol, and $5.9 \times 10^{-4}$ mol, respectively, per mol of the silver halide. Further, the compound was also added to the second layer, the forth layer, the sixth layer, and the seventh layer, in amounts of 0.2 mg/m², 0.2 mg/m², 0.6 mg/m², and 0.1 mg/m², respectively.

Further, to the blue-sensitive emulsion layer and the green-sensitive emulsion layer, was added 4-hydroxy-6-methyl-1,3,3a, 7-tetrazaindene in amounts of $1 \times 10^{-4}$ mol and $2 \times 10^{-4}$ mol, respectively, per mol of the silver halide.

Further, to the red-sensitive emulsion layer, was added a copolymer of methacrylic acid and butyl acrylate (1:1 in mass ratio; average molecular weight, 200,000 to 400,000) in an amount of 0.05 g/m².

Further, to the second layer, the fourth layer, and the sixth layer, was added a mixture of disodium catechol-3,5-disulfonate and 2,6-bishydroxyamino-4-dimetylamino-1,3, 5-triazine (9:1 in molar ratio) in amounts of 6 mg/m², 6 mg/m², and 18 mg/m², respectively.

Further, in order to prevent irradiation, the following dyes (coating amounts are shown in parentheses) were added to the emulsion layers.

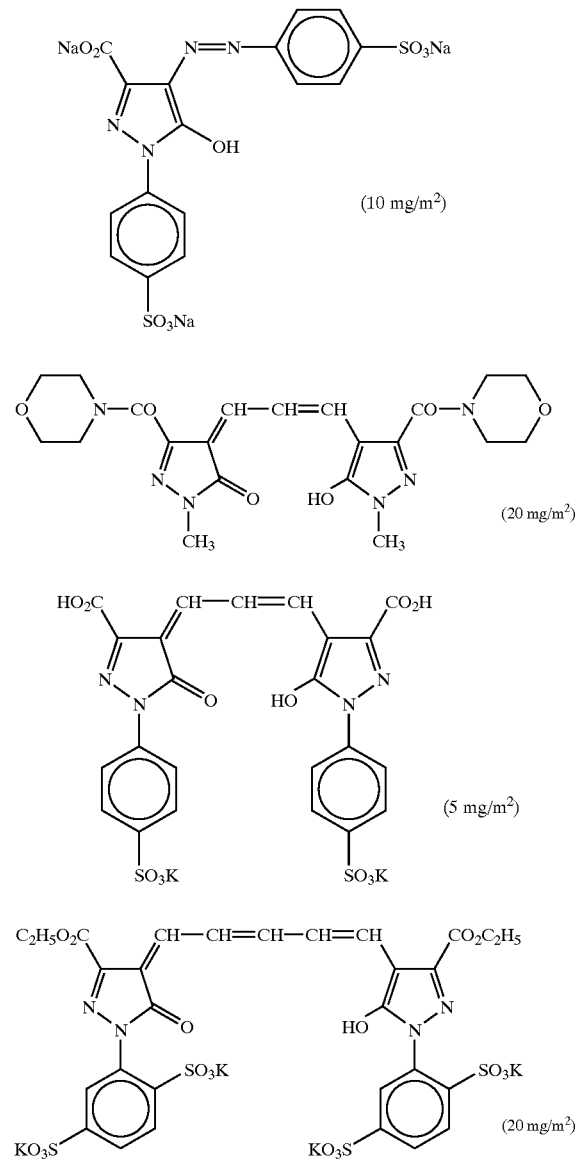

-continued

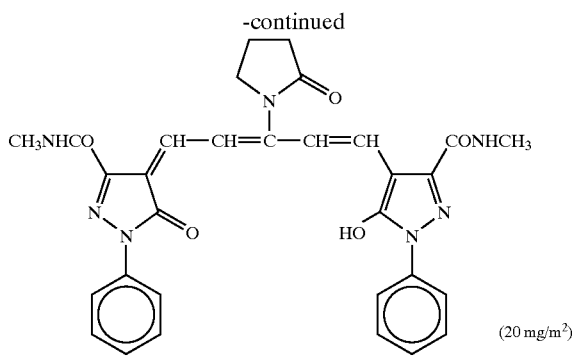

(20 mg/m²)

Layer Constitution

The composition of each layer is shown below. The numbers show coating amounts (g/m²). In the case of the silver halide emulsion, the coating amount is in terms of silver.

Support

Polyethylene-resin laminated paper
{The polyethylene resin on the first layer side contained a white pigment (TiO$_2$; content of 16 mass %, ZnO; content of 4 mass %), a fluorescent whitening agent (a mixture of 4,4'-bis(benzoxazolyl)stilbene and 4,4'-bis(5-methylbenzoxazolyl)stilbene mixed in a ratio of 8/2; content of 0.05 mass %) and a bluish dye (ultramarine)}

| First Layer (Blue-Sensitive Emulsion Layer) | |
|---|---|
| A silver chlorobromide emulsion A (cubic, a 3:7 mixture of a large-size emulsion A having an average grain size of 0.72 μm, and a small-size emulsion A having an average grain size of 0.60 μm (in terms of mol of silver). The deviation coefficients of the grain size distribution were 0.08 and 0.10, respectively. Each emulsion had 0.3 mol % of silver bromide contained locally in part of the grain surface whose substrate was made up of silver chloride) | 0.26 |
| Gelatin | 1.35 |
| Yellow coupler (ExY) | 0.62 |
| Color-image stabilizer (Cpd-1) | 0.08 |
| Color-image stabilizer (Cpd-2) | 0.04 |
| Color-image stabilizer (Cpd-3) | 0.08 |
| Color-image stabilizer (Cpd-8) | 0.02 |
| Solvent (Solv-1) | 0.23 |
| Second Layer (Color-Mixing Inhibiting Layer) | |
| Gelatin | 0.99 |
| Color-mixing inhibitor (Cpd-4) | 0.09 |
| Color-mixing inhibiting auxiliary (Cpd-5) | 0.018 |
| Stabilizer (Cpd-6) | 0.13 |
| Color-mixing inhibitor (Cpd-7) | 0.01 |
| Solvent (Solv-1) | 0.06 |
| Solvent (Solv-2) | 0.22 |
| Third Layer (Green-Sensitive Emulsion Layer) | |
| A silver chlorobromide emulsion B (cubic, a 1:3 mixture of a large-size emulsion B having an average grain size of 0.45 μm, and a small-size emulsion B having an average grain size of 0.35 μm (in terms of mol of silver). The deviation coefficients of the grain size distribution were 0.10 and 0.08, respectively. Each emulsion had 0.4 mol % of silver bromide contained locally in part of the grain surface whose substrate was made up of silver chloride) | 0.14 |
| Gelatin | 1.36 |
| Magenta coupler (ExM) | 0.15 |
| Ultraviolet absorbing agent (UV-1) | 0.05 |
| Ultraviolet absorbing agent (UV-2) | 0.03 |

-continued

| | |
|---|---|
| Ultraviolet absorbing agent (UV-3) | 0.02 |
| Ultraviolet absorbing agent (UV-4) | 0.03 |
| Ultraviolet absorbing agent (UV-6) | 0.01 |
| Color-image stabilizer (Cpd-2) | 0.02 |
| Color-mixing inhibitor (Cpd-4) | 0.002 |
| Stabilizer (Cpd-6) | 0.09 |
| Color-image stabilizer (Cpd-8) | 0.02 |
| Color-image stabilizer (Cpd-9) | 0.03 |
| Color-image stabilizer (Cpd-10) | 0.01 |
| Color-image stabilizer (Cpd-11) | 0.0001 |
| Solvent (Solv-3) | 0.11 |
| Solvent (Solv-4) | 0.22 |
| Solvent (Solv-5) | 0.20 |
| Fourth Layer (Color-Mixing Inhibiting Layer) | |
| Gelatin | 0.71 |
| Color-mixing inhibitor (Cpd-4) | 0.06 |
| Color-mixing inhibiting auxiliary (Cpd-5) | 0.013 |
| Stabilizer (Cpd-6) | 0.10 |
| Color-mixing inhibitor (Cpd-7) | 0.007 |
| Solvent (Solv-1) | 0.04 |
| Solvent (Solv-2) | 0.16 |
| Fifth Layer (Red-Sensitive Emulsion Layer) | |
| A silver chlorobromide emulsion C (cubic, a 1:4 mixture of a large-size emulsion C having an average grain size of 0.50 μm, and a small-size emulsion C having an average grain size of 0.41 μm (in terms of mol of silver). The deviation coefficients of the grain size distribution were 0.09 and 0.11, respectively. Each emulsion had 0.5 mol % of silver bromide contained locally in part of the grain surface whose substrate was made up of silver chloride) | 0.20 |
| Gelatin | 1.11 |
| Cyan coupler (ExC-2) | 0.13 |
| Cyan coupler (ExC-3) | 0.03 |
| Color-image stabilizer (Cpd-1) | 0.05 |
| Stabilizer (Cpd-6) | 0.05 |
| Color-mixing inhibitor (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.03 |
| Color-image stabilizer (Cpd-16) | 0.05 |
| Color-image stabilizer (Cpd-17) | 0.05 |
| Color-image stabilizer (Cpd-18) | 0.06 |
| Color-image stabilizer (Cpd-19) | 0.06 |
| Solvent (Solv-5) | 0.15 |
| Solvent (Solv-8) | 0.05 |
| Solvent (Solv-9) | 0.10 |
| Sixth Layer (Ultraviolet Absorbing Layer) | |
| Gelatin | 0.66 |
| Ultraviolet absorbing agent (UV-1) | 0.19 |
| Ultraviolet absorbing agent (UV-2) | 0.06 |
| Ultraviolet absorbing agent (UV-3) | 0.06 |
| Ultraviolet absorbing agent (UV-4) | 0.05 |
| Ultraviolet absorbing agent (UV-5) | 0.08 |
| Ultraviolet absorbing agent (UV-6) | 0.01 |
| Solvent (Solv-7) | 0.25 |
| Seventh Layer (Protective Layer) | |
| Gelatin | 1.00 |
| Acryl-modified copolymer of polyvinyl alcohol (modification degree: 17%) | 0.04 |
| Liquid paraffin | 0.02 |
| Surface-active agent (Cpd-13) | 0.01 |

(E x Y) Yellow coupler
A mixture in 60:40 (molar ratio) of
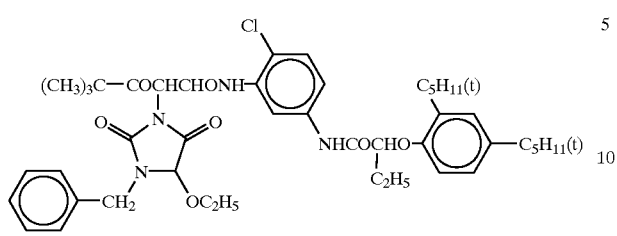
and
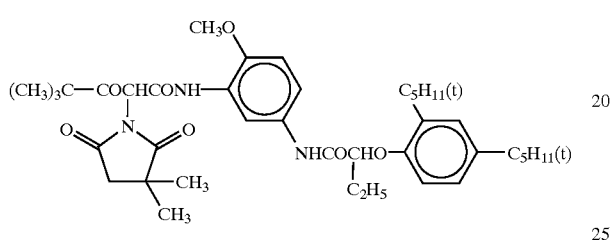
(E x M) Magenta coupler
A mixture in 60:40 (molar ratio) of
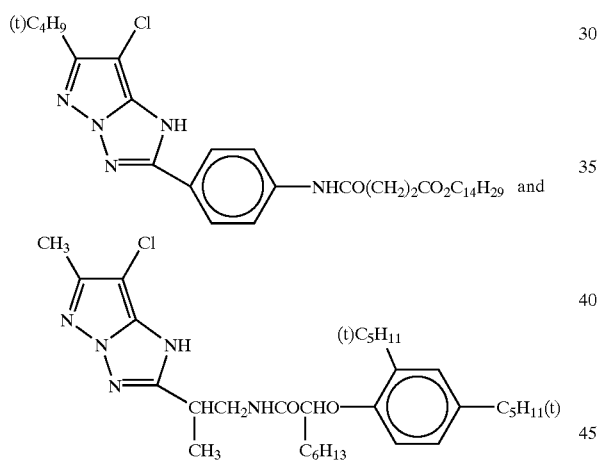
(E x C - 1) Cyan coupler
A mixture in 15:85 (molar ratio) of
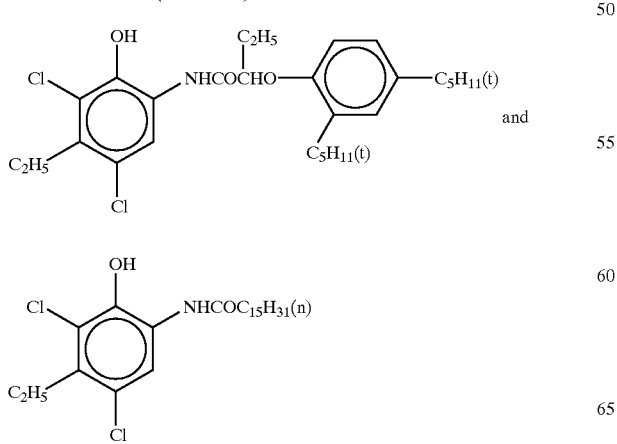
(E x C - 2) Cyan coupler
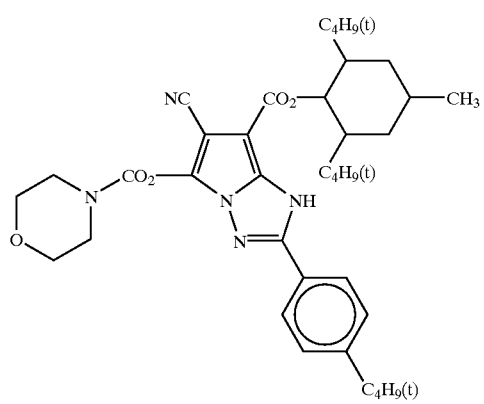
(E x C - 3) Cyan coupler
A mixture in 50:25:25 (molar ratio) of
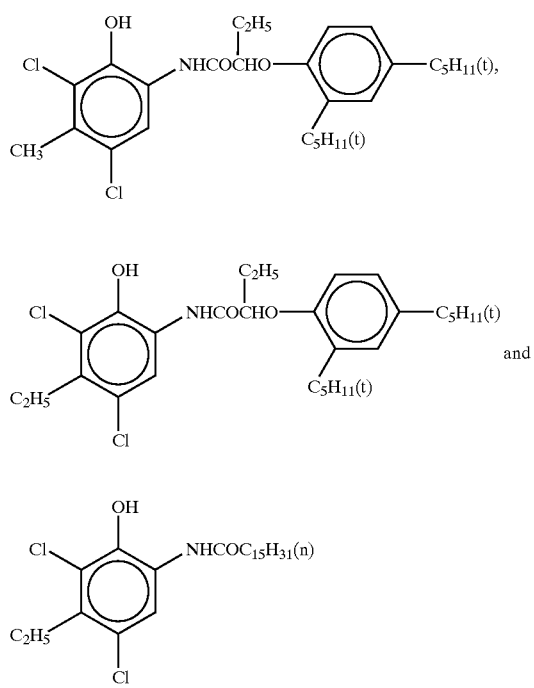
(C p d - 1) Color-image stabilizer
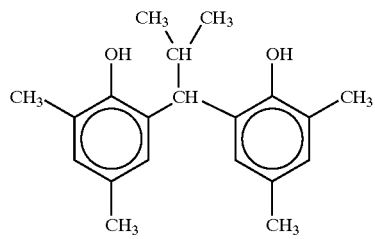
number-average molecular weight 60,000
(C p d - 2) Color-image stabilizer (Cpd-3) Color-image stabilizer
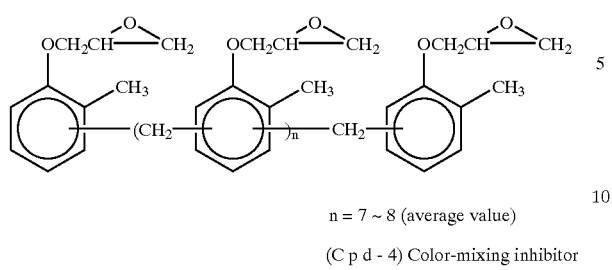
n = 7 ~ 8 (average value)
(Cpd-4) Color-mixing inhibitor
A mixture in 1:1:1 (molar ratio) of
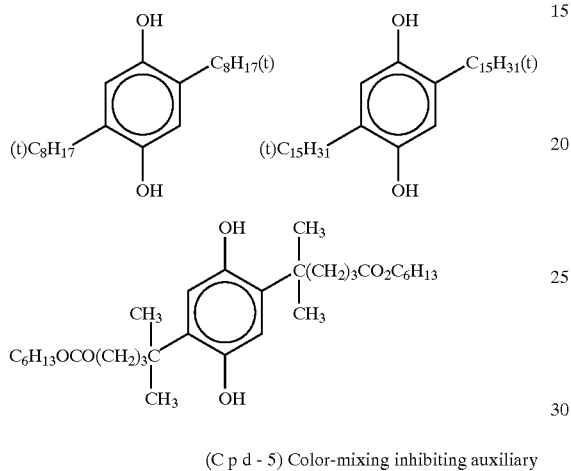
(Cpd-5) Color-mixing inhibiting auxiliary
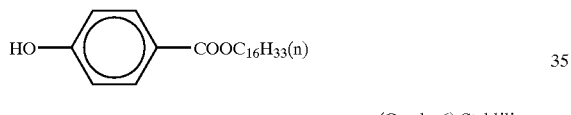
(Cpd-6) Stablilizer
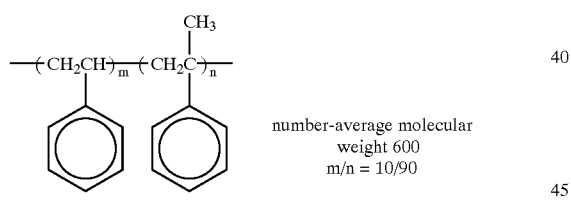
number-average molecular
weight 600
m/n = 10/90
(Cpd-7) Color-mixing inhibitor
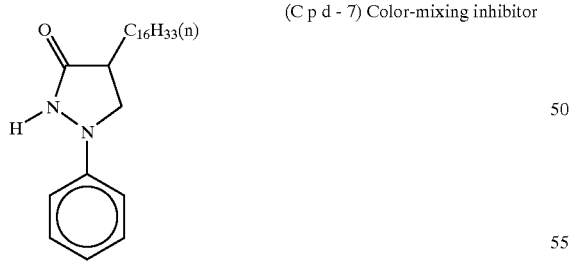
(Cpd-8) Color-image stabilizer
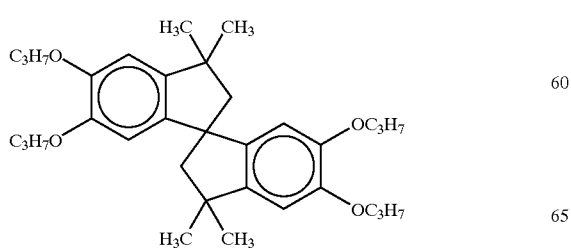
(Cpd-9) Color-image stabilizer
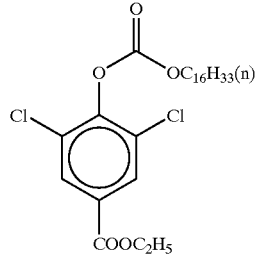
(Cpd-10) Color-image stabilizer
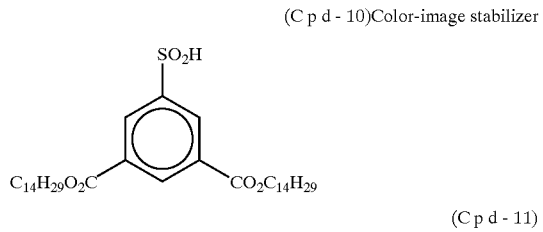
(Cpd-11)
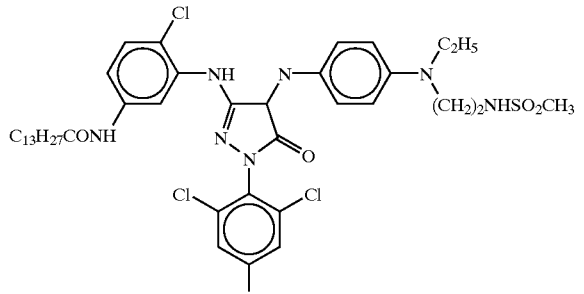
(Cpd-12)
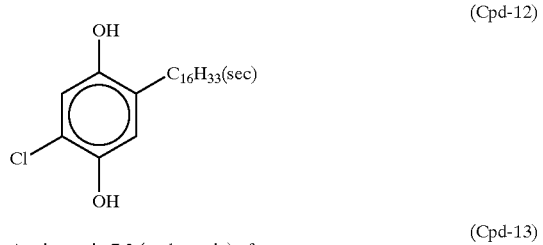
(Cpd-13)
A mixture in 7:3 (molar ratio) of
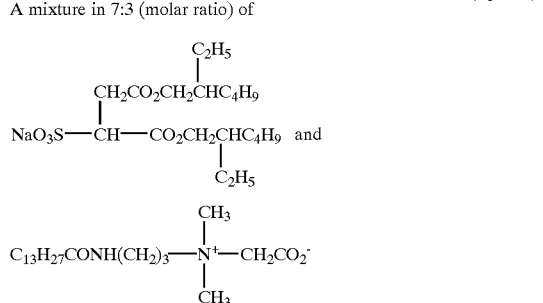
(Cpd-14)
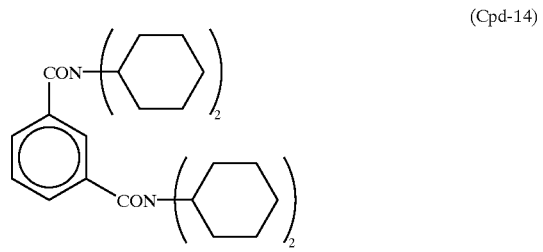

(Cpd-15)
A mixture in 1:1 (molar ratio) of
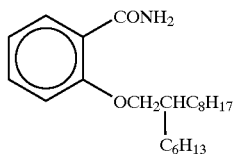 and 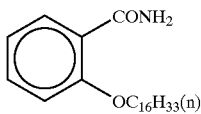
(Cpd-16)
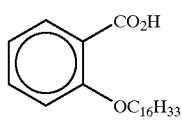
(Cpd-17)
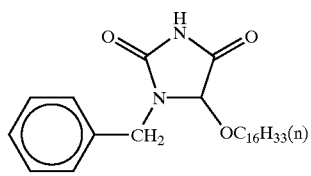
(Cpd-18)
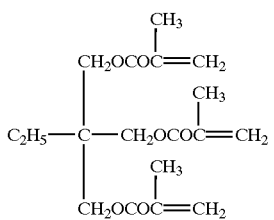
(Cpd-19)
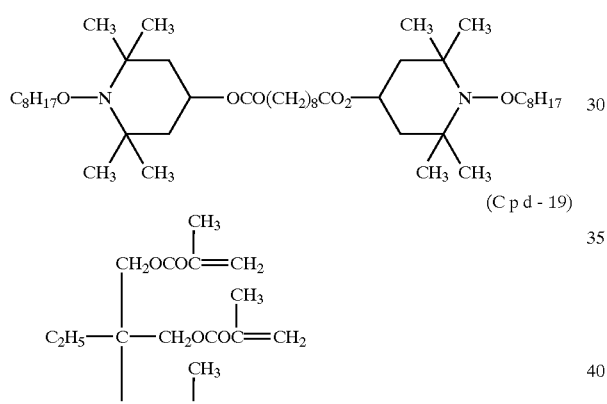
(UV-1) Ultraviolet absorbing agent
(UV-2) Ultraviolet absorbing agent
(UV-3) Ultraviolet absorbing agent
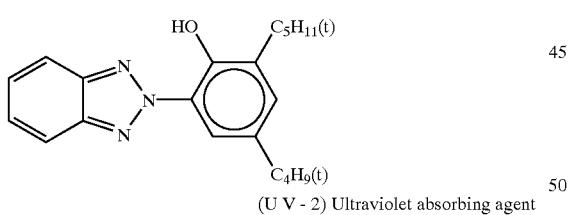
(UV-4) Ultraviolet absorbing agent
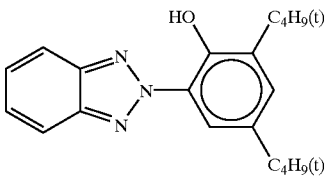
(UV-5) Ultraviolet absorbing agent
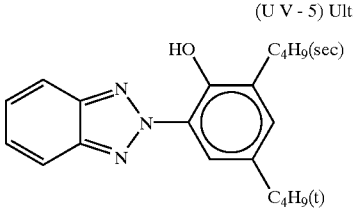
(UV-6) Ultraviolet absorbing agent
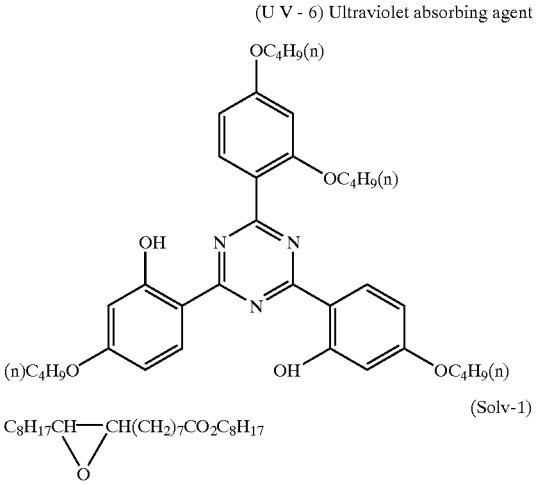
(Solv-1)
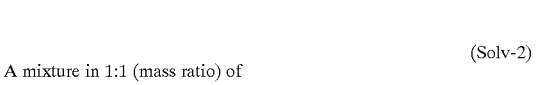
(Solv-2)
A mixture in 1:1 (mass ratio) of
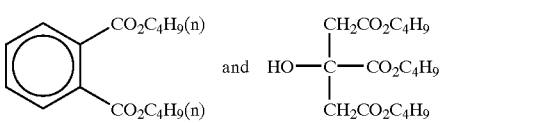
(Solv-3)
$C_4H_9OCO(CH_2)_8CO_2C_4H_9$
(Solv-4)
$O=P(OC_6H_{13}(n))_3$
(Solv-5)
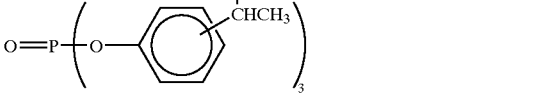
(Solv-6)
A mixture in 1:1 (mass ratio) of
 and -continued

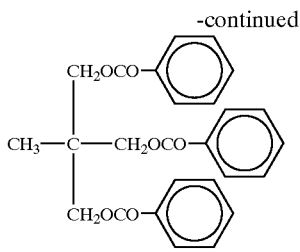 (Solv-7)

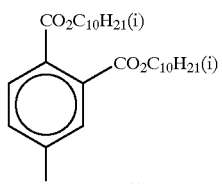 (Solv-8)

$C_8H_{17}OCO(CH_2)_8CO_2C_8H_{17}$ (Solv-9)

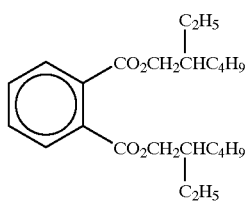 and 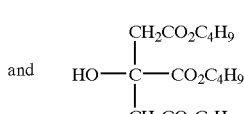

Further, light-sensitive material 401 was made in the same manner as the thus-prepared silver halide color photographic light-sensitive material (001), except for replacing the yellow coupler of the emulsified dispersion A for the first layer of the silver halide color photographic light-sensitive material (001) prepared as described above, with the coupler for comparison (C-1) which was used in the foregoing Comparative Example 1, in an equivalent molar amount. Likewise, light-sensitive material 402 was made in the same manner as above, except for replacing the yellow coupler with the coupler for comparison (C-2) which was used in the foregoing Comparative Example 2, in an equivalent molar amount. Further, light-sensitive materials (403) to (408) according to the present invention were made in the same manner as above, except for replacing the yellow coupler with the dye-forming couplers (1), (2), (20), (30), (35) and (40), which included those used in Examples 1 to 4, in an equivalent molar amount, respectively.

Average particle size of each of the above-prepared dispersions of lipophilic fine-particles containing a yellow coupler was in the range of 0.10 to 0.20 μm.

The above-described light-sensitive material (001) was stored at 25° C., 55% RH, for 10 days, and then cut into a 127-mm width roll. After that, the roll-like material was exposed to light imagewise and subjected to a continuous processing (running test) with a mini-Lab printer processor (PP1258 AR, trade name, made by Fuji Photo Film Co., Ltd.) in accordance with the process mentioned below, until the amount of replenisher to the color developer tank became 2 times the tank capacity.

| Processing step | Temperature | Time | Replenishment rate* |
|---|---|---|---|
| Color development | 38.5° C. | 45 sec | 45 ml |
| Bleach-fixing | 38.0° C. | 45 sec | 35 ml |
| Rinse (1) | 38.0° C. | 20 sec | — |
| Rinse (2) | 38.0° C. | 20 sec | — |
| Rinse (3) | **38.0° C. | 20 sec | — |
| Rinse (4) | **38.0° C. | 30 sec | 121 ml |

*Replenishment rate per m² of the light-sensitive material to be processed.
**A rinse cleaning system RC50D, trade name, manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. (The rinse was made in a tank counter-current system from (1) to (4).)

The composition of each processing solution was as follows.

| (Color developer) | (Tank solution) | (Replenisher) |
|---|---|---|
| Water | 800 ml | 800 ml |
| Dimethylpolysiloxane-series surfactant (Silicone KF351A/ trade name, Shin-Etsu Chemical Co., Ltd.) | 0.1 g | 0.1 g |
| Triethanolamine | 11.6 g | 11.6 g |
| Ethylenediamine tetraacetic acid | 4.0 g | 4.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-series fluorescent whitening agent (Hakkol FWA-SF/trade name, Showa Chemical Industry Co., Ltd.) | 2.5 g | 5.0 g |
| Sodium sulfite | 0.1 g | 0.1 g |
| Disodium-N,N-bis(sulfonatoethyl) hydroxylamine | 8.5 g | 11.1 g |
| N-ethyl-N-(β-methanesulfonamidoethyl)-3-methyl-4-amino-4-aminoaniline · ½ sulfate · 1 hydrate | 5.0 g | 15.7 g |
| Potassium carbonate | 26.3 g | 26.3 g |
| Water to make | 1000 ml | 1000 ml |
| pH (25° C./adjusted using potassium hydroxide and sulfuric acid) | 10.15 | 12.50 |

| (Bleach-fixing solution) | (Tank solution) | (Replenisher) |
|---|---|---|
| Water | 800 ml | 800 ml |
| Ammonium iron (III) ethylenediaminetetraacetate | 47.0 g | 94.0 g |
| Ethylenediamine tetraacetic acid | 1.4 g | 2.8 g |
| m-Carboxymethylbenzenesulfinic acid | 8.3 g | 16.5 g |
| Nitric acid (67%) | 16.5 g | 33.0 g |
| Imidazole | 14.6 g | 29.2 g |
| Ammonium thiosulfate (750 g/l) | 107 ml | 214 ml |
| Ammonium sulfite | 16.0 g | 32.0 g |
| Potassium methbisulfite | 23.1 g | 46.2 g |
| Water to make | 1000 ml | 1000 ml |
| pH (25° C./adjusted using acetic acid and ammonia) | 6.0 | 6.0 |

| (Rinse solution) | (Tank solution) | (Replenisher) |
|---|---|---|
| Sodium chlorinated-isocyanurate | 0.02 g | 0.02 g |
| Deionized water (conductivity: 5 µS/cm or less) | 1000 ml | 1000 ml |
| PH | 6.5 | 6.5 |

Then, each of the light-sensitive materials was subjected to gradation exposure via an optical wedge having a three-color separating sensitometric filter, using a sensitometer (FWH Model, made by Fuji Photo Film Co., Ltd., its light source has a color temperature of 3200° K.). At that time, the exposure was carried out so that 0.1 second of the exposure time gave the exposure amount of 250 lx·sec.

Separately, each of the light-sensitive materials was subjected to the scanning exposure described below.

The scanning exposure was carried out using a scanning exposure device illustrated in FIG. 1 of JP-A-8-16238. As the light source, a light source of 688 nm (R light) taken out by using a laser semiconductor, a light source of 532 nm (G light) and a light source of 473 nm (B light) each taken out by combining a semiconductor laser with SHG, respectively, were used. The quantity of R light was modulated by an external modulator, and laser beams were scan-exposed to a sample moving in the direction vertical to the scanning direction by the reflection to a rotating polyhedron. The scanning pitch was 400 dpi and the average exposure time per pixel was 8×10⁻⁸ sec. The temperature of the semiconductor laser was kept constant by using a Peltier device to prevent the quantity of light from being changed by temperature.

Each of the exposed samples was processed with the foregoing running solution, and then evaluated in the same manner as the light-sensitive materials in Comparative Examples 3 and 4 and Examples 5 to 8.

The results which were obtained, demonstrate that each of the light-sensitive materials of the present invention using the dye-forming couplers of the present invention exhibits a high color-forming property and each of the dyes formed from the couplers is excellent in both hue and fastness.

Example 10

A light-sensitive material was made in the same manner as the sample 101 in JP-A-11-305396, except for replacing ExY-2 and ExY-3 in the 13th layer and the 14th layer of the Sample 101 as described in JP-A-11-305396 with the dye-forming coupler (1) according to the present invention in an equimolar amount, respectively. The light-sensitive material thus obtained was exposed and processed in the same manner as in Example 1 of JP-A-11-305396, and then evaluated according to the method described in Examples of the present application. The similar results as in the above-mentioned Example 5 in the present application were obtained.

Example 11

Light-sensitive material was made in the same manner as Sample 107 in Example 1 of JP-A-11-84601, except for replacing the couplers C-5, C-6 and C-10 in the 13th layer and the 14th layer, and C-6 and C-10 in the 15th layer of the Sample 107 in the Example 1 in JP-A-11-84601, with the dye-forming coupler (1) according to the present invention, in an equimolar amount, respectively. The light-sensitive material thus obtained was exposed and processed in the same manner as in Example 1 of JP-A-11-84601, and then evaluated according to the method described in Examples of the present application. The similar results as in the above-mentioned Example 5 in the present application were obtained.

Examples 12 to 15

1. Preparation of Dyes (D-1B) to (D-4B)

The following dyes: D-1B (wherein the coupler (1B) was used), D-2B (wherein the coupler (2B) was used), D-3B (wherein the coupler (20B) was used), and D-4B (wherein the coupler (30B) was used), which were azomethine dye compounds obtained from the dye-forming couplers of the present invention, were synthesized in the same manner as the "Preparation of a dye for comparison (CD-2)" in the above-mentioned Comparative Example 2, except for replacing the coupler for comparison (C-2) with the above-shown exemplified coupler (1B), coupler (2B), coupler (20B) and coupler (30B) of the present invention, respectively.

(D-1B)

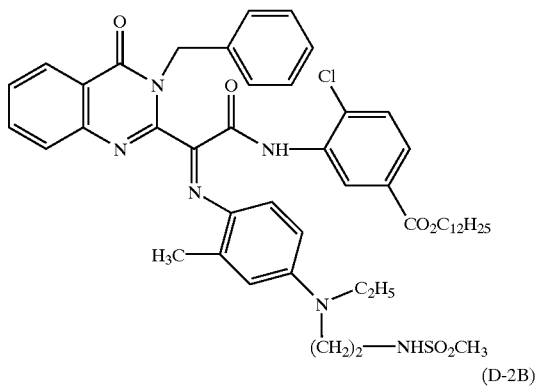

(D-2B)

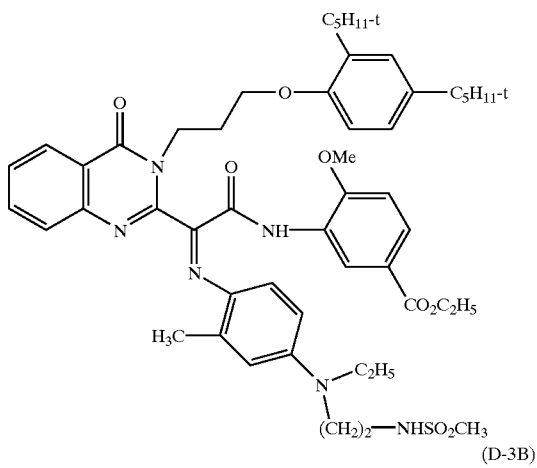

(D-3B)

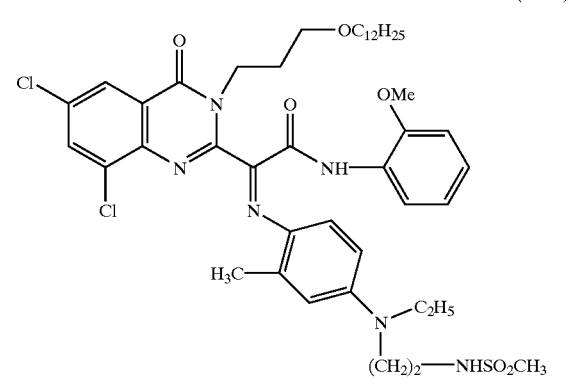

(D-4B)

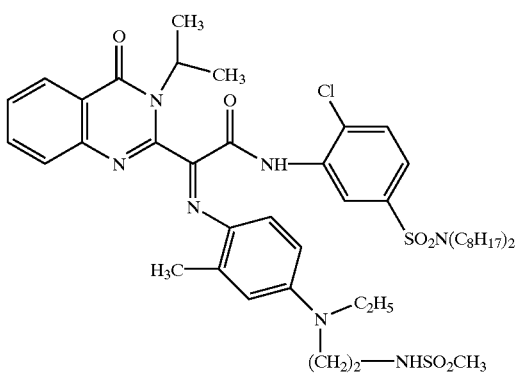

Measurement of Absorption Spectrum

Using each of the dyes for comparison (CD-1) and (CD-2) which were obtained in the above-mentioned Comparative Examples 1 and 2, and the Dyes (D-1B) to (D-4B) which were obtained in Examples 12 to 15 described above, absorption spectra were measured in the following manner.

1.5 mg of any one of the dyes for comparison (CD-1) to (CD-2), and Dyes (D-1B) to (D-4B) was precisely weighed in a 100-ml measuring flask. 100 ml of ethyl acetate was added to dissolve the dye. Each resulting solution was diluted with ethyl acetate, to prepare a sample solution 101B containing the dye for comparison (CD-1), a sample solution 102B containing the dye for comparison (CD-2), a sample solution 103B containing the Dye (D-1B), a sample solution 104B containing the Dye (D-2B), a sample solution 105B containing the Dye (D-3B), and a sample solution 106B containing the Dye (D-4B), respectively.

Each of the thus-obtained sample solutions 101B to 106B was placed in 1 cm-thick quartz cell, and visible absorption spectrum was measured by a ultraviolet-visible spectrophotometer, manufactured by Simadzu Corporation. Based on the spectrum, each molecular extinction coefficient was calculated. Further, as the parameter that expresses the sharpness at the foot portion of a peak of the absorption curve at the longer wavelength side of the dye to be used, $\Delta S(0.05)/nm$ of each the dye to be used was obtained according to the following way. Assuming that absorbance (A) of the maximum absorption wavelength ($\lambda max$) is 1, the wavelength ($\lambda(0.05)$) corresponding to A=0.05 at the longer wavelength side was measured. The $\Delta S(0.05)/nm$ is obtained by calculation according to the following expression:

$$\Delta S(0.05) = \lambda max - \lambda(0.05)$$

The results that were obtained by the above calculation, are shown in Table 5.

TABLE 5

| Sample No. | Kind of Coupler | Kind of Dye | ε | ΔS (0.05)/nm | Remarks |
|---|---|---|---|---|---|
| 101B | Coupler for comparison (C-1) | CD-1 | $1.65 \times 10^4$ | 78.0 | Comparative Example |

TABLE 5-continued

| Sample No. | Kind of Coupler | Kind of Dye | ε | ΔS (0.05)/nm | Remarks |
|---|---|---|---|---|---|
| 102B | Coupler for comparison (C-2) | CD-2 | $2.76 \times 10^4$ | 74.2 | Comparative Example |
| 103B | Coupler (1B) | D-1B | $2.82 \times 10^4$ | 70.3 | This invention |
| 104B | Coupler (2B) | D-2B | $2.85 \times 10^4$ | 64.1 | This invention |
| 105B | Coupler (20B) | D-3B | $2.83 \times 10^4$ | 66.5 | This invention |
| 106B | Coupler (30B) | D-4B | $2.81 \times 10^4$ | 68.2 | This invention |

From the results in Table 5, it is understood that the dyes obtained from the dye-forming couplers of the present invention exhibit higher molecular extinction coefficient than those obtained from the dye-forming coupler for comparison. This means that the dyes of the present invention enables to provide the density of the conventional level even in a thinner layer of the light-sensitive material and the like. It is further understood that the dyes of the present invention exhibit small $\Delta S(0.05)/nm$, which means that they are excellent in sharpness at the foot portion of a peak in interest of the absorption curve at the longer wavelength side. In other words, in the silver halide photographic light-sensitive material containing the coupler of the present invention, only a small portion of a reddish tinge was mixed in a yellow dye obtained from the coupler, resulting in improvement in not only color reproduction of the obtained image (particularly color reproduction of lemon yellow), but also in sharpness.

Test of Fading Resistance of Dyes to an Acid

With respect to each of the above-mentioned dyes for comparison (CD-1) and (CD-2) and the above-mentioned dyes (CD-1B) to (D-4B), the test of fading resistance to an acid was carried out in the same manner as described in the above.

Sample solution 201B (wherein the dye for comparison (CD-1) in the above-mentioned Comparative example 1 was used), Sample solution 202B (wherein the dye for comparison (CD-2) in the above-mentioned Comparative example 2 was used), Sample solution 203B (wherein the Dye (D-1B) was used), Sample solution 204B (wherein the dye (D-2B) was used), Sample solution 205B (wherein the dye for comparison (D-3B) was used), and Sample solution 206B (wherein the dye (D-4B) was used) were prepared, respectively, in the same manner as the sample solutions 201 to 206 of the above-mentioned Example 1 to 4, except that Dyes (D-1B) to (D-4B) were used in place of Dyes (D-1) to (D-4), respectively. Then, to each of the thus-obtained sample solutions 201B to 206B, the test of fading resistance of dyes to an acid was performed in the same manner as in the above-mentioned Examples 1 to 4.

The results that were obtained are shown in Table 6.

TABLE 6

| Sample No. | Kind of Coupler | Kind of Dye | Remaining ratio (%) | Remarks |
|---|---|---|---|---|
| 201B | Coupler for comparison (C-1) | CD-1 | 15 | Comparative Example |

TABLE 6-continued

| Sample No. | Kind of Coupler | Kind of Dye | Remaining ratio (%) | Remarks |
|---|---|---|---|---|
| 202B | Coupler for comparison (C-2) | CD-2 | 94 | Comparative Example |
| 203B | Coupler (1B) | D-1B | 98 | This invention |
| 204B | Coupler (2B) | D-2B | 98 | This invention |
| 205B | Coupler (20B) | D-3B | 99 | This invention |
| 206B | Coupler (30B) | D-4B | 97 | This invention |

It is apparent from the Table 6 that the dye obtained from the dye-forming coupler of the present invention is remarkably excellent in fastness of the dye of an acid.

Examples 16 to 19

1. Preparation of each of Emulsified Dispersions of Couplers (1B), (2B), (20B) and (30B)

Each of emulsified dispersions of couplers according to the present invention was prepared in the same manner as the "1. Preparation of Emulsified Dispersion of Coupler for comparison (C-1)" in the above-described Comparative Example 3, except for replacing the coupler for comparison (C-1) with the foregoing exemplified couplers (1B), (2B), (20B) and (30B) of the present invention, respectively.

2. Preparation of Light-sensitive Material of the Present Invention

In the same manner as in "2. Preparation of Light-sensitive material for comparison" in the above-described Comparative Example 3, Sample 303B (wherein the Coupler (1B) was used), Sample 304B (wherein the Coupler (2B) was used), Sample 305B (wherein the Coupler (20B) was used), Sample 306B (wherein the Coupler (30B) was used), each of which was the light-sensitive material of the present invention, were prepared, except for replacing the emulsified dispersion of Coupler for comparison (C-1) with the emulsified dispersions of the foregoing exemplified couplers (1B), (2B), (20B) and (30B) of the present invention, respectively.

Evaluation Tests of Color-image Fastness

Using the Samples 303B to 306B which were obtained in the foregoing Examples 16 to 19, and, for comparison, the sample 301B (which is the same as sample 301 in the above-described Comparative Example 3) and the sample 302B (which is the same as sample 302 in the above-described Comparative Example 4), the evaluation test of color-image fastness was carried out in the same manner as the samples 301 to 306 which were obtained in the foregoing Comparative examples 3 and 4 and Examples 5 to 8.

First, each of the samples 301B to 306B was wedge-wise exposed to a white light, and then subjected to color-development processing according to the processing steps in the same manner as the above-described Examples 5 to 8.

The processed samples each colored yellow. Each of the light-sensitive material, the samples 303B to 306B according to the present invention gave the dye image having a sharper hue, as compared to those of light-sensitive material for comparison, the samples 301B to 302B.

Then, each of the samples 301B to 306B processed for color development was irradiated with Xenon light source (100,000 lux) with intermittent illumination under the conditions of light for 5 hours/darkness for 1 hour, for 14 days, and light-fastness of the dye image was evaluated. The density after irradiation at a portion where the initial density D=1.0 is indicated as the remaining ratio in percent. The results that were obtained are shown in Table 7.

As is apparent from Table 7, it is understood that the light-sensitive materials of the present invention are excellent in light-fastness.

TABLE 7

| Sample No. | Kind of Coupler | Kind of Dye | Remaining ratio (%) | Remarks |
|---|---|---|---|---|
| 301B | Coupler for comparison (C-1) | CD-1 | 85 | Comparative Example |
| 302B | Coupler for comparison (C-2) | CD-2 | 74 | Comparative Example |
| 303B | Coupler (1B) | D-1B | 93 | This invention |
| 304B | Coupler (2B) | D-2B | 91 | This invention |
| 305B | Coupler (20B) | D-3B | 94 | This invention |
| 306B | Coupler (30B) | D-4B | 91 | This invention |

Example 20

Light-sensitive material 401B was made in the same manner as the silver halide color photographic light-sensitive material (001) prepared in the above-mentioned Example 9, except for replacing the yellow coupler of the emulsified dispersion A for the first layer of the silver halide color photographic light-sensitive material (001) prepared in the above-mentioned Example 9, with the coupler for comparison (C-1) which was used in the foregoing Comparative Example 1, in an equivalent molar amount. Likewise, light-sensitive material 402B was made in the same manner as above, except for replacing the yellow coupler with the coupler for comparison (C-2) which was used in the foregoing Comparative Example 2, in an equivalent molar amount. Further, light-sensitive materials (403B) to (408B) according to the present invention were made in the same manner as above, except for replacing the yellow coupler with the dye-forming couplers (1B), (2B), (20B), (30B), (35B) and (40B), which included those used in Examples 12 to 15, in an equivalent molar amount, respectively.

Average particle of each of the above-prepared dispersions of lipophilic fine-particles containing a yellow coupler was in the range of 0.10 to 0.20 μm.

In the same manner as the above-described Example 9, the above-described light-sensitive material (001) was subjected to the continuous processing (running test).

Then, in the same manner as the above-described Example 9, each of the light-sensitive material samples (401B) to (408B) was subjected to the gradation exposure.

Separately, each of the light-sensitive material samples (401B) to (408B) was subjected to the scanning exposure in the same manner as the above-mentioned Example 9.

Each of the exposed samples (401B) to (408B) was processed with the foregoing running solution in the same manner as the above-mentioned Example 9. Then, the processed samples were tested and evaluated in the same manner as in the above-described Comparative examples 3 to 4, Examples 5 to 8, and Examples 16 to 19.

The results which were obtained, demonstrate that each of the light-sensitive materials of the present invention using

139 the dye-forming couplers of the present invention exhibits a high color-forming property and each of the dyes formed from the couplers is excellent in both hue and fastness.

Example 21

A light-sensitive material was made in the same manner as Sample 101 in JP-A-11-305396, except for replacing the couplers ExY-2 and ExY-3 in the 13th layer and the 14th layer of the Sample 101 as described in JP-A-11-305396, with the dye-forming coupler (1B) according to the present invention, in an equimolar amount, respectively. The light-sensitive material thus obtained was exposed and processed in the same manner as in Example 1 of JP-A-11-305396, and then evaluated according to the method described in Examples in the present application. The similar results as in the above-mentioned Example 16 in the present application were obtained.

Example 22

A light-sensitive material was made in the same manner, as Sample 107 in Example 1 in JP-A-11-84601, except for replacing the couplers C-5, C-6 and C-10 in the 13th layer and the 14th layer, and C-6 and C-10 in the 15th layer of the Sample 107 as described in Example 1 of JP-A-11-84601, with the dye-forming coupler (1B) of the present invention, in an equimolar amount, respectively. The light-sensitive material thus obtained was exposed and processed in the same manner as in Example 1 of JP-A-11-84601, and then evaluated according to the method described in Examples of the instant application. The similar results as in the above-mentioned Example 16 in the present application were obtained.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A silver halide photographic light-sensitive material, comprising at least one dye-forming coupler represented by formula (I):

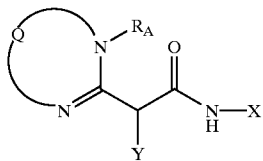

formula (I)

wherein Q represents a residue that forms, together with the —N—C=N— moiety, a nitrogen-containing 6-membered ring; $R_A$ represents an aryl group, a heterocyclic group, or an —$(R_1)_r$—$(R_4)_m$ group; X represents an aryl group; Y represents a hydrogen atom, or a group that is capable of being split-off upon a coupling reaction with an oxidized product of a developing agent;
wherein,
when $R_A$ represents an —$(R_1)_r$—$(R_4)_m$ group, $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may

140 be the same or different independently, or $R_4$s may be combined together to form a multiple bond, or alternatively $R_4$s may bond with each other to form a ring, when m is 2 or more; and the —$(R_1)_r$—$(R_4)_m$ group does not represent a straight-chain alkyl group.

2. The silver halide photographic light-sensitive material as claimed in claim 1, wherein the dye-forming coupler represented by formula (I) is represented by formula (IA):

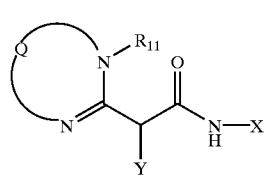

formula (IA)

wherein Q represents a residue that forms, together with the —N—C=N— moiety, a nitrogen-containing 6-membered ring; $R_{11}$ represents an aryl group or a heterocyclic group; X represents an aryl group; Y represents a hydrogen atom, or a group that is capable of being split-off upon a coupling reaction with an oxidized product of a developing agent.

3. The silver halide photographic light-sensitive material as claimed in claim 8, wherein, in the dye-forming coupler represented by formula (IA), Q is a residue that forms, together with the —N—C=N— moiety, a 4-pyrimidone ring.

4. The silver halide photographic light-sensitive material as claimed in claim 1, wherein the dye-forming coupler represented by formula (I) is represented by formula (IB):

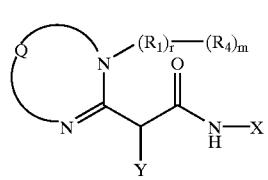

formula (IB)

wherein Q represents a residue that forms, together with the —N—C=N— moiety, a nitrogen-containing 6-membered ring; $R_1$ represents a methylene group, a methine group, or a carbon atom; r represents an integer of 1 to 30, and $R_1$s may be the same or different independently, when r is 2 or more; $R_4$ represents a substituent except for a hydrogen atom; m represents an integer of 1 to 30, and $R_4$s may be the same or different independently, or $R_4$s may be combined together to form a multiple bond, or alternatively $R_4$s may bond with each other to form a ring, when m is 2 or more; X represents an aryl group; Y represents a hydrogen atom, or a group that is capable of being split-off upon a coupling reaction with an oxidized product of a developing agent; and the —$(R_1)_r$—$(R_4)_m$ group does not represent a straight-chain alkyl group.

5. The silver halide photographic light-sensitive material as claimed in claim 4, wherein, in the dye-forming coupler represented by formula (IB), Q is a residue that forms, together with the —N—C=N— moiety, a 4-pyrimidone ring; and $R_4$ is a group selected from the group consisting of an alkyl group, an alkenyl group, an aryl group, a heterocyclic group, a halogen atom, an amino group, a hydroxyl group, a carboxyl group, a sulfo group, an acylamino group, an alkyl- or aryl-sulfonylamino group, a carbamoyl group, a sulfamoyl group, an acyl group, a sulfonyl group, an alkoxycarbonyl group, an aryloxycarbonyl group, an alkylthio group, an arylthio group, a cyano group, an alkoxy group and an aryloxy group.

6. The silver halide photographic light-sensitive material as claimed in claim 4, wherein, in the dye-forming coupler represented by formula (IB), at least one $R_4$ bonds with a carbon atom at at least one α- to δ-positions in the ($R_1$).

7. The silver halide photographic light-sensitive material as claimed in claim 1, wherein Q represents a residue that forms, together with the —N—C=N moiety, a nitrogen-containing 6-membered ring, wherein the members of the nitrogen-containing 6-membered ring are selected from the group consisting of nitrogen and carbon.

\* \* \* \* \*